United States Patent
Tan et al.

(10) Patent No.: US 11,173,470 B2
(45) Date of Patent: Nov. 16, 2021

(54) STORING MOLECULE WITHIN POROUS MATERIALS WITH A SURFACE MOLECULAR BARRIER LAYER

(71) Applicant: BOARD OF REGENTS, THE UNIVERSITY OF TEXAS SYTEM, Austin, TX (US)

(72) Inventors: Kui Tan, Plano, TX (US); Yves J. Chabal, Richardson, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 598 days.

(21) Appl. No.: 15/729,350

(22) Filed: Oct. 10, 2017

(65) Prior Publication Data
US 2018/0104668 A1    Apr. 19, 2018

Related U.S. Application Data

(60) Provisional application No. 62/406,254, filed on Oct. 10, 2016.

(51) Int. Cl.
*B01J 20/22* (2006.01)
*B01J 20/28* (2006.01)
(Continued)

(52) U.S. Cl.
CPC ............ *B01J 20/223* (2013.01); *B01D 53/02* (2013.01); *B01J 20/2808* (2013.01); *B01J 20/3425* (2013.01); *B01J 20/3491* (2013.01); *B01J 31/0209* (2013.01); *B01J 31/0237* (2013.01); *C01B 3/56* (2013.01); *C07C 7/13* (2013.01); *C07C 51/418* (2013.01); *B01D 2253/204* (2013.01); *B01D 2253/308* (2013.01); *B01D 2257/302* (2013.01); *B01D 2257/404* (2013.01); *B01D 2257/502* (2013.01);
(Continued)

(58) Field of Classification Search
CPC ........................ B01J 20/223; B01J 2531/004; B01J 2220/46; B01J 31/0237; B01J 31/0209; B01J 20/3491; B01J 20/3425; B01J 20/2808; C07C 7/13; C07C 51/418; Y02C 10/08; Y02C 20/40; Y02P 20/51; Y02P 20/152; Y02P 20/52; Y02P 20/50; Y02P 20/151; B01D 2257/302; B01D 2257/504; B01D 2257/7022; B01D 2257/502; B01D 2253/308; B01D 2257/404; B01D 2253/204; B01D 53/02; C01B 3/56
See application file for complete search history.

(56) References Cited

PUBLICATIONS

Pinto et al. "Adsorption and Activation of CO2 by Amine-Modified Nanoporous Materials Studied by Solid-State NMR and 13CO2 Adsorption", Chem. Mater. 2011, 23, 6, 1387-1395 (Year: 2011).*

(Continued)

*Primary Examiner* — Anthony J Zimmer
*Assistant Examiner* — Syed T Iqbal
(74) *Attorney, Agent, or Firm* — Parker Highlander PLLC

(57) ABSTRACT

In some aspects, the present disclosure provides compositions comprising a nanoporous material such as a metal organic framework and an amine containing compound. In some aspects, these compositions may be used to improve the affinity of a guest molecule to the nanoporous material relative a nanoporous material which had not been treated with the amine containing compound.

13 Claims, 27 Drawing Sheets

(51) Int. Cl.
  B01J 20/34    (2006.01)
  B01J 31/02    (2006.01)
  B01D 53/02    (2006.01)
  C01B 3/56     (2006.01)
  C07C 51/41    (2006.01)
  C07C 7/13     (2006.01)
(52) U.S. Cl.
  CPC ............... *B01D 2257/504* (2013.01); *B01D 2257/7022* (2013.01); *B01J 2220/46* (2013.01); *B01J 2531/004* (2013.01); *Y02C 20/40* (2020.08); *Y02P 20/151* (2015.11); *Y02P 20/50* (2015.11); *Y02P 20/52* (2015.11)

(56) References Cited

PUBLICATIONS

Donald et al. "Capture of Carbon Dioxide from Air and Flue Gas in the AlkylamineAppended Metal-Organic Framework mmen-Mg2(dobpdc)", J. Am. Chem. Soc. 2012, 134, 16, 7056-7065 (Year: 2012).*

Andirova, D., et al., "Functionalization of metal-organic frameworks for enhanced stability under humid carbon dioxide capture conditions." ChemSusChem, 8(20), pp. 3405-3409 (2015).

Böhme, Ulrike, et al. "Ethene/ethane and propene/propane separation via the olefin and paraffin selective metal-organic framework adsorbents CPO-27 and ZIF-8." Langmuir 29.27 (2013): 8592-8600.

Bonino, Francesca, et al. "Local structure of CPO-27-Ni metallorganic framework upon dehydration and coordination of NO." Chemistry of Materials 20.15 (2008): 4957-4968.

Canepa, Pieremanuele, et al. "Diffusion of small molecules in metal organic framework materials." Physical Review Letters 110.2 (2013): 026102.

Caskey, Stephen R., Antek G. Wong-Foy, and Adam J. Matzger. "Dramatic tuning of carbon dioxide uptake via metal substitution in a coordination polymer with cylindrical pores." Journal of the American Chemical Society 130.33 (2008): 10870-10871.

Chavan, Sachin, et al. "Response of CPO-27-Ni towards CO, N 2 and C 2 H 4." Physical Chemistry Chemical Physics 11.42 (2009): 9811-9822.

Choi, S., et al., "Modification of the Mg/DOBDC MOF with amines to enhance CO2 adsorption from ultradilute gases." The journal of physical chemistry letters, 3(9), pp. 1136-1141 (2012).

Choi, S., et al., "Modification of the Mg/DOBDC MOF with amines to enhance CO2 adsorption from ultradilute gases." The journal of physical chemistry letters, 3(9), pp. 1136-1141 (2012). Supporting Information.

Chopra, Tatiana Peixoto, et al. "Ethylenediamine grafting on oxide-free H-, 1/3 ML F-, and Cl-terminated Si (111) surfaces." Chemistry of Materials 27.18 (2015): 6268-6281.

Chui, Stephen S-Y., et al. "A chemically functionalizable nanoporous material [Cu3 (TMA) 2 (H2O) 3] n." Science 283.5405 (1999): 1148-1150.

Cohen, S. M., "Postsynthetic methods for the functionalization of metal-organic frameworks." Chemical reviews, 112(2), pp. 970-1000 (2011).

Cohen, Seth M. "Postsynthetic methods for the functionalization of metal-organic frameworks." Chemical Reviews 112.2 (2011): 970-1000.

Dietzel, P. DC, et al., "Adsorption properties and structure of CO 2 adsorbed on open coordination sites of metal-organic framework Ni 2 (dhtp) from gas adsorption, IR spectroscopy and X-ray diffraction," Chemical communications, 41, pp. 5125-5127 (2008).

Férey, G., "Hybrid porous solids: past, present, future." Chemical Society Reviews, 37(1), pp. 191-214 (2008).

Férey, Gerard, et al. "A chromium terephthalate-based solid with unusually large pore volumes and surface area." Science 309.5743 (2005): 2040-2042.

Furukawa, Hiroyasu, et al. "The chemistry and applications of metal-organic frameworks." Science 341.6149 (2013): 1230444.

Hwang, Y. K., et al., "Amine grafting on coordinatively unsaturated metal centers of MOFs: consequences for catalysis and metal encapsulation." Angewandte Chemie, 120(22), pp. 4212-4216 (2008).

Jeazet, Harold B., et al. "Correlation of gas permeability in a metal-organic framework MIL-101 (Cr)-polysulfone mixed-matrix membrane with free volume measurements by positron annihilation lifetime spectroscopy (PALS)." Membranes 3.4 (2013): 331-353.

Kitagawa, Susumu, Ryo Kitaura, and Shin-ichiro Noro. "Functional porous coordination polymers." Angewandte Chemie International Edition 43.18 (2004): 2334-2375.

Kuppler, R. J., et al., "Potential applications of metal-organic frameworks." Coordination Chemistry Reviews, 253(23-24), pp. 3042-3066 (2009).

Lee, Kyuho, et al. "Small-molecule adsorption in open-site metal-organic frameworks: a systematic density functional theory study for rational design." Chemistry of Materials 27.3 (2015): 668-678.

Lee, W. R., et al., "Diamine-functionalized metal-organic framework: exceptionally high CO 2 capacities from ambient air and flue gas, ultrafast CO 2 uptake rate, and adsorption mechanism." Energy & Environmental Science, 7(2), pp. 744-751 (2014).

Lee, W. R., et al., "Diamine-functionalized metal-organic framework: exceptionally high CO 2 capacities from ambient air and flue gas, ultrafast CO 2 uptake rate, and adsorption mechanism." Energy & Environmental Science, 7(2), pp. 744-751 (2014). Supporting Information.

Li, Jian-Rong, Julian Sculley, and Hong-Cai Zhou. "Metal-organic frameworks for separations." Chemical Reviews 112.2 (2011): 869-932.

Liu, H., et al., "Ligand functionalization and its effect on CO2 adsorption in microporous metal-organic frameworks." Chemistry—An Asian Journal, 8(4), pp. 778-785 (2013).

Liu, Y., et al. "Increasing the density of adsorbed hydrogen with coordinatively unsaturated metal centers in metal-organic frameworks." Langmuir, 24(9), pp. 4772-4777 (2008).

McDonald, T. M., et al., "Capture of carbon dioxide from air and flue gas in the alkylamine-appended metal-organic framework mmen-Mg2 (dobpdc)." Journal of the American Chemical Society, 134(16), pp. 7056-7065 (2012).

Mulfort, K. L., et al., "Alkali metal cation effects on hydrogen uptake and binding in metal-organic frameworks." Inorganic chemistry, 47(18), pp. 7936-7938 (2008).

Suh, Myunghyun Paik, et al. "Hydrogen storage in metal-organic frameworks," Chemical Reviews 112.2 (2011): 782-835.

Sumida, Kenji, et al. "Carbon dioxide capture in metal-organic frameworks." Chemical Reviews 112.2 (2011): 724-781.

Tan, K., et al. "Competitive coadsorption of CO2 with H2O, NH3, SO2, NO, NO2, N2, O2, and CH4 in M-MOF-74 (M=Mg, Co, Ni): the role of hydrogen bonding." Chemistry of Materials, 27(6), pp. 2203-2217 (2015).

Tan, Kui, et al. "Mechanism of preferential adsorption of SO2 into two microporous paddle wheel frameworks M (bdc)(ted) 0.5." Chemistry of Materials 25.23 (2013): 4653-4662.

Tan, Kui, et al. "Trapping gases in metal-organic frameworks with a selective surface molecular barrier layer." Nature Communications 7 (2016): 13871.

Tan, Kui, et al. "Water reaction mechanism in metal organic frameworks with coordinatively unsaturated metal ions: MOF-74." Chemistry of Materials 26.23 (2014):6886-6895.

Wu, H., et al., "High-capacity methane storage in metal-organic frameworks M2 (dhtp): the important role of open metal sites." Journal of the American Chemical Society, 131(13), pp. 4995-5000 (2009).

Yazaydin, A. Özgür, et al. "Screening of metal-organic frameworks for carbon dioxide capture from flue gas using a combined experimental and modeling approach." Journal of the American Chemical Society 131.51 (2009): 18198-18199.

(56) References Cited

PUBLICATIONS

Yazaydin, A. Özgür, et al. "Screening of metal-organic frameworks for carbon dioxide capture from flue gas using a combined experimental and modeling approach." *Journal of the American Chemical Society* 131.51 (2009): 18198-18199. (Supporting Information).

\* cited by examiner

STORING MOLECULE WITHIN POROUS MATERIALS WITH A SURFACE MOLECULAR BARRIER LAYER

This application claims the benefit of priority to U.S. Provisional Application No. 62/406,254, filed on Oct. 10, 2016, the entire contents of which are hereby incorporated by reference.

This invention was made with government support under Grant No. DE-FG02-08ER46491 awarded by the Department of Energy. The government has certain rights in the invention.

BACKGROUND

I. Field

The present disclosure relates generally to the fields of chemistry and materials science. More particularly, it concerns methods of treating nanoporous materials useful for improving the ability of the metal organic framework to bind one or more molecules. Also described herein are compositions containing a metal-organic framework and an amine containing compound.

II. Description of Related Art

Metal-organic framework (MOF) materials are crystalline nanoporous materials consisting of inorganic nodes (metal ions or clusters), also referred to secondary building units (SBUs), and organic ligands as the connecting units (Ferey, 2008). Their high surface areas and micropore structure provide an ideal environment for adsorbing small molecules, which is the basis of many important applications such as energy storage and gas capture and separation, (Suh et al., 2011; Li, et al., 2011; Sumida et al., 2011 and Kuppler et al., 2009) and even biomedicine (Horcajada et al., 2011). The main problem for gas storage is the relatively weak adsorption of gases in MOFs. The focus to enhance gas adsorption and separation has therefore been to develop metal centers that are more active (e.g. exposed metal cations) and to functionalize the ligands by incorporating functional groups such as amine, hydroxyl, and halide in the organic ligands to increase or tune the guest-host interaction. (Suh et al., 2011; Sumida et al., 2011 and Cohen, 2012) These approaches tend to target specific molecules such as through the formation of Lewis acid-base pairs, and thus lack a wider applicability (Sumida et al., 2011). Furthermore, these methods requires unique and potentially complex synthesis procedures and often leads to a decrease of internal surface area. (Cohen, 2012; Mulfort, 2008 and Liu et al., 2013) As such, methods of improving the affinity of the metal-organic frameworks that may be used to separate numerous different gas molecules are needed.

SUMMARY

In some aspects, the present disclosure provides methods of retaining several weakly bound molecules by capping the metal-organic framework with an amine molecule, such as ethylenediamine after loading.

In some aspects, the present disclosure provides compositions comprising:
(A) nanoporous material;
(B) an amine-containing compound; and
(C) a guest molecule;

wherein the guest molecule is contained within the pores of the nanoporous material and the amine-containing compound is deposited at the openings of the pores of the nanoporous material.

In some embodiments, the amine-containing compound is an alkylamine$_{(C \leq 12)}$ or substituted alkylamine$_{(C \leq 12)}$ such as a terminal amine. Some non-limiting examples of the amine-containing compound include n-propylamine, trimethylenediamine, ethanolamine, or ethylenediamine. In one embodiment, the amine-containing compound is ethylenediamine. In another embodiments, the amine-containing compound is ammonia. In some embodiments, the amine-containing compound is deposited such that the amine group of the amine-containing compound is bound to the metal atom of the nanoporous material.

In some embodiments, the nanoporous material is a metal organic framework. The metal organic framework may comprise a pore diameter of less than 25 Å such from about 1 Å to about 25 Å or from about 5 Å to about 20 Å. In some embodiments, the metal organic framework is further defined by the formula: ML, wherein:

M is a metal ion; and

L is a ligand.

In other embodiments, wherein the metal organic framework is further defined by the formula $M_2L$, wherein:

M is a metal ion; and

L is a ligand of the formula:

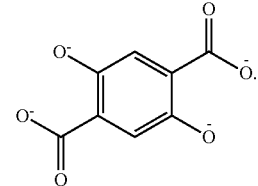

In some embodiments, divalent transition metal ion is a Co(II), Ni(II), or Zn(II) metal ion. The metal organic framework may be Ni-MOF-74, Co-MOF-74, Zn-MOF-74, or HKUST-1. In other embodiments, the metal organic framework is further defined by the formula: $M_2L_3$ wherein:

M is a trivalent metal ion; and

L is a divalent ligand.

In some embodiments, the divalent ligand is a benzenedicarboxylate or a substituted benzenedicarboxylate, such as:

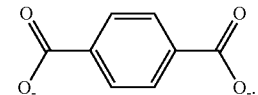

The trivalent metal ion may be a Cr(III), Al(III), or Fe(III) metal ion. In some embodiments, the metal organic framework is MIL-101-Cr or MIL-101-Fe.

In other embodiments, the metal organic framework is further defined by the formula: $M_3L_2$ wherein:

M is a metal ion; and

L is a trivalent ligand.

The trivalent ligand is a benzenetricarboxylate or a substituted benzenetricarboxylate such as:

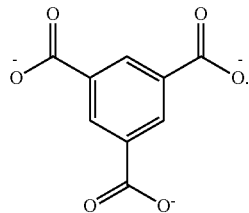

In some embodiments, metal ion is a divalent metal ion such as Cu(II). In other embodiments, the metal ion is a trivalent metal ion such as Fe(III) or Cr(III). The metal organic framework may be MIL-101-Cr.

In some embodiments, the guest molecule is a gaseous molecule such as CO, $CO_2$, $SO_2$, NO, $C_2H_2$, or $C_2H_4$.

In still another aspect, the present disclosure provides methods of preparing a composition described herein comprising reacting a nanoporous material with a gaseous mixture of an amine-containing compound. The nanoporous material may be a metal organic framework. The methods may comprise adding the amine-containing compound at a pressure from about 1 torr to about 50 torr or from about 1 torr to about 10 torr. In some embodiments, the pressure is about 4 torr.

In some embodiments, the methods further comprise a guest molecule. The guest molecule may be mixed with the amine-containing compound to obtain a gaseous mixture. In other embodiments, the guest molecule is added before the amine-containing compound. In still other embodiments, the guest molecule is added after the amine-containing compound. In some embodiments, the gaseous mixture comprises a ratio of the guest molecule to the amine-containing compound is from about 100:1 to about 1:10 or from about 25:1 to about 1:1 of the guest molecule to the amine-containing compound. The ratio may be about 10:1. In some embodiments, the guest molecule is a gas such as CO, $CO_2$, $SO_2$, NO, $C_2H_2$, or $C_2H_4$.

The methods may comprise adding the guest molecule at a pressure from about 5 torr to about 500 to, from about 250 torr to about 350 torr, from about 40 torr to about 100 torr, or from about 20 torr to about 80 torr. In some embodiments, the methods comprise a pressure of about 40 torr. In other embodiments, the methods comprise a pressure of about 300 torr. In other embodiments, the methods comprise a pressure of about 80 torr.

In still yet another aspect, the present disclosure provides a composition prepared according to the methods described herein.

In another aspect, the present disclosure provides methods of increasing the binding of a guest molecule to a nanoporous material comprising:
(A) obtaining a nanoporous material;
(B) exposing the nanoporous material to a guest molecule to form a guest absorbed metal organic framework; and
(C) exposing the guest absorbed nanoporous material to an amine-containing compound to obtain a nanoporous material with increased binding of the guest molecule.

In some embodiments, the nanoporous material is a metal organic framework. The metal organic framework may comprise a pore diameter of less than 25 Å such from about 1 Å to about 25 Å or from about 5 Å to about 20 Å. In some embodiments, the metal organic framework is further defined by the formula: ML, wherein:
M is a metal ion; and
L is a ligand.

In other embodiments, wherein the metal organic framework is further defined by the formula $M_2L$, wherein:
M is a metal ion; and
L is a ligand of the formula:

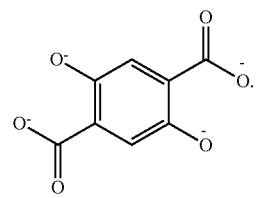

In some embodiments, divalent transition metal ion is a Co(II), Ni(II), or Zn(II) metal ion. The metal organic framework may be Ni-MOF-74, Co-MOF-74, Zn-MOF-74, or HKUST-1. In other embodiments, the metal organic framework is further defined by the formula: $M_2L_3$ wherein:
M is a trivalent metal ion; and
L is a divalent ligand.

In some embodiments, the divalent ligand is a benzenedicarboxylate or a substituted benzenedicarboxylate, such as:

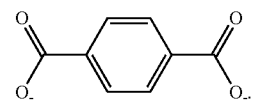

The trivalent metal ion may be a Cr(III), Al(III), or Fe(III) metal ion. In some embodiments, the metal organic framework is MIL-101-Cr or MIL-101-Fe.

In other embodiments, the metal organic framework is further defined by the formula: $M_3L_2$ wherein:
M is a metal ion; and
L is a trivalent ligand.

The trivalent ligand is a benzenetricarboxylate or a substituted benzenetricarboxylate such as:

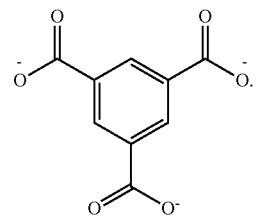

In some embodiments, metal ion is a divalent metal ion such as Cu(II). In other embodiments, the metal ion is a trivalent metal ion such as Fe(III) or Cr(III). The metal organic framework may be MIL-101-Cr.

In some embodiments, the amine-containing compound is an alkylamine$_{(C≤12)}$ or substituted alkylamine$_{(C≤12)}$ such as a terminal amine. Some non-limiting examples of the amine-containing compound include n-propylamine, trimethylenediamine, ethanolamine, or ethylenediamine. In one embodiment, the amine-containing compound is ethylenediamine. In another embodiments, the amine-containing compound is ammonia.

In some embodiments, the guest molecule is a gas such as CO, $CO_2$, $SO_2$, $C_2H_2$, $C_2H_4$, or NO. In some embodiments, step (B) and step (C) are performed simultaneously. In other embodiments, step (B) and step (C) are performed sequentially.

In some embodiments, the methods comprise exposing the metal organic framework to a ratio of the guest molecule to the amine-containing compound is from about 100:1 to about 1:10 or from about 25:1 to about 1:1 of the guest molecule to the amine-containing compound. The ratio may be about 10:1 of the guest molecule to the amine-containing compound. In some embodiments, the methods comprise adding the amine-containing compound at a pressure from about 1 torr to about 50 torr or from about 1 torr to about 10 torr. The pressure may be about 4 torr. The methods may comprise adding the guest molecule at a pressure from about 5 torr to about 1000 torr, from about 250 torr to about 350 torr, from about 40 torr to about 100 torr, or from about 20 torr to about 80 torr. In some embodiments, the pressure is about 40 torr. In other embodiments, the pressure is 80 torr. In other embodiments, the pressure is about 40 torr. The methods may comprise exposing the metal organic framework to the guest molecule or the amine-containing compound for a time period from about 30 seconds to about 4 hours or from about 1 minute to about 1 hour. In some embodiments, the time period is about 2.5 minutes. In other embodiments, the time period is about 10 minutes.

The methods may comprise exposing the metal organic framework to the guest molecule. Additionally, the methods comprise exposing the metal organic framework to the amine-containing compound. Alternatively, the methods may comprise exposing the metal organic framework to the guest molecule and the amine-containing compound.

The methods may further comprise annealing the metal organic framework for a first time period at a first temperature. The first time period may from 15 minutes to about 6 hours or from about 1 hour to about 4 hours. In some embodiments, the first time period is about 2 hours. The first temperature may be from about 100° C. to about 400° C. or from about 150° C. to about 250° C. In some embodiments, the first temperature is about 200° C. In some embodiments, the methods may further comprise annealing the metal organic framework for a second time period at a second temperature. The second time period may be from 15 minutes to about 6 hours or from about 1 hour to about 4 hours. In some embodiments, the second time period is about 2 hours. The second temperature may be from about 100° C. to about 400° C. or from about 150° C. to about 250° C. In some embodiments, the second temperature is about 200° C.

In yet another aspect, the present disclosure provides methods of separating a first gas from a mixture of gases comprising:
 (A) obtaining a nanoporous material;
 (B) exposing the nanoporous material to the mixture of gases to form a guest absorbed metal organic framework, wherein the first gas is a guest molecule absorbed by the nanoporous material; and
 (C) exposing the guest absorbed nanoporous material to an amine-containing compound to obtain a nanoporous material;
 (D) removing the non-absorbed gas molecules.

In some embodiments, the nanoporous material is a metal organic framework. The metal organic framework may comprise a pore diameter of less than 25 Å such from about 1 Å to about 25 Å or from about 5 Å to about 20 Å. In some embodiments, the metal organic framework is further defined by the formula: ML, wherein:
 M is a metal ion; and
 L is a ligand.

In other embodiments, wherein the metal organic framework is further defined by the formula $M_2L$, wherein:
 M is a metal ion; and
 L is a ligand of the formula:

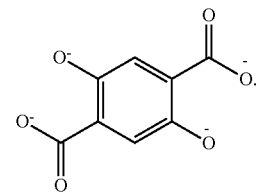

In some embodiments, divalent transition metal ion is a Co(II), Ni(II), or Zn(II) metal ion. The metal organic framework may be Ni-MOF-74, Co-MOF-74, Zn-MOF-74, or HKUST-1. In other embodiments, the metal organic framework is further defined by the formula: $M_2L_3$ wherein:
 M is a trivalent metal ion; and
 L is a divalent ligand.

In some embodiments, the divalent ligand is a benzenedicarboxylate or a substituted benzenedicarboxylate, such as:

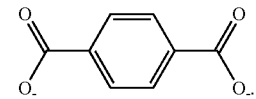

The trivalent metal ion may be a Cr(III), Al(III), or Fe(III) metal ion. In some embodiments, the metal organic framework is MIL-101-Cr or MIL-101-Fe.

In other embodiments, the metal organic framework is further defined by the formula: $M_3L_2$ wherein:
 M is a metal ion; and
 L is a trivalent ligand.

The trivalent ligand is a benzenetricarboxylate or a substituted benzenetricarboxylate such as:

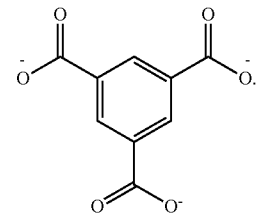

In some embodiments, metal ion is a divalent metal ion such as Cu(II). In other embodiments, the metal ion is a trivalent metal ion such as Fe(III) or Cr(III). The metal organic framework may be MIL-101-Cr.

In some embodiments, the amine-containing compound is an alkylamine$_{(C\leq12)}$ or substituted alkylamine$_{(C\leq12)}$ such as a terminal amine. Some non-limiting examples of the amine-containing compound include n-propylamine, trimethylenediamine, ethanolamine, or ethylenediamine. In one embodiment, the amine-containing compound is ethylenediamine. In another embodiments, the amine-containing compound is ammonia.

In some embodiments, the guest molecule is a gas such as CO, $CO_2$, $SO_2$, $C_2H_2$, $C_2H_4$, or NO. In some embodiments, step (B) and step (C) are performed simultaneously. In other embodiments, step (B) and step (C) are performed sequentially.

In some embodiments, the methods comprise exposing the metal organic framework to a ratio of the guest molecule to the amine-containing compound is from about 100:1 to about 1:10 or from about 25:1 to about 1:1 of the guest molecule to the amine-containing compound. The ratio may be about 10:1 of the guest molecule to the amine-containing compound. In some embodiments, the methods comprise adding the amine-containing compound at a pressure from about 1 torr to about 50 torr or from about 1 torr to about 10 torr. The pressure may be about 4 torr. The methods may comprise adding the guest molecule at a pressure from about 5 torr to about 1000 torr, from about 250 torr to about 350 torr, from about 40 torr to about 100 torr, or from about 20 torr to about 80 torr. In some embodiments, the pressure is about 40 torr. In other embodiments, the pressure is 80 torr. In other embodiments, the pressure is about 40 torr. The methods may comprise exposing the metal organic framework to the guest molecule or the amine-containing compound for a time period from about 30 seconds to about 4 hours or from about 1 minute to about 1 hour. In some embodiments, the time period is about 2.5 minutes. In other embodiments, the time period is about 10 minutes.

The methods may comprise exposing the metal organic framework to the guest molecule. Additionally, the methods comprise exposing the metal organic framework to the amine-containing compound. Alternatively, the methods may comprise exposing the metal organic framework to the guest molecule and the amine-containing compound.

The methods may further comprise annealing the metal organic framework for a first time period at a first temperature. The first time period may from 15 minutes to about 6 hours or from about 1 hour to about 4 hours. In some embodiments, the first time period is about 2 hours. The first temperature may be from about 100° C. to about 400° C. or from about 150° C. to about 250° C. In some embodiments, the first temperature is about 200° C. In some embodiments, the methods may further comprise annealing the metal organic framework for a second time period at a second temperature. The second time period may be from 15 minutes to about 6 hours or from about 1 hour to about 4 hours. In some embodiments, the second time period is about 2 hours. The second temperature may be from about 100° C. to about 400° C. or from about 150° C. to about 250° C. In some embodiments, the second temperature is about 200° C.

In some embodiments, the mixture of gases comprises ethylene and acetylene. In some embodiments, the first gas is ethylene. In other embodiments, the first gas is acetylene. In other embodiments, the mixture of gases comprises $CO_2$. In some embodiments, the first gas is $CO_2$. In some embodiments, the first gas is removed from the nanoporous material.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one of these drawings in combination with the detailed description of specific embodiments presented herein.

(FIG. 1A) Side view along c axis of hexagonal cell. (FIG. 1B) View perpendicular to the c axis. Color scheme: blue, grey, red, and white spheres represent Ni, C, O, and H atoms respectively. The interatomic space between two nearest neighbor H atoms belonging to two adjacent linkers is ~2.5 Å.

(FIG. 6B) LEIS spectra of Ni-MOF-74 with post-loaded EDA, after gentile sputtering with a dose of $3.2 \times 10^{15}$ and $2.2 \times 10^{16}/cm^2$ $Ne^+$ ions. A slight red shift of the peaks after the second sputtering (10 eV corrected in the figure), most likely resulting from sample charging due to the ion exposure and insulating nature of the MOFs, has been corrected. (FIG. 6C) Energy barrier for the diffusion of a CO molecule along the one-dimensional channel of Ni-MOF-74. Red circles: all the metal centers are saturated with CO (FIG. 8). Black diamonds: all the metal centers are saturated with EDA molecules. The inset in FIG. 6C shows the relaxed atomic position of a CO molecule at the middle of the Ni-MOF-74 channel, where all the adsorption metal sites have been saturated with EDA molecules. The dashed red box shows the CO molecule. Black, red, white, grey, and blue spheres represent C, O, H, N, and Ni atoms, respectively.

(FIG. 15C) Relaxed atomic position of EDA molecules at the middle of the Ni-MOF-74 channel upon loading 2 $H_2O$ molecule(s). Black, red, white, grey, and blue spheres represent C, O, H, N, and Ni atoms, respectively.

(FIG. 16B) Similar spectra obtained for samples without EDA capping. The bottom spectrum in each case (black) shows that there is a very small amount of water in both samples prior to introducing 8 Torr water vapor.

(FIG. 19A), (FIG. 19B), (FIG. 19C), (FIG. 19D), and (FIG. 19E) show addition of 0, 1, 3, 4, and 6 water molecules. Water molecules can be added at many different places and we show here the structures corresponding to the largest perturbation on the system, i.e. structures that show the largest deviation from (FIG. 19A).

(FIG. 20B) Time evolution of the intensities of the ν(NO) in capped HKUST-1 before (black diamonds, continuation of FIG. 14) and after (orange triangles) exposure to 8 Torr $H_2O$. The error bars of the ν(NO) normalized integrated band intensity in panel (b) do not exceed 0.02.

(FIG. 21C) ν($CO_2$) band evolution upon evacuation in vacuum (<20 mTorr) for HKUST-1 with (black diamonds) and without (red circles) post-loaded EDA. All the spectra were collected at 24° C. and referenced to the activated MOF in vacuum. The error bars of normalized integrated areas do not exceed 0.03. The loading procedure of $CO_2$+EDA (~80 Torr+~4 Torr) in HKUST-1 is the same as that in MOF-74. The uptake of $CO_2$ within HKUST-1 sample around ~80 Torr is measured to be 27.3 mg/g (Yazaydin et al., 2009). The coordinatively bonded EDA at the $Cu^{2+}$ site is observed at 1044 $cm^{-1}$, associated with the ν(C—N) mode.

(FIG. 29B) Time evolution of the ν(CO) band (2170 $cm^{-1}$) by measuring the integrated areas upon evacuation (<20 mTorr) for pristine (red circles) and alkyl amine post-loaded samples.

(FIG. 32B) HKUST-1 sample with the simulated pattern from single crystal data from Xiang, et al., 2009.

(FIG. 34B) Evolution of infrared spectra of pre-loaded $CO_2$ molecules in Ni-MOF-74 after being exposed to ~4 Torr EDA. The bottom black spectrum shows the adsorbed $CO_2$ after subsequent evacuation of ~80 Torr gas phase $CO_2$ within ~10 sec (panel a). The middle five spectra show the time dependence features after introducing EDA for 10 min. and subsequent evacuation within ~10 sec (grey). All the spectra are referenced to the activated pristine MOFs in vacuum. (FIG. 34C) $CO_2$ band evolution (2341 $cm^{-1}$) upon evacuation under vacuum (<20 mTorr) in Ni-MOF-74 with post-loaded EDA. All the spectra were collected at 24° C. and referenced to the activated MOF in vacuum. The annealing was performed by increasing the temperature to 80° C., holding for 2 h and cooling back to 24° C. for spectrum collection. (FIG. 34D) IR spectra of reloaded $CO_2$ in EDA capped Ni-MOF-74 after introducing ~80 Torr $CO_2$ for ~30 min and subsequent evacuation of gas phase within ~10 seconds, compared to the initial loading in the pristine sample without EDA.

(FIG. 35B) Evolution of infrared spectra of pre-loaded $SO_2$ molecules in Ni-MOF-74 after being exposed to ~4 Torr EDA. The bottom black spectrum shows the adsorbed $SO_2$ after subsequent evacuation of ~250 Torr gas phase within ~10 sec (FIG. 35A). The middle four spectra show the time dependence features after introducing EDA for ~10 min and subsequent evacuation within ~10 sec (orange). All the spectra are referenced to the activated pristine MOFs in vacuum. (FIG. 35C) $v_{as}(SO_2)$ band evolution (1314 cm$^{-1}$) upon evacuation in vacuum (<20 mTorr) in Ni-MOF-74 with post-loaded EDA. All the spectra were collected at ~24° C. and referenced to the activated MOF in vacuum. The annealing was performed by increasing the temperature to 80° C., holding for 2 h. and cooling back to ~24° C. for spectrum collection. (FIG. 35D) IR spectra of reloaded $SO_2$ in EDA capped Ni-MOF-74 after introducing ~250 Torr $SO_2$ for ~30 min and subsequent evacuation of gas phase within ~10 sec, compared to the initial loading in the pristine sample without EDA.

(FIG. 36B) Evolution of infrared spectra of pre-loaded $C_2H_4$ molecules in Ni-MOF-74 after being exposed to ~4 Torr EDA. The bottom black spectrum shows the adsorbed $C_2H_4$ after subsequent evacuation of ~200 Torr gas phase within ~10 sec (panel a). The middle five spectra show the time dependence features after introducing EDA for ~10 min and subsequent evacuation within ~10 sec (grey). All the spectra are referenced to the activated pristine MOFs in vacuum. (FIG. 36C) $\delta(CH_2)$ band evolution (977 cm$^{-1}$) upon evacuation in vacuum (<20 mTorr) for Ni-MOF-74 with post-loaded EDA. All the spectra were collected at 24° C. and referenced to the activated MOF in vacuum. The annealing sequence includes 2 h at 80° C., cooling back to room temperature for data collection, and an additional 2 h at 100° C., cooling back to room temperature for spectrum collection. (FIG. 36D) IR spectra of reloaded $C_2H_4$ in EDA capped Ni-MOF-74 after introducing ~200 Torr $C_2H_4$ for ~30 min and subsequent evacuation of gas phase within 10 seconds, compared to the initial loading in the pristine sample without EDA.

(FIG. 40B) Mg-MOF-74 sample. The triangle dot represent data recorded after introducing $CO_2$ at elevated temperature and cooling the sample back to room temperature under the gas phase.

DESCRIPTION OF ILLUSTRATIVE EMBODIMENTS

Figures 1A, 1B:
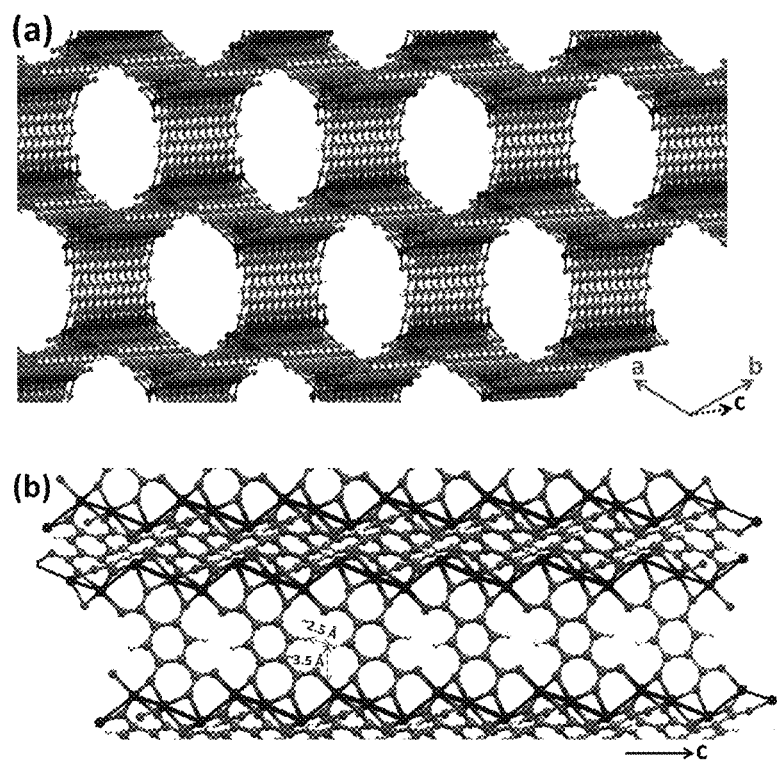
FIGS. 1A & 1B shows the crystal structure of Ni-MOF-74.

The present disclosure provides methods of improving the affinity of a nanoporous material for improving the affinity of the material for a guest molecule. The methods described herein may further comprise a metal organic framework. The method relates to treating the metal-organic framework with an amine containing compound which binds to the metal organic framework. Also provided herein are compositions containing a nanoporous material such as a metal organic framework which has been treated with an amine containing compound.

I. Nanoporous Materials

In some aspects, the present disclosure comprises methods of using a nanoporous material such as a metal-organic framework, activated carbon, or a zeolite. A nanoporous material is an organic or inorganic framework which contains a regular, porous structure having a pore size from about 0.2 to about 1000 nm. Within nanoporous materials, there are three major classifications of materials: microporous materials with a pore size from about 0.2 nm to about 2 nm, mesoporous materials with a pore size from about 2 nm to about 50 nm, or macroporous materials with a pore size from about 50 nm to about 1000 nm. In some embodiments, the present compositions relates to nanoporous materials which have a pore size from about 0.2 nm to about 100 nm, from about 1 nm to about 80 nm, or from about 5 nm to about 75 nm. The nanoporous material may have a pore size from about 1 nm, 2.5 nm, 5 nm, 10 nm, 15 nm, 20 nm, 25 nm, 30 nm, 35 nm, 40 nm, 45 nm, 50 nm, 60 nm, 70 nm, 80 nm, 90 nm, to about 100 nm, or any range derivable therein.

In some embodiments, the nanoporous material is a metal-organic frameworks. A metal-organic framework is a repeating metal ion or cluster with multiple organic ligands that form a porous higher dimension structure. Metal-organic framework may comprise a monovalent, a divalent, a trivalent, or a tetravalent ligand. Within these metal-organic frameworks exist pores which may be useful in absorbing another molecule such as a gas. In some embodiments, the metal-organic framework include metal clusters that comprise a single metal ion, two metal ions, or three or more metal ions. The metal ion may be selected from the group consisting of Group 1 through 16 metals of the IUPAC Periodic Table of the Elements including actinides, and lanthanides, and combinations thereof. Non-limiting examples of suitable metal ions include $Li^+$, $Na^+$, $K^+$, $Rb^+$, $Be^{2+}$, $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^+$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $T^{13+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, $Bi^+$, and combinations thereof. Some non-limiting examples of metal organic frameworks include those taught by Kitagawa, et al., 2004, Ferey, 2008, and Furukawa, et al., 2013, all of which are incorporated in their entirety herein by reference.

Additionally, in some embodiments, the metal-organic framework used herein optionally further comprises a non-linking ligand. In a variation, the non-linking ligand is selected from the group consisting of $O^{2-}$, sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, sulfide, hydrogen sulphate, selenide, selenate, hydrogen selenate, telluride, tellurate, hydrogen tellurate, nitride, phosphide, arsenide, arsenate, hydrogen arsenate, dihydrogen arsenate, antimonide, antimonate, hydrogen antimonate, dihydrogen antimonate, fluoride, boride, borate, hydrogen borate, perchlorate, chlorite, hypochlorite, perbromate, bromite, hypobromite, periodate, iodite, hypoiodite; and combinations thereof. Furthermore, the metal-organic framework may comprise one or more guest molecules such as water, a solvent, or a guest molecule such as $CO_2$, $SO_2$, CO, NO, $N_2$, $H_2$, ethylene, acetylene, or methane ($CH_4$).

II. Definitions

"Metal-organic frameworks" (MOFs) are framework materials, typically three-dimensional, self-assembled by the coordination of metal ions with organic linkers exhibiting porosity, typically established by gas adsorption. The MOFs discussed and disclosed herein are at times simply identified by their repeat unit as defined below without brackets or the subscript n. A mixed-metal-organic frameworks (M'MOF) is a subset of MOFs having two of more types of metal ions.

The term "unit cell" is basic and least volume consuming repeating structure of a solid. The unit cell is described by its angles between the edges ($\alpha$, $\beta$, $\gamma$) and the length of these edges (a, b, c). As a result, the unit cell is the simplest way to describe a single crystal X-ray diffraction pattern.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, $-[-CH_2CH_2-]_n-$, the repeat unit is $-CH_2CH_2-$. The subscript "n" denotes the degree of polymerization, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc. Note that for MOFs the repeat unit may also be shown without the subscript n.

"Pores" or "micropores" in the context of metal-organic frameworks are defined as open space within the MOFs; pores become available, when the MOF is activated for the storage of gas molecules. Activation can be achieved by heating, e.g., to remove solvent molecules.

"Multimodal size distribution" is defined as pore size distribution in three dimensions.

"Multidentate organic linker" is defined as ligand having several binding sites for the coordination to one or more metal ions.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Additionally, it is contemplated that one or more of the metal atoms may be replaced by another isotope of that metal. For example, the zinc atoms can be $^{64}Zn$, $^{66}Zn$, $^{67}Zn$, $^{68}Zn$, or $^{70}Zn$. Similarly, it is contemplated that one or more carbon atom(s) of a compound of the present disclosure may be replaced by a silicon atom(s). Furthermore, it is contemplated that one or more oxygen atom(s) of a compound of the present disclosure may be replaced by a sulfur or selenium atom(s).

When used in the context of a chemical group: "hydrogen" means $-H$; "hydroxy" means $-OH$; "oxo" means $=O$; "carbonyl" means $-C(=O)-$; "carboxy" means $-C(=O)OH$ (also written as $-COOH$ or $-CO_2H$); "halo" means independently $-F$, $-Cl$, $-Br$ or $-I$; "amino" means $-NH_2$; "hydroxyamino" means $-NHOH$; "nitro" means $-NO_2$; imino means $=NH$; "cyano" means $-CN$; "isocyanate" means $-N=C=O$; "azido" means $-N_3$; in a monovalent context "phosphate" means $-OP(O)(OH)_2$ or a deprotonated form thereof; in a divalent context "phosphate" means $-OP(O)(OH)O-$ or a deprotonated form thereof; "mercapto" means $-SH$; and "thio" means $=S$; "sulfonyl" means $-S(O)_2-$; and "sulfinyl" means $-S(O)-$.

In the context of chemical formulas, the symbol "—" means a single bond, "=" means a double bond, and "≡" means triple bond. The symbol "- - - -" represents an optional bond, which if present is either single or double. The symbol "⸺" represents a single bond or a double bond. Thus, the formula

covers, for example,

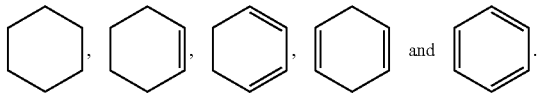

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "⁀", when drawn perpendicularly across a bond (e.g.

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⦀⦀⦀" means a single bond where the group attached to the thick end of the wedge is "into the page". The symbol "∼" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

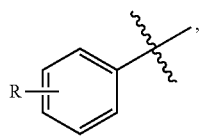

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

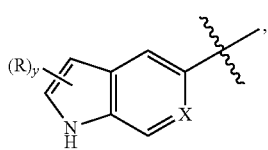

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of 20 carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous. When any of the chemical groups or compound classes defined herein is modified by the term "substituted", any carbon atom(s) in a moiety replacing a hydrogen atom is not counted. Thus methoxyhexyl, which has a total of seven carbon atoms, is an example of a substituted alkyl$_{(C1-6)}$.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group refers to a planar unsaturated ring of atoms with 4n+2 electrons in a fully conjugated cyclic π system.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —N$_{02}$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$C$_1$, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$C$_1$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

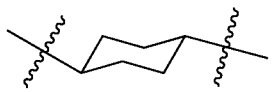 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

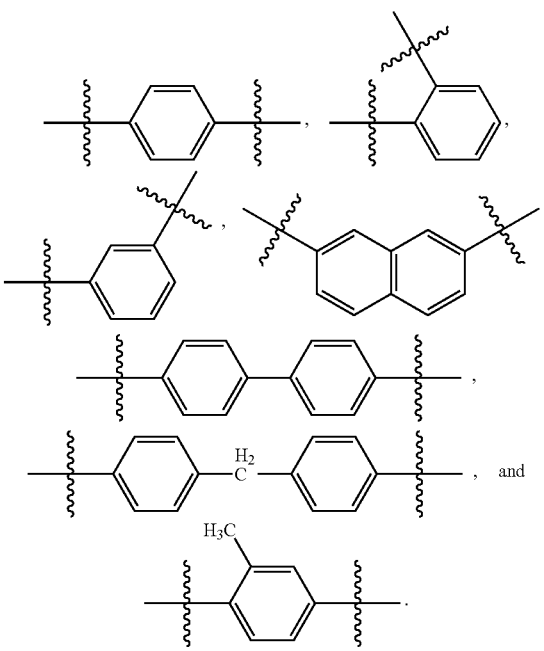

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkyl sulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "alkylamine" when used without the "substituted" modifier refers to the group NH$_2$R, in which R is an alkyl, as that term is defined above. Similarly, "dialkylamine" refers to the group NHR$_2$ and "trialkylamine" refers to the group NR$_3$, in which R is an alkyl, as that term is defined above. Similarly, the term "cycloalkylamine" and "arylamine" refers to the group NH$_2$R, in which R is a cycloalkyl and an aryl group, respectively. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The term "amine containing compound" is used to refer to a compound which contains one or more nitrogen atom with a Lewis basic pair of electrons. These nitrogen atoms may include amino, alkylamino, or dialkylamino groups as those terms are defined herein. In some embodiments, the amine containing compound is an alkylamine, cycloamine, or arylamine with 1-12 carbon atoms.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

The above definitions supersede any conflicting definition in any of the reference that is incorporated herein by reference. The fact that certain terms are defined, however, should not be considered as indicative that any term that is undefined is indefinite. Rather, all terms used are believed to describe the disclosure in terms such that one of ordinary skill can appreciate the scope and practice the present disclosure.

III. Examples

The following examples are included to demonstrate preferred embodiments of the disclosure. It should be appreciated by those of skill in the art that the techniques disclosed in the examples which follow represent techniques discovered to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods and Materials

B. Materials

The MOFs samples are synthesized by following the modified procedure from Caskey et al., 2008 and Chui et al., 1999. Anhydrous redistilled ethylenediamine (EDA, NH$_2$(CH)$_2$NH$_2$, ≥99.5%) was purchased from Sigma-Aldrich.

Ni-MOF-74:

A mixture of nickel nitrate hexahydrate (0.24 g, 0.8 mmol), 2,5-dihydroxyterephthalic (0.08 g, 0.4 mmol), 9 mL DMF and 1 mL H$_2$O was prepared in a 28 mL Teflon-lined autoclave. The autoclave was then sealed and heated to 100° C. for 3 days. After filtering and washing with 20 mL DMF, the product was collected and exchanged with methanol every 2 h during daytime for at least 3 days. Then the MOFs sample was stored in a N$_2$ glove box.

Co-MOF-74:

A mixture of cobalt nitrate hexahydrate (0.17 g, 0.6 mmol), 2,5-dihydroxyterephthalic (0.06 g, 0.3 mmol), 9 mL DMF and 1 mL H$_2$O was prepared in a 28 mL Teflon-lined autoclave. The autoclave was then sealed and heated to 100° C. for 3 days. After filtering and washing with 20 mL DMF, the product was collected and exchanged with methanol every 2 h during daytime for at least 3 days. Then the MOFs sample was stored in a N$_2$ glove box.

Zn-MOF-74:

A mixture of zinc nitrate hexahydrate (0.24 g, 0.8 mmol), 2, 5-dihydroxyterephthalic (0.08 g, 0.4 mmol), 9 mL DMF and 1 mL H$_2$O were transferred into a 28 ml Teflon-lined autoclave. The autoclave was then sealed and heated to 120° C. for 3 days. After filtering and washing with 20 mL DMF, the product was collected. Then the product was exchanged with 20 mL methanol in a glass vial every 2 h during daytime for at least 3 days. Then the MOFs sample was stored in a N$_2$ glove box.

HKUST-1:

A solution of copper nitrate hydrate (0.725 g) in deionized water (12 mL) was added to a solution of 1,3,5-benzenetricarboxylic acid (0.42 g) in deionized water (12 mL) and ethyl alcohol absolute (24 mL). The mixture was stirred for 10 min and transferred to a 100 mL Teflon-lined autoclave. The oven was heated at 110° C. for 24 h. The resultant blue crystals were filtered, washed with ethanol and chloroform. Then the MOFs sample was stored in a N$_2$ glove box.

Figures 32A, 32B:
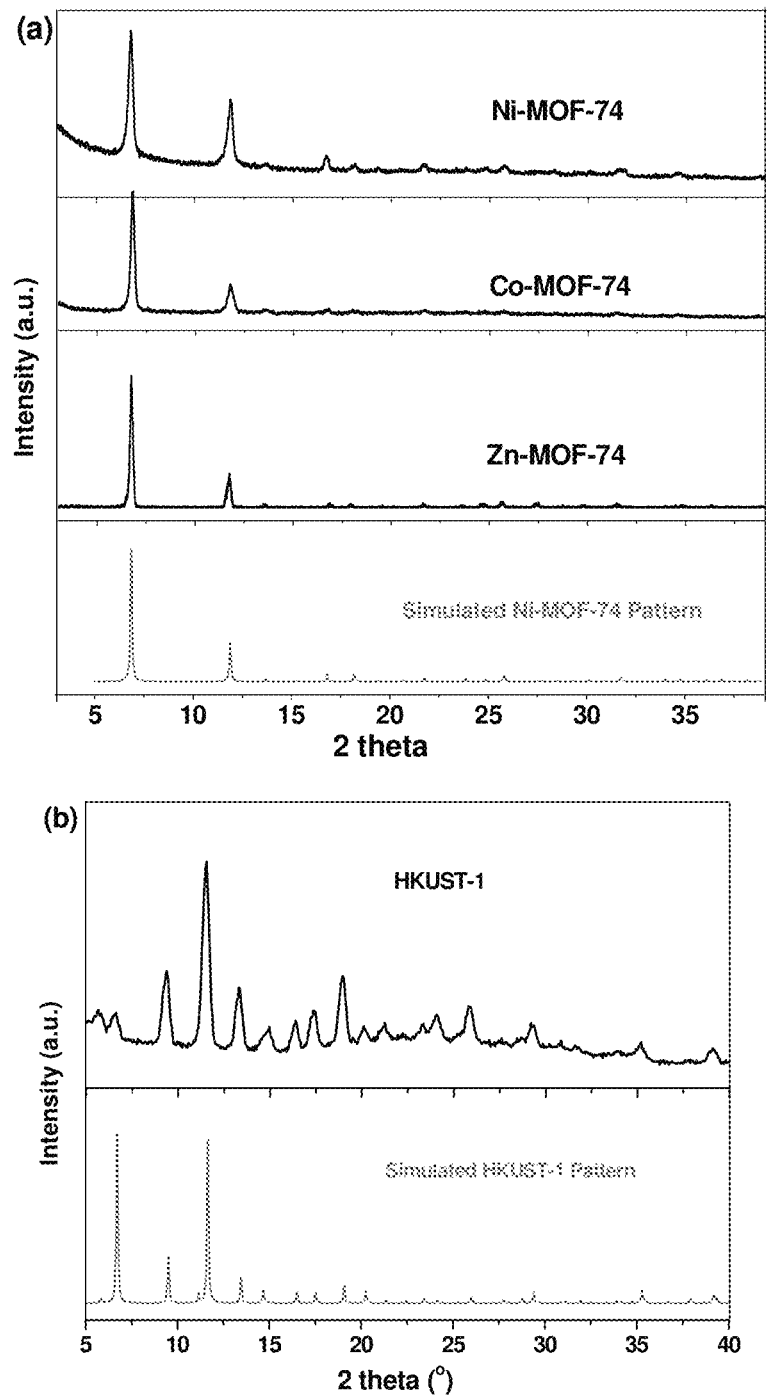
FIGS. 32A & 32B show the powder X-ray diffraction pattern of (FIG. 32A) Ni, Co, Zn-MOF-74 samples (after solvent exchange) with the simulated pattern from single crystal data from (Dietzel, et al., 2008)

The crystal structures of MOF samples (Ni, Co, Zn-MOF-74; HKUST-1) were measured by PXRD as shown in FIG. 32. The XRD diffraction patterns of the samples we studied are in agreement with literature reports. (Dietzel et al., 2008 and Xiang et al., 2009) After thorough solvent exchange, the surface areas reach 913, 1077, 774 m$^2$/g for Ni-MOF-74, Co-MOF-74, Zn-MOF-74, (5) respectively, consistent with the values reported in the original literature (Caskey et al., 2008).

B. Method

Figure 33:
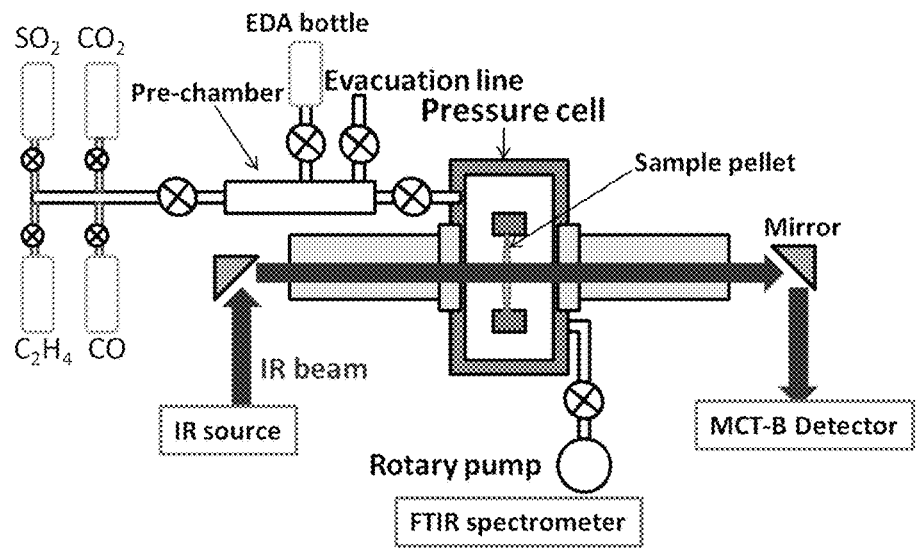
FIG. 33 shows the diagram of the environmental cell placed in the infrared spectrometer.

In Situ IR Interferometer:

All infrared spectroscopic data presented are taken by using a Nicolet 6700 FTIR spectrometer (purchased from Thermo Scientific Inc., US) equipped with a liquid $N_2$-cooled mercury cadmium telluride MCT-A detector. A vacuum cell, purchased from Specac Ltd, UK (product number P/N 5850c), is placed in the sample compartment of the infrared spectrometer with the sample at the focal point of the beam. The MOFs (powder, ~2-~5 mg) are gently pressed onto a KBr pellet (~1 cm diameter, 1-2 mm thick) and placed in the cell. The cell is connected to different gas lines (EDA vapor, $NH_3$, CO, $CO_2$, $SO_2$, $CH_2CH_2$, etc) for exposure and a vacuum line for evacuation. A pre-chamber is installed close to the cell to mix EDA vapor with other gases (see the diagram in FIG. 33). The samples are then activated by evacuation (base pressure <20 mTorr) at 180° C. for at least 3 h and then cooled back to room temperature for gas exposure measurements. All spectra are recorded in transmission mode from 650 $cm^{-1}$ (MCT-A) to 4000 $cm^{-1}$ (4 $cm^{-1}$ spectral resolution).

X-Ray Photoelectron Spectroscopy and Gas Cluster Sputtering:

X-ray photoelectron measurements were performed in conjunction with gas cluster ion beams, initially developed in the late 90's (Yamada, 1999). The principle for sputtering with individual Ar atoms has been well described (Yamada et al., 2001). Gas cluster ion sputtering (GCIS) is particularly attractive to gently remove the top layers of fragile organic materials. (Seah et al., 2015; Chernysh et al., 2015 and Cristaudo et al., 2014) It has been used in conjunction with XPS to explore the depth distribution of atoms (Yun et al., 2015). When standard Ar+ sputtering is used (~1 keV/Ar_+ ion), there is considerable perturbation of the MOF with substantial preferential removal of O and C relative to Ni, which makes it impossible to determine the location of EDA. Therefore, Ar gas cluster ion sputtering (GCIS) is used in removing the surface EDA molecules on MOFs sample. A large cluster (~2500 Ar atoms) is generated and charged by removal of 1 electron, then accelerated by a 2.5 keV or 5 keV potential difference. Upon impact, the kinetic energy of the cluster is distributed among all Ar atoms (i.e. ~1 or 2 eV per atom), which is insufficient to penetrate into the metal organic framework, limiting the sputtering to surface species only. All the data were recorded with charge compensation. For XPS measurements, the MOFs pellet used for IR measurements is taped on the puck with double sided tape. A Al kα monochromated source is used with a beam size of 200×200 $\mu m^2$. Spectra are recorded at a 450 takeoff angle with respect to the surface. the bombarded area is 1×1 $mm^2$, and the sample is rotated at a rate of 0.2 rpm for 5 to 15 minute and then 0.5 rpm for 2 minute in order to achieve a uniform sputtering. The base pressure is typically below $4\times10^{-8}$ Pa and the Ar pressure during the sputtering is $2\times10^{-6}$ Torr.

Low Energy Ion Scattering:

LEIS measurements are performed using a Qtac analyzer (IonTOF Gmbh, Minster, Germany) using 3 keV $He^+$ and 5 keV $Ne^+$ as the probe and sputtering ions, respectively. The $He^+$ current used for the measurements is approximately 4 nA, and the $Ne^+$ sputtering current is approximately 11 nA. The instrument employs a double-toroidal analyzer that collects all ions scattered within an angular range of 144-146° and images them according to their energy onto a position sensitive detector. Samples for LEIS are prepared by pressing the EDA-pretreated MOF powders into a tungsten mesh and mounting the mesh onto an $SiO_2$/Si wafer. A 1.5×1.5 $mm^2$ sample area is analyzed. Ne+ sputtering is performed using the LEIS ion gun, and thus the ions impinge at normal incidence on the sample, unlike the conventional 45° sputtering geometry.

Ab Initio Calculations:

Ab initio calculations are performed at the density functional theory (DFT) level, as implemented in the Quantum Espresso (Paolo et al., 2009). In order to correctly capture the crucial van der Waals interaction between the MOF and the guest molecules, the non-local functional vdW-DF was used (Thonhauser et al., 2015; Langreth et al., 2009; Thonhauser et al., 2007 and Berland et al., 2015. Ultra-soft pseudopotentials are used with cutoffs of 544 eV and 5440 eV for the wave functions and charge density, respectively. Due to the large dimensions of the unit cell, only the T-point is sampled. To model the diffussion process we use a transition-state search algorithm, i.e. the climbing-image nudged-elastic band method (Henkelman and Jónsson, 2000 and Henkelman, 2000). This method is chosen because it finds the lowest-energy pathway between an initial and final state, which may well deviate from a straight line (i.e. linear interpolation) between the two. Furthermore, this method allows us to obtain a clear picture of the interaction between the CO molecule and the EDA molecules blocking the pores, which cannot easily be obtained by other methods such as ab-initio molecular dynamics. It was started from the experimental rhombohedral structure of Ni-MOF-74 with 54 atoms in its primitive cell and space group $R\overline{3}$. The description through hexagonal axes is a=b=25.719 Å and c=6.741 Å, (20) and α=β=90° and γ=1200. All atomic positions were optimize until the forces are less than $2.6\times10^{-4}$ eV/Å.

Example 2—Discussion

In situ IR spectroscopy, (Nijem et al., 2010; Nour et al., 2012 and Garrone, 2005) which is well-suited to determine absolute gas loading, (Garrone, 2005) was used to demonstrate that post-exposure of MOF-74 crystals to "sticky" molecule ethylenediamine (EDA) vapors is very effective in trapping weakly bound small gas molecules (CO, $CO_2$, $SO_2$, $C_2H_4$) within the material, or to prevent their loading into an EDA-capped empty MOF. A combination of X-ray photoelectron spectroscopy with gas cluster ion sputtering and low energy ion spectroscopy measurements establish that EDA is only adsorbed as a monolayer on the exterior surface of MOF crystals (<1 nm thick), i.e. within the outermost pores of the microcrystals, capping molecules within the bulk of MOFs. Without wishing to be bound by any theory, it is believe that the ab initio modeling provides an explanation for this observation and proposes a structure that accounts for the observed properties. Interestingly, this EDA barrier is transparent to water molecules that readily diffuse through it and remove pre-adsorbed molecules (e.g., CO). Ab initio modeling attributes such a "gate opening" to the disruption of the H-bonded amine groups of EDA by water molecules.

EDA molecules were selected since they contain terminal amine groups, which are known to interact more strongly with a variety of MOFs, particularly those with open or unsaturated metal sites (e.g. found in MOF-74) by forming metal-amine complexes (Choi, 2012; McDonald et al., 2012 and Hwang et al., 2008). Moreover, previous studies have shown that EDA molecules cannot easily penetrate into MOFs due to their size and strong interaction with the framework, requiring refluxing in solution (e.g. anhydrous toluene) (Choi, 2012; Lee et al., 2014 and Andirova, et al., 2015). For instance, in Mg-MOF-74, i.e. $Mg_2$(dobdc) with dobdc=2,5-dihydroxybenzene dicarboxylic acid, the best attempts only lead to ~0.13 EDA per $Mg^{2+}$ metal center, which is an order of magnitude less than theoretically possible (Choi, 2012 and Andirova, et al., 2015). By highlighting the difficulty to fully load EDA in MOF-74, these pioneering studies suggest that, without extensive refluxing, EDA molecules should only adsorb on the surface of MOF crystals. MOF-74 has a three-dimensional honeycomb lattice with one-dimensional channels (diameter ~14 Å, FIG. 1) and contains a high density of coordinatively unsaturated metal sites, which are the highest binding energy site for small molecules such as $CO_2$, NO, $SO_2$, $CH_4$ and $H_2$ (Dietzel et al., 2008; Wu et al., 2009; Liu et al., 2008; Tan et al., 2015 and Bonino et al., 2008) Therefore, in this system the only diffusion pathway for small molecules is through the channel (Canepa et al., 2013). Consequently, it was hypothesized that post-exposure of MOF-74 to EDA after gas loading generates a barrier layer and prevents escape of the gas.

The initial focus of these studies have been on CO adsorption in Ni-MOF-74 because CO is a good probe of Lewis acid adsorption sites and sensitive to the local cationic environment (Vimont et al., 2006 and Hadjiivanov et al., 2002). Furthermore, the stretch frequencies [ν(CO)] of adsorbed and gas-phase species are easily distinguishable. Moreover, the CO binding energy is higher in Ni-MOF-74 (~52.7 kJ/mol determined by isotherm (Bloch et al., 2014)) than in other isostructural frameworks with M=Mg, Mn, Fe, Co, and Zn (Bloch et al., 2014). In all frameworks, the isotherms are fully reversible at room temperature, consistent with weak binding with uncoordinated metal sites through electrostatic, σ and π orbital interactions (Bloch et al., 2014).

Figure 2:
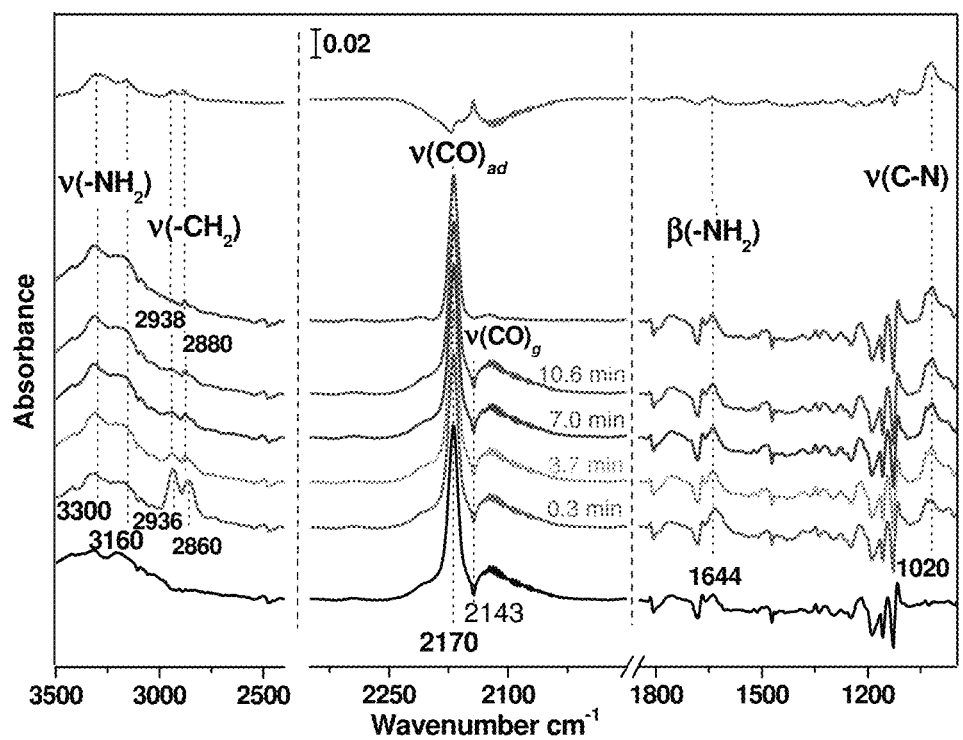
FIG. 2 shows the evolution of infrared spectra of preloaded CO molecules in Ni-MOF-74 after introducing a gas mixture of CO and EDA (~40 Torr CO/~4 Torr EDA). The bottom black spectrum shows the pure CO adsorption after an equilibrium of ~30 min. The middle five spectra show the time dependence features after introducing mixture of CO+EDA for ~10 min and subsequent evacuation within ~10 sec (pink). All the spectra are referenced to the activated MOFs in vacuum except for the top differential spectrum, which is obtained by subtracting the spectra after evacuating mixture gas phase of CO and EDA (pink) and before loading EDA (black).

After activation and CO loading (~40 Torr), the ν(CO) band is first observed at 2174 $cm^{-1}$, then shifts to 2170 $cm^{-1}$ as saturation is reached (~30 min); (Bloch et al., 2014 and Chavan et al., 2009) in both cases it remains clearly distinct from the gas-phase band centered at 2143 $cm^{-1}$ (FIG. 2). The main shift is attributed to the formation of a $Ni^{2+}$ . . . CO adduct within the open metal site (Chavan et al., 2009). The coverage dependent shift (~4 $cm^{-1}$) is attributed to additional CO—CO lateral interaction and/or potential slight structural rearrangement of the metal-adduct as the loading increases (Nour et al., 2012; Bonino et al., 2008 and Chavan et al., 2009. The occupation reaches ~0.7 molecules per metal site at ~40 Torr (Bloch et al., 2014). Upon evacuation (pressure <20 mTorr), CO is removed within ~30 min as shown in the red curve in FIG. 3.

If immediately upon evacuation (<~3 sec) a CO/EDA gas mixture (~40 Torr/~4 Torr) is introduced into the cell (when >~95% CO is still trapped) and kept for ~10 min, the intensity of the CO band remains constant (FIG. 2). Furthermore, when the system is evacuated (pressure <20 mTorr), the CO band decreases by less than 3% after a two-hour evacuation, as shown in the black line of FIG. 3. These data unambiguously show that CO can be trapped by introduction of EDA vapor, without hindering the total MOF capacity for CO adsorption.

Detailed information about the nature of the EDA is obtained in the IR absorption spectrum (FIG. 2): on one hand, the two strong $v_{as,s}$(—$CH_2$) vibrational peaks at 2936 and 2860 $cm^{-1}$ indicate that gas-phase EDA is clearly present in the CO/EDA mixture, although they quickly disappear as EDA molecules are adsorbed onto the MOFs and the cell internal walls. On the other hand, evidence for adsorbed EDA on or into MOF-74 is provided by a distinct absorption peak at 1020 $cm^{-1}$ (FIG. 3), corresponding to the ν(C—N) mode of the amine-metal complex (Chopra et al., 2015). This peak increases very slowly during ~10 min as EDA adsorbs on the sample.

The stretch mode of initially adsorbed CO gas (2170 $cm^{-1}$) does not decrease or shift during and after EDA loading, as would typically occur during co-adsorption of gases inside the MOF (FIG. 4 for the case of $NH_3$ co-adsorption), indicating that the CO molecules not only remain trapped, but also do not interact with the newly added EDA molecules. This observation supports the hypothesis that no EDA molecules penetrate inside the MOF. If EDA interacted with CO inside MOF-74, the CO stretch frequency would be shifted either due to displacement to a secondary binding site or to interaction with EDA. To quantify this point, ab initio calculations were performed (FIG. 5 and Table 1) and show that, if EDA penetrated inside the MOF, the CO binding energy would be changed only by ~3 kJ/mol and its frequency would be shifted by 5-9 $cm^{-1}$, which is not observed.

TABLE 1

Figure 5:
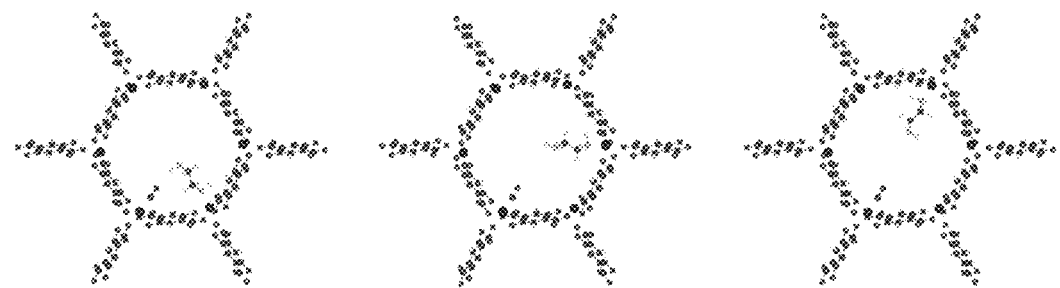
FIG. 5 shows the co-adsorption of CO and EDA at the metal centers of the Ni-MOF-74 system. Left, middle, and right hand side panels show the adsorption of these two molecules as first, second, and third neighbors, respectively. Blue, grey, red, and white spheres represent Ni, C, O, and H atoms, respectively.

Frequencies ($cm^{-1}$) and binding energies (kJ/mol) of CO molecule co-adsorbed with EDA in Ni-MOF-74 (FIG. 5).

|  | CO alone | CO in state i | CO in state ii | CO in state iii |
|---|---|---|---|---|
| ν(C—O) frequencies $cm^{-1}$ | 2129 | 2121 | 2134 | 2138 |
| Binding energies kJ/mol | 51.1 | 52.4 | 53.3 | 49.3 |

The above observations and analyses led to the conclusion that pre-adsorbed CO and post-loaded EDA molecules are spatially separated, with EDA residing on the periphery of the MOF microcrystals (after replacing CO molecules in the outermost pores, since the EDA $E_{binding}$=125 kJ/mol>>CO $E_{binding}$=52.7 kJ/mol) and acting as a cap that confines pre-loaded CO molecules inside the MOF. However, a direct experimental confirmation of EDA localization is needed.

Figures 6A, 6B, 6C:
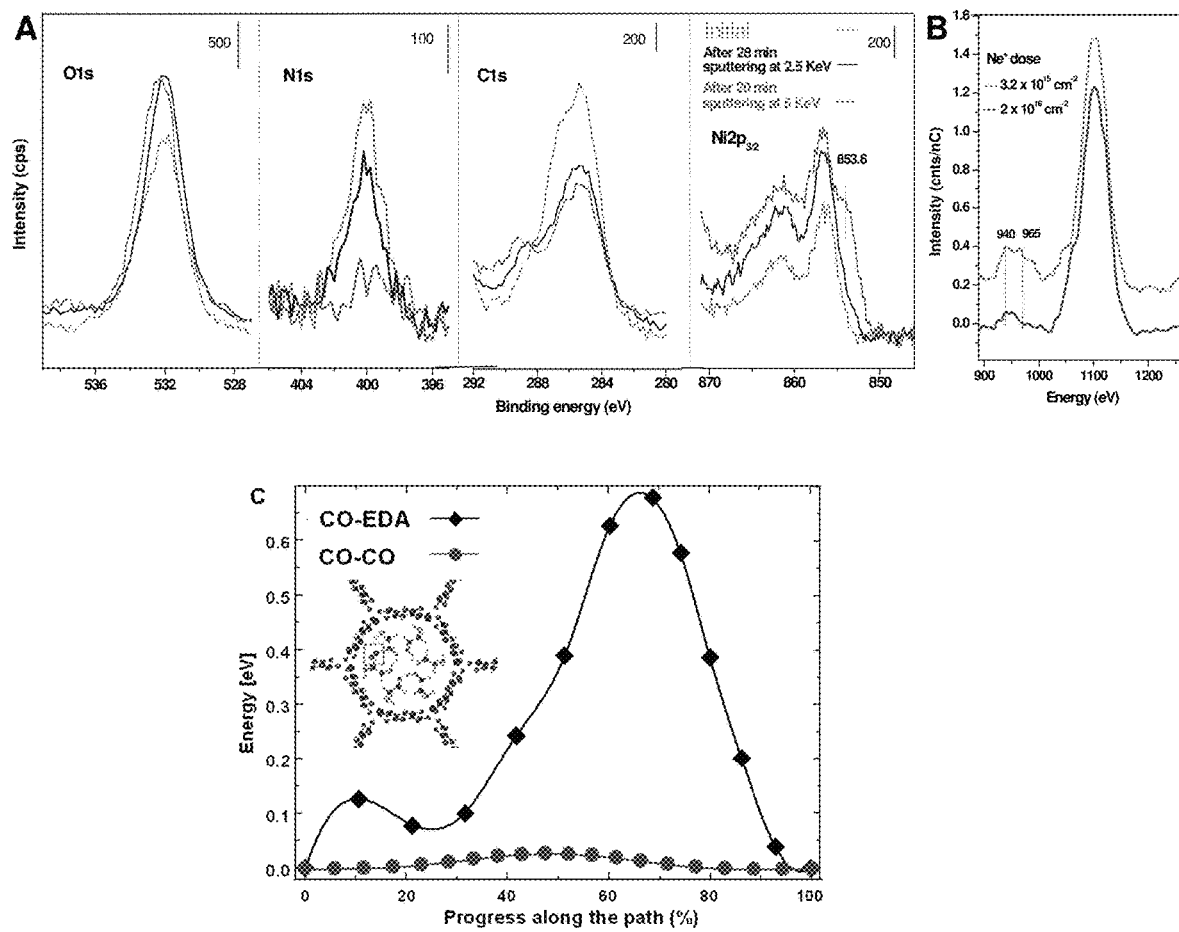
FIGS. 6A-6C shows (FIG. 6A) XPS spectra of Ni-MOF-74 with post-loaded EDA, before (orange curve) and after being sputtered at 2.5 keV for 28 min (blue curve) and 5 keV for 20 min (dark green curve).
Figure 7:
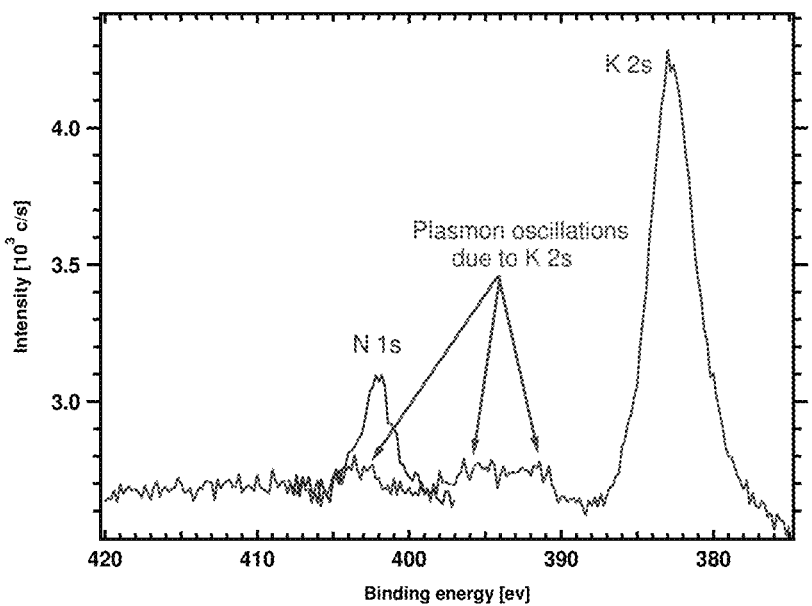
FIG. 7 shows the XPS spectra of blank KBr without MOF sample.

To test and quantify whether EDA is localized at the surface (e.g. only the outmost pores) of the MOF crystallites, combined X-ray photoelectron spectroscopy (XPS), a surface sensitive technique, with argon gas cluster ion sputtering (GCIS) that provides gentle removal of surface atoms (particularly appropriate for organic materials) were used. Specifically, clusters of ~2500 Ar atoms can be generated and charged, then accelerated onto the surface (e.g. with 2.5 to 5 keV). Upon reaching the surface, the cluster decomposes, dividing its kinetic energy among all the Ar atoms, e.g. each atom carries ~1 to 2 eV kinetic energy. Consequently, these atoms can only remove surface atoms and do not disturb underlying bulk atoms of the rather fragile MOF structure (Seah et al., 2015). After each sputtering cycle, XPS data ($Ni2p_{3/2}$, C1s, N1s, and O1s peaks) are recorded on the sample post-loaded with EDA right after the gas exposure measurement (orange line in FIG. 6A) and after sputtering at 2.5 keV for 28 min (blue line in FIG. 6A), and 5 keV for 20 min (brown line in FIG. 6A). Since the MOF contains only O, Ni, and C atoms, a comparison of the N1s core level (N is only contained in EDA) with O1s, $Ni2p_{3/2}$, and C1s, provides information on the depth distribution of EDA. While sputtering at 2.5 keV (~1 eV/Ar atom) for 28 min only partially removes EDA (N1s signal), sputtering with 5 keV (~2 eV/Ar atom) for 20 min fully removes nitrogen. The remaining minor feature in the $N_1s$ spectral region is due to plasmon oscillations of K2s of the KBr substrate (FIG. 7). The oxygen and Ni signals remain essentially unchanged. The initial decrease of the C signal is associated with the removal of adventitious hydrocarbons physisorbed on the MOF surface. Note that the intensities of N, O, and Ni increase slightly after the initial sputtering as screening by adventitious carbon is removed. Thereafter, the C1s, O1s and Ni2p$_{3/2}$ signals remain constant. The shoulder at 853.6 eV in the Ni2p$_{3/2}$ peak after removal of EDA is tentatively attributed to surface reconstruction of the Ni corner atoms due to displacement (perturbation) of surface atoms. Importantly, all the above observations clearly point to the localization of EDA at the periphery (surface region) of the MOF microcrystals.

To further verify the localization of EDA at the periphery of the microcrystals, low energy ion scattering (LEIS) measurements of EDA-pretreated MOF powders were performed. The ultra-shallow penetration depth of this technique (~1 nm) makes it particularly sensitive to elements at the surface. The spectra are recorded with 3 keV He$^+$ ions, and sputtering is performed with 5 keV Ne$^+$ ions. FIG. 6B shows that, after removing adventitious carbon with a dose of $3.2 \times 10^{15}/cm^2$ Ne$^+$ ions, there is a clear peak associated with N at ~950 eV in addition to the O peak at 1100 eV. The N peak has two components: a surface peak at 960 eV and a subsurface peak at 940 eV, the latter being attributed to EDA at grain boundaries or on tilted surfaces. The surface peak completely disappears after a dose of $2.2 \times 10^{16}/cm^2$ Ne$^+$ ions, confirming that it is located only at the surface well within 1 nm. Additional sputtering does not appreciably change the relative intensity of the N signature, confirming that it originates from EDA at grain boundaries or tilted surfaces. Together, the XPS and LEIS measurements indicate that EDA forms a monolayer (<1 nm thick) at the surface of the MOF micro-crystals.

Figure 8:
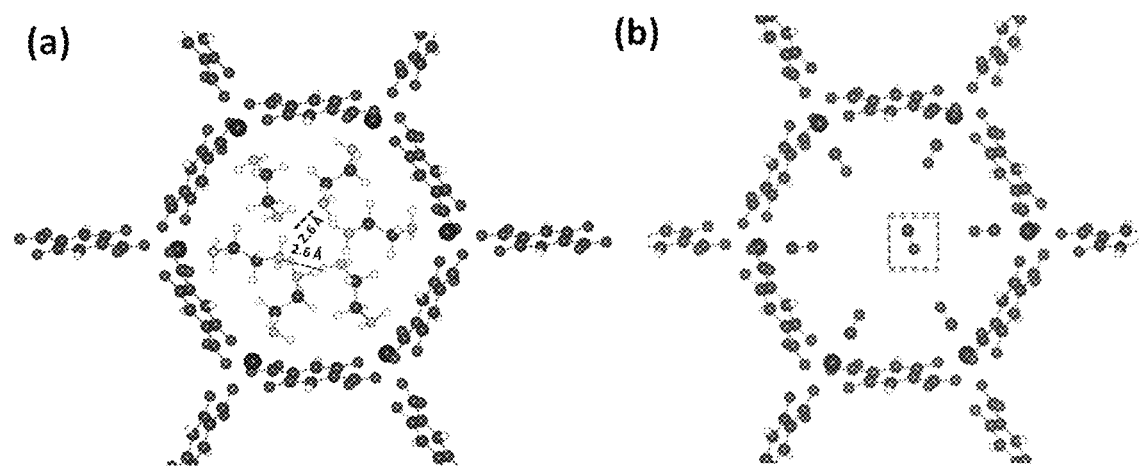
FIG. 8 shows the relaxed atomic position of the Ni-MOF-74 channel where all the adsorption metal cites have been saturated with EDA (a) and CO molecules (b). The dashed red box shows the CO molecule. Black, red, white, grey, and blue spheres represent C, O, H, N, and Ni atoms, respectively.

This knowledge makes it possible to model the EDA arrangement within the Ni-MOF-74 unit cell using ab initio calculations. It was found that the structure shown in FIG. 8A is the most stable and that the binding energy per EDA molecule increases from 125 kJ/mol for ~0.17 EDA per Ni$^{2+}$ (1 EDA per unit cell) to 141 kJ/mol for 1 EDA per Ni$^{2+}$ (1 EDA per metal center, i.e. saturation). This stabilization of aggregated EDA molecules arises from H bonding of the head amine groups (e.g. those pointing to the center of the unit cell, not strongly bonded to the metal centers), as detailed in FIG. 8A. These findings are consistent with previous ab initio calculations performed in Mg-MOF-74 in which the binding energy was found to increase monotonically with loading from 95 kJ/mol at ~0.17 EDA per Mg$^{2+}$ to 125 kJ/mol 1 EDA per Mg$^{2+}$ (Choi, 2012). There is thus a significant energy benefit to form a complete layer due to EDA clustering and it was conclude that a full EDA layer is completed within the first unit cell of the MOF. Once the top surface (<1 nm) is sealed with a complete layer, further EDA diffusion is not possible due to severe steric constraints. The diffusion of the CO molecules was further model through the longitudinal channels of Ni-MOF-74, as described in FIG. 9. The results (FIG. 6C) show that the CO diffusion barrier increases from 0.028 eV for a CO-loaded MOF to 0.68 eV for MOF with a monolayer of EDA, i.e. a 24 times increase, which is consistent with the experimental observations.

Figure 3:
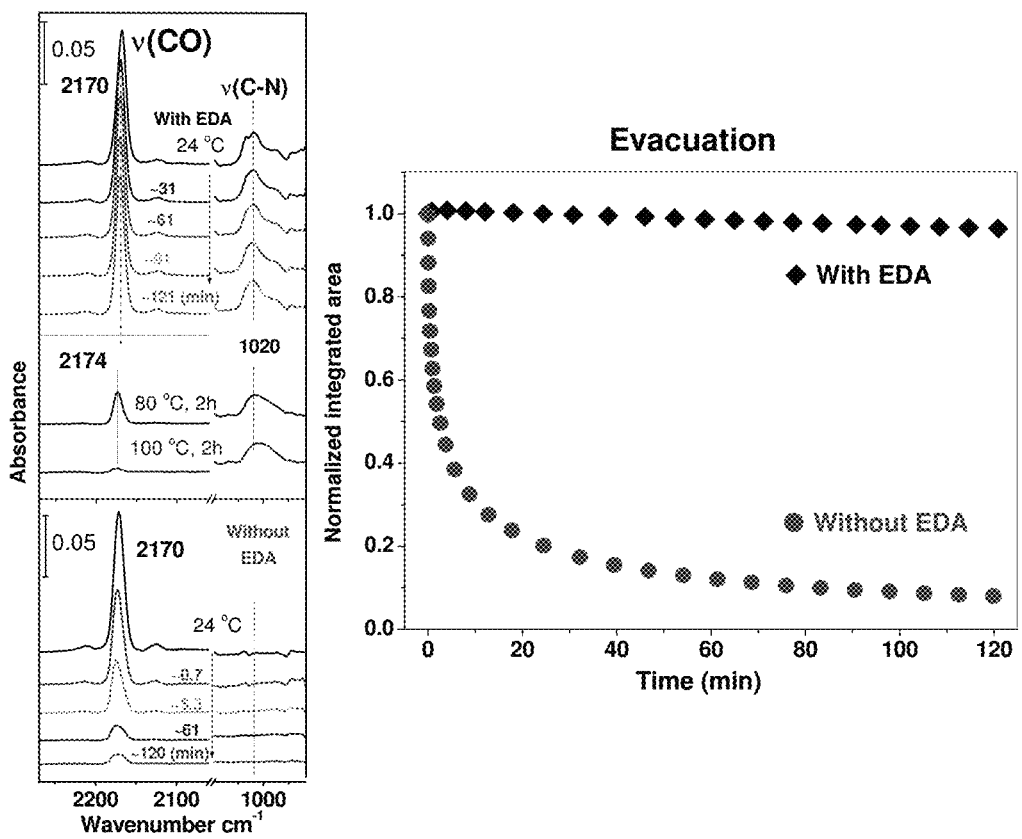
FIG. 3 shows the time evolution of the ν(CO) band (2170 $cm^{-1}$) upon evacuation (<20 mTorr) for pristine (red circles) and EDA post-loaded (black diamonds) samples. All spectra are collected at 24° C. and referenced to the pristine activated MOF in vacuum. The annealing sequence includes 2 h at 80° C., cooling back to room temperature for data collection, and an additional 2 h at 100° C., cooling back to room temperature for data collection. The integrated areas are normalized to their maximum value obtained at t=0 (top spectrum). The error bars are calculated from the variations in the measured (normalized) integrated areas and do not exceed 0.02.
Figure 10:
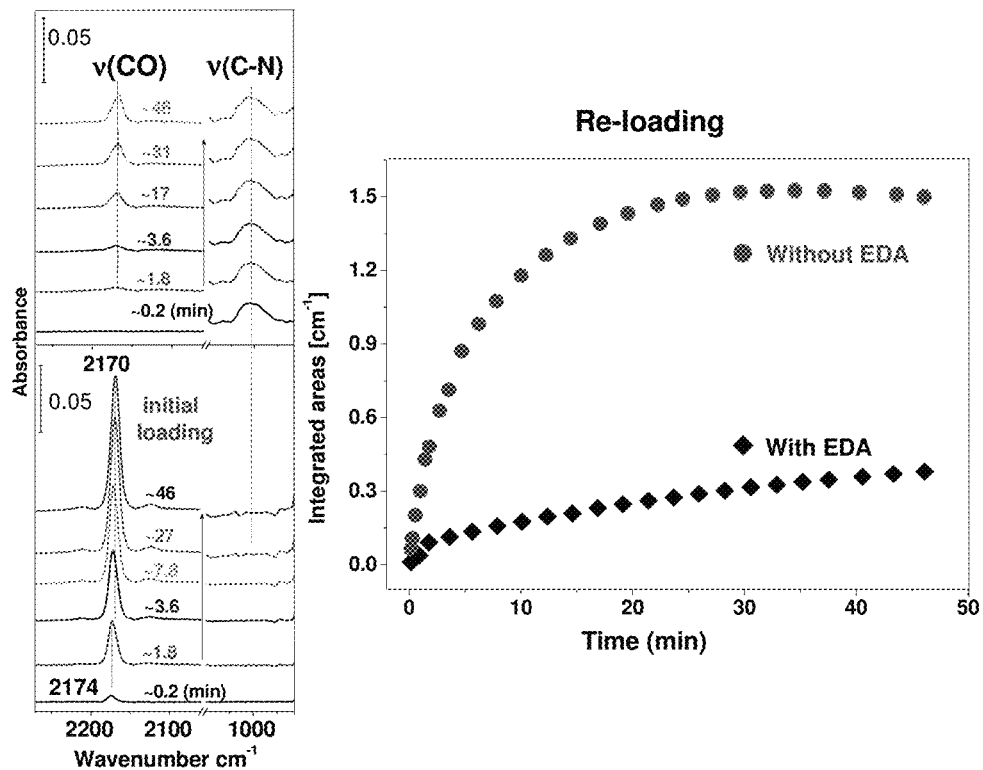
FIG. 10 shows the time evolution of the $\nu(CO)$ band upon reloading in ~40 Torr CO in the pristine MOF (without EDA, red circles) and of the same sample after exposure to a CO/EDA mixture and subsequent annealing (FIG. 3). All the spectra are collected at 24° C. and referenced to the pristine activated MOF in vacuum. The CO gas-phase contribution is subtracted from each spectrum and the remaining 3% adsorbed CO after annealing (FIG. 3) is also subtracted from the spectra collected during the reloading.

While CO is clearly trapped at room temperature, the removal of CO can be completed by mild annealing up to 100° C. under vacuum (pressure <20 mTorr) and EDA remains mostly unperturbed (FIG. 3). The effect of EDA on CO re-adsorption can now be examined, using the same loading conditions (~40 Torr). FIG. 10 shows that the CO uptake is dramatically reduced compared to the pristine activated MOF-74 (EDA-free), taking over 45 min to reach only ~25% of the CO loading obtained in pristine MOF-74 loaded in ~30 min.

Figure 12:
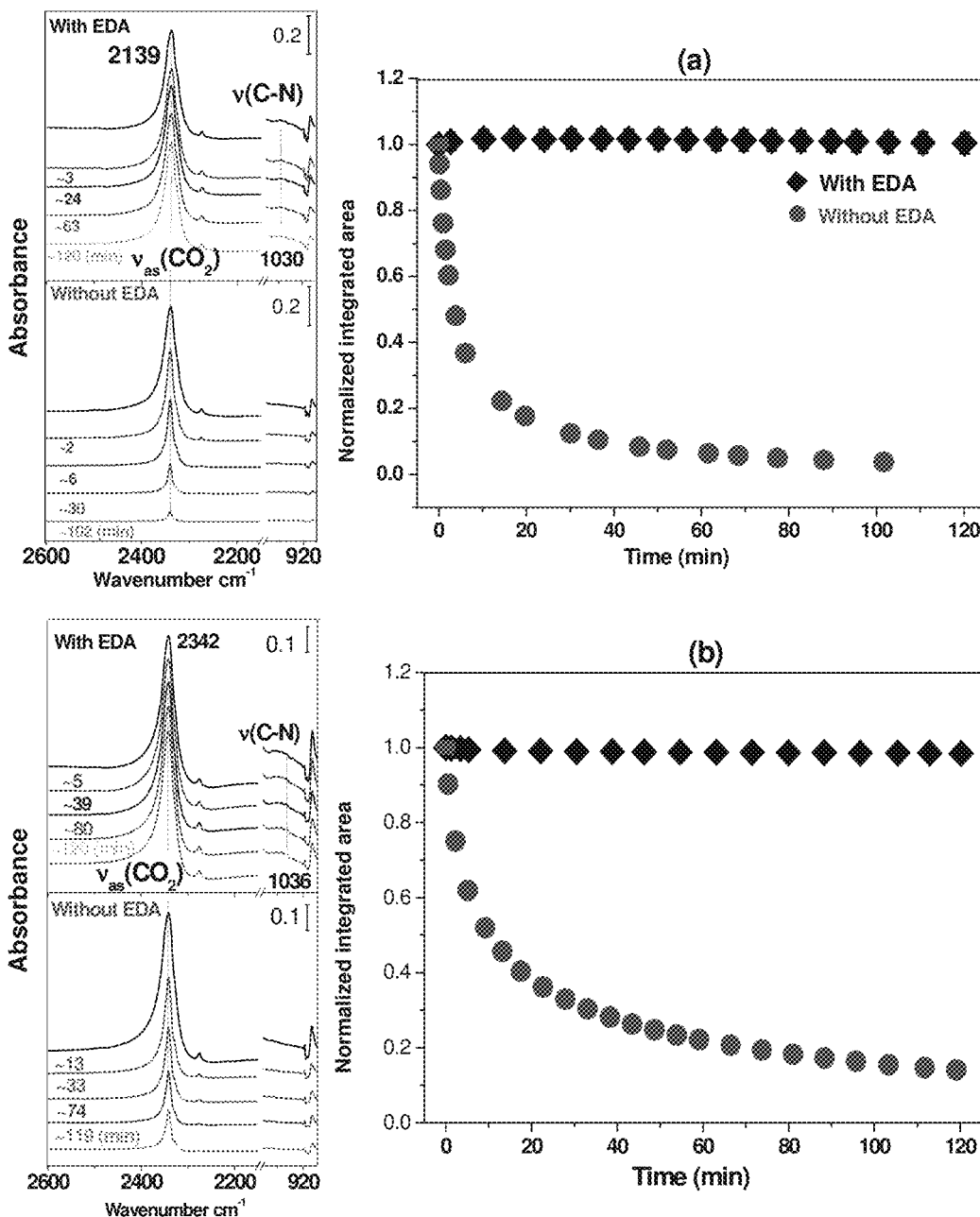
FIG. 12 shows $CO_2$ band evolution upon evacuation in vacuum (<20 mTorr) for Co-MOF-74 (top panel) and Zn-MOF-74 (bottom panel) with post-loaded EDA (black diamonds) and in pristine state (red circles). All the spectra were collected at 24° C. and referenced to the activated MOF in vacuum. The desorption rate was monitored by recording the spectra and the intensity of the $\nu_{as}(CO_2)$ band during desorption. The error bars of normalized area do not exceed 0.03 in both Co, Zn-MOF-74. The procedure for loading $CO_2$+EDA in Zn, Co-MOF-74 was the same as for Ni-MOF-74. The concentrations of $CO_2$ in Zn, Co-MOF-74 under ~80 Torr $CO_2$ were estimated to be 0.21 and 0.44, respectively. (Yazaydin, et al., 2009)
Figures 13A, 13B, 13C:
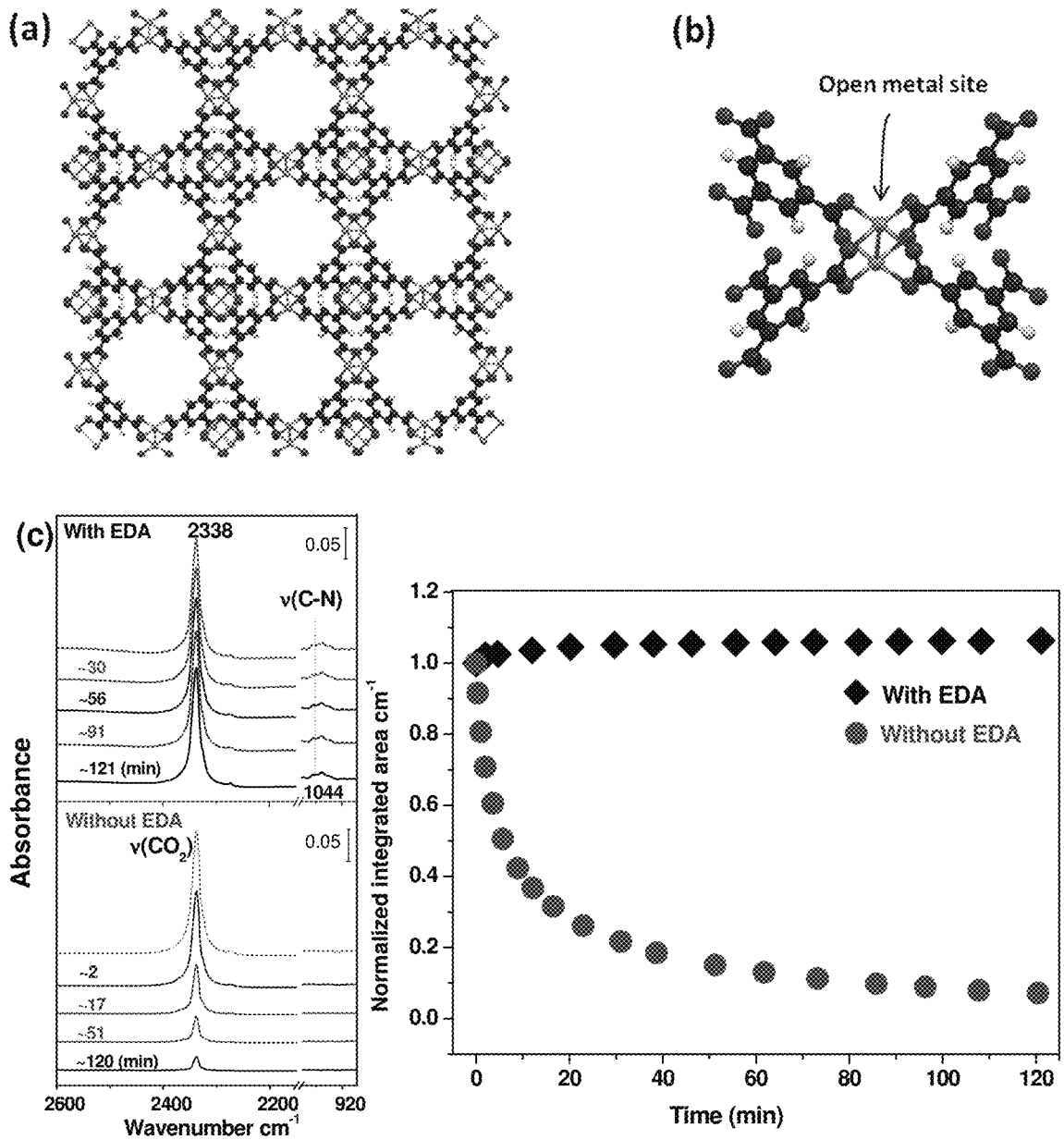
FIGS. 13A-13C show (FIG. 13A) Top view along the [100] direction of the cubic cell of MOF HKUST-1 and (FIG. 13B) the dicopper(II) tetracarboxylate building block. Color scheme: light blue, grey, red, and white spheres represent Cu, C, O, and H atoms respectively. HKUST-1, also called Cu(BTC) (BTC=benzenetricarboxylic acid), has face a centered-cubic crystalline structure and contains an intersecting three-dimensional (3D) system of large square-shaped pores (9 Å×9 Å). The solvent free structure is composed of paddlewheel dimeric cupric tetracarboxylate units (FIG. 13C), in which each copper atom is coordinated by four oxygen atoms, coming from the benzene tricarboxylic acid linkers. (Chui, et al., 1999) The terminal water molecules in the apical sites of the Cu—Cu dimer can be removed by thermal activation, offering coordinative binding vacancies (open metal sites) to the guest molecules such as EDA, $CO_2$ and NO. The heat of adsorption $CO_2$ in HKUST-1, derived from temperature dependent isotherms, is 35 kj/mol. (Wang, et al., 2002) (FIG. 13C) $\nu(CO_2)$ band evolution upon evacuation in vacuum (<20 mTorr) for HKUST-1 with (black diamonds) and without (red circles) post-loaded EDA. All the spectra were collected at 24° C. and referenced to the activated MOF in vacuum. The error bars of normalized integrated areas do not exceed 0.03. The loading procedure of $CO_2$+EDA (~80 Torr+~4 Torr) in HKUST-1 is the same as that in MOF-74. The uptake of $CO_2$ within HKUST-1 sample around ~80 Torr is measured to be 27.3 mg/g. (Yazaydin, et al., 2009) The coordinatively bonded EDA at the $Cu^{2+}$ site is observed at 1044 $cm^{-1}$, associated with the $\nu(C-N)$ mode.
Figure 14:
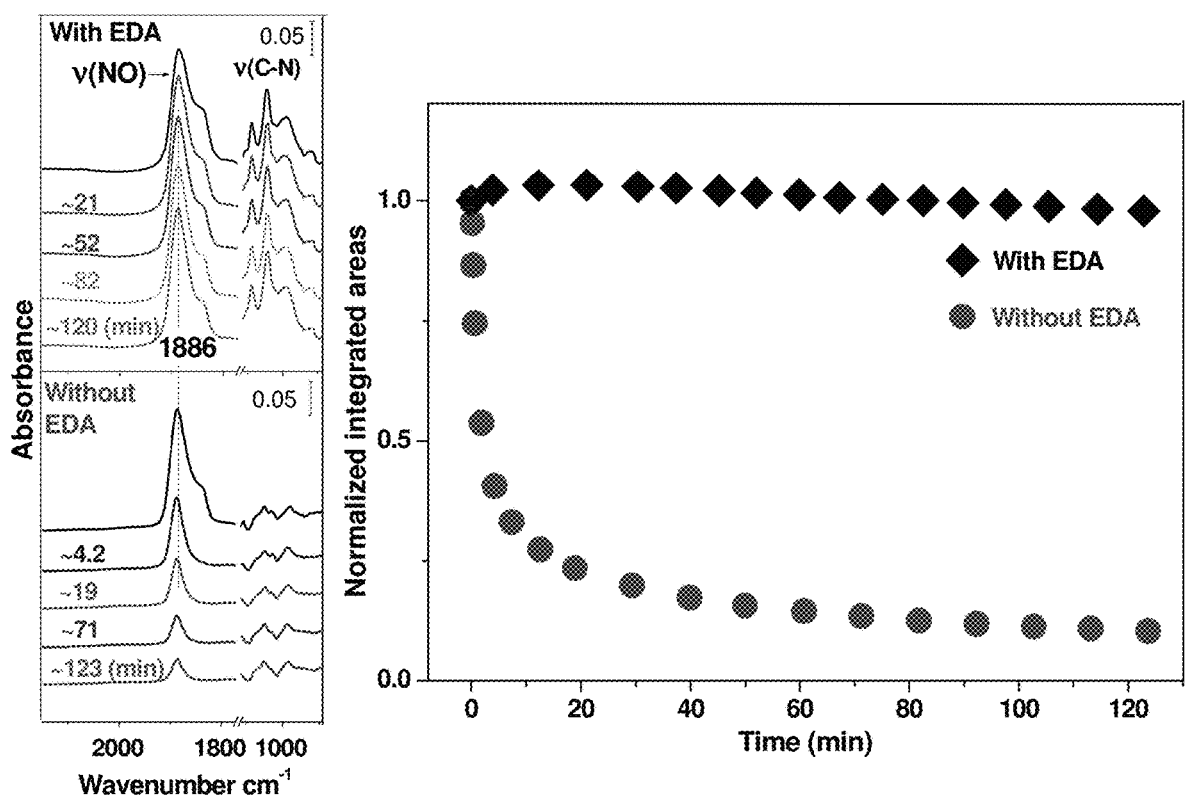
FIG. 14 shows NO band (stretching $\nu$) evolution upon evacuation in vacuum (<20 mTorr) for HKUST-1 with (black diamonds) and without (red circles) post-loaded EDA. All the spectra were collected at 24° C. and referenced to the activated MOF in vacuum. The desorption rate was monitored by recording the spectra and the intensity of the $\nu(NO)$ band during desorption. The error bars of normalized integrated areas for $\nu(NO)$ do not exceed 0.02. The loading sequence of NO+EDA (~1000 Torr+~4 Torr) in HKUST-1 sample is the same as for other molecules in MOF-74 samples. The adsorption uptake of NO in HKUST-1 is over 3 mmol/g at 298 K, determined by isotherm measurements in (Xiao, et al., 2007) and by the observed frequency of $\nu(NO)$, based on the literature (Xiao, et al., 2007).

To test whether EDA acts as a cap in general, this method was used with other small molecules ($CO_2$, $SO_2$, and $C_2H_4$) that are also weakly bonded in MOF-74 and rapidly diffuse out at room temperature. As shown in FIG. 11 for Ni-MOF-74 and FIG. 12 for Zn,Co-MOF-74, we find that EDA again provides an effective barrier to retain those molecules. Furthermore, the same method was successfully applied to other MOFs structure such as HKUST-1 (Chui et al., 1999) (FIGS. 13 & 14) to trap $CO_2$ and NO, the latter being an active biological molecule (Cohen, 2012).

Figures 15A, 15B, 15C:
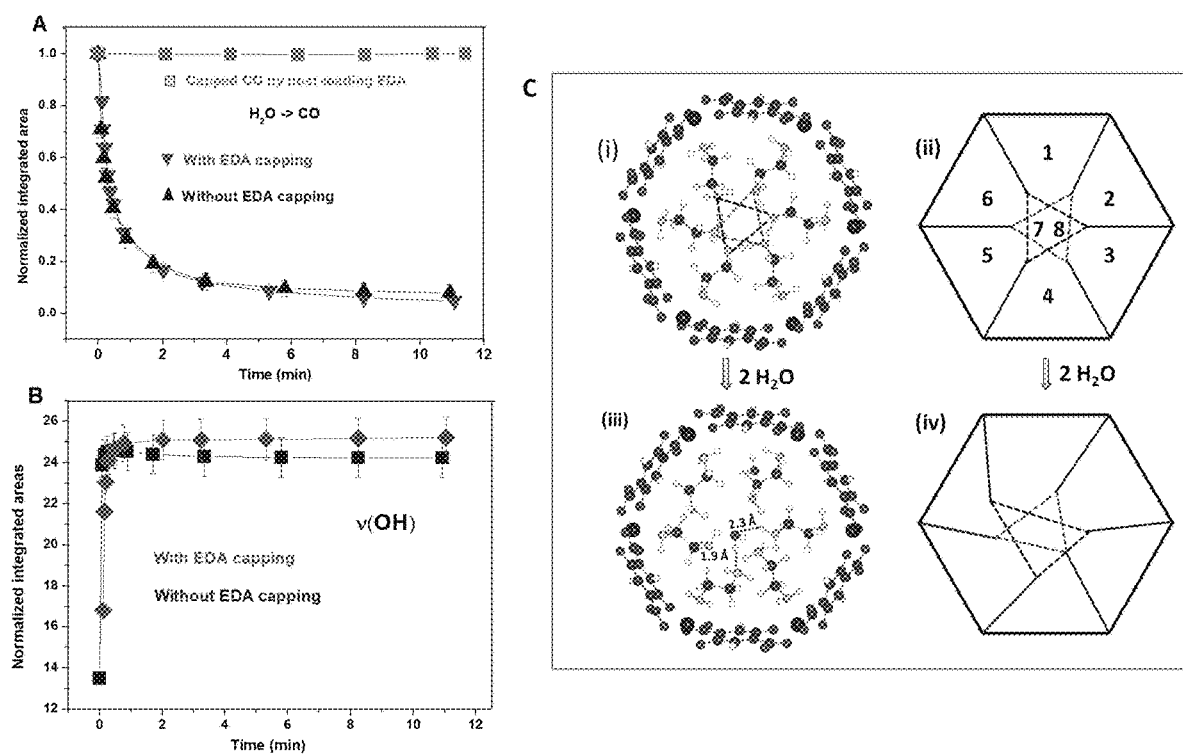
FIGS. 15A-15C show time evolution of the intensities of the (FIG. 15A) $\nu(CO)$ and (FIG. 15B) $\nu(H_2O)$ bands in capped Ni-MOF-74 in the presence of 8 Torr $H_2O$ vapor. The error bar of the sharp $\nu(CO)$ band in panel (FIG. 15A) does not exceed 0.04 and the error bar of the $\nu(H_2O)$ broad band in panel (FIG. 15B) is larger due to uncertainties in determining the baseline in the difference spectra (FIG. 16).
Figures 16A, 16B:
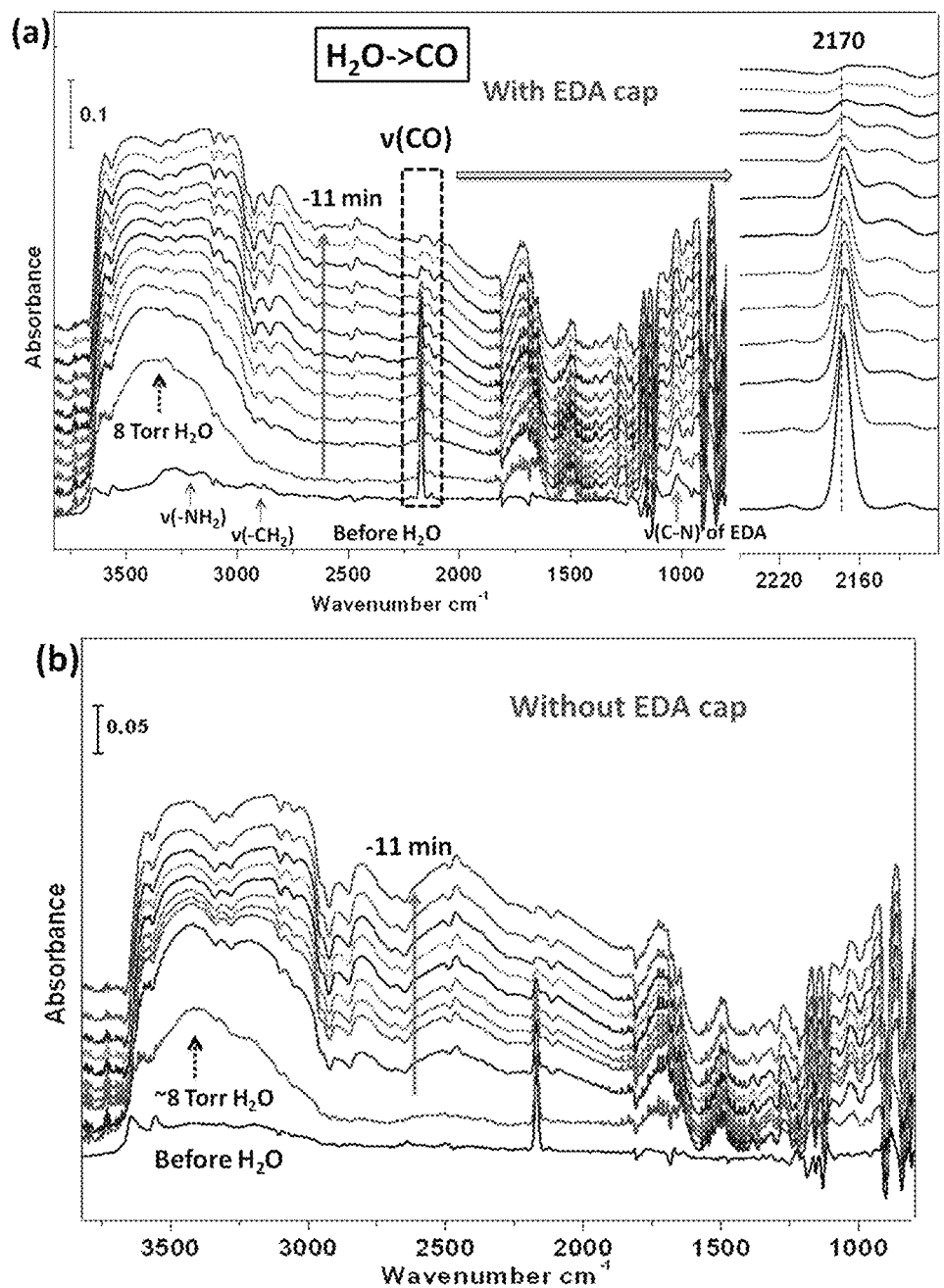
FIGS. 16A & 16B show (FIG. 16A) IR absorption spectra of EDA-capped Ni-MOF-74 samples previously loaded with 40 Torr CO before and after exposure to 8 Torr $H_2O$ referenced to pristine (freshly thermally activated in vacuum, <20 mTorr), as a function of time in 8 Torr water vapor. The broad band above ~2600 $cm^{-1}$ corresponds to adsorbed water and the sharp mode at 2170 $cm^{-1}$ to adsorbed CO.

The most striking result was obtained with water molecules, chosen because they can form hydrogen bonds with amine groups: water was observed to pass through the EDA layer without any hindrance and was able to remove pre-adsorbed CO completely. The experiment was started by capping CO molecules in MOFs under 40 Torr by growing an EDA layer via vapor-phase deposition as shown in FIG. 3. After evacuation for ~1.5 h (e.g. CO still retained), 8 Torr vapor-phase $H_2O$ was introduced into the cell and IR spectra recorded as a function of time. FIGS. 15A & 16 clearly show that the adsorbed CO peak dramatically weakens while the water stretching band $\nu(OH)$ quickly strengthens. Clearly, water molecules diffuse into the MOF channel and force the pre-adsorbed CO molecules out through the EDA layer, still present as evidenced by its characteristics $\nu(C-N)$ band at 1020 cm$^{-1}$. To quantify the rate of water penetration, the same experiment was performed without EDA capping. CO molecules were loaded into Ni-MOF-74 at 40 Torr for ~30 min. Followed by a quick evacuation (<3 sec), 8 Torr $H_2O$ was introduced into the cell (FIG. 16). FIG. 15B shows that there is no measurable difference in the intensity decrease of $\nu(CO)$ and increase of $\nu(H_2O)$ between pristine and EDA-capped MOF, as though the EDA layer did not exist. The dramatically different behavior of water compared to other gases is tentatively attributed to the ability of water to interact with $-NH_2$ through H bonding.

Figure 18:
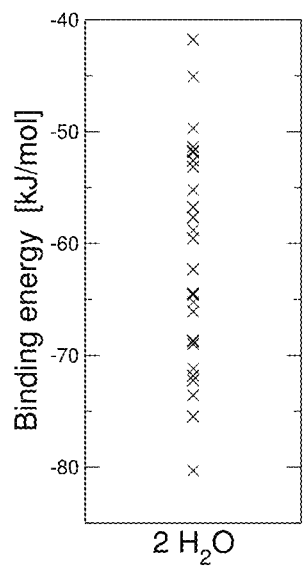
FIG. 18 shows the Binding energy of water molecules in EDA-loaded Ni-MOF-74 for the case of adding 2 $H_2O$ molecules. 28 binding energies are reported, corresponding to all possible ways of adding 2 water molecules to the 8 existing adsorption sites, see FIG. 17.
Figures 19A, 19B, 19C, 19D, 19E:
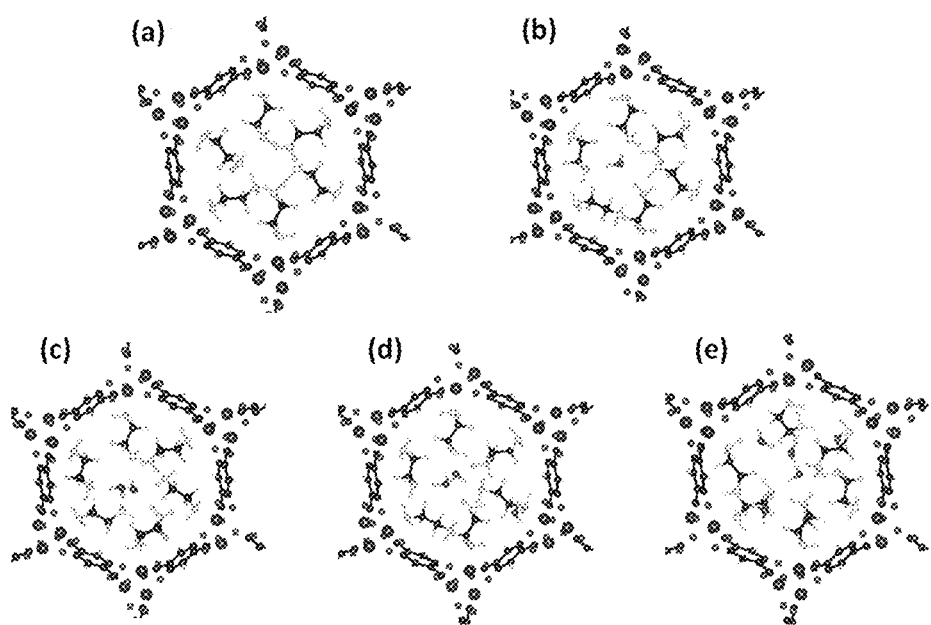
FIGS. 19A-19E show the relaxed atomic position of EDA molecules at the middle of the Ni-MOF-74 channel upon loading $H_2O$ molecule(s).
Figures 20A, 20B:
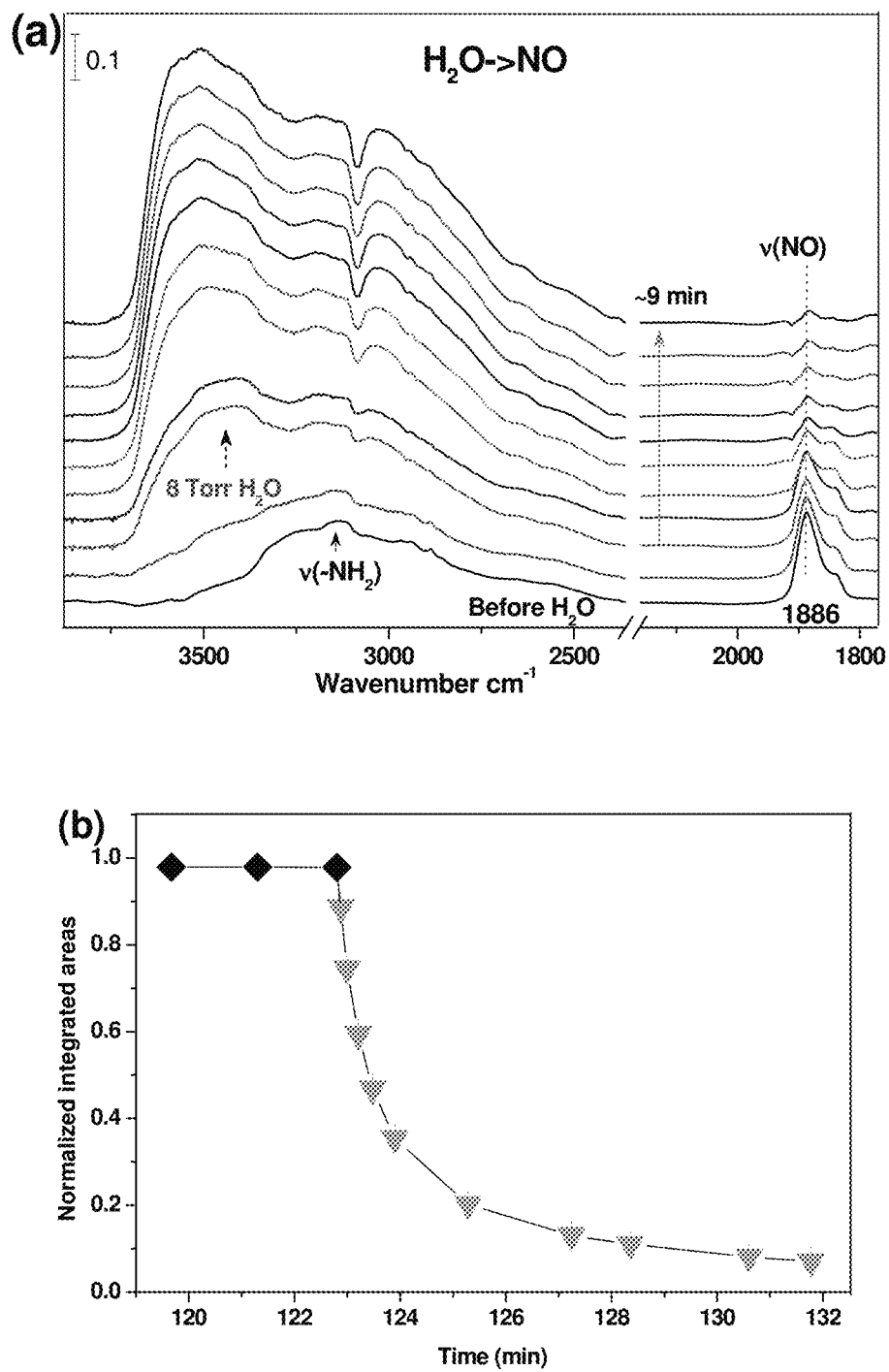
FIGS. 20A & 20B show (FIG. 20A) IR absorption spectra of an EDA-capped HKUST-1 sample previously loaded with ~1000 Torr NO before (FIG. 14) and after exposure to 8 Torr $H_2O$ vapor referenced to pristine (freshly thermally activated in vacuum, <20 mTorr), as a function of time in 8 Torr $H_2O$ vapor. The broad band above ~2500 $cm^{-1}$ corresponds to adsorbed $H_2O$ and the sharp mode at 1886 $cm^{-1}$ to adsorbed NO.

To examine this hypothesis, the perturbation of EDA adsorption geometry was investigated upon adding water molecules by ab initio calculations. When MOF channels are fully loaded with EDA molecules, the $-NH_2$ head groups of the adsorbed EDA molecules point towards the center of the MOF represented as blue lines in the panel ii of FIG. 15C. There are six $-NH_2$ divided into two sets, each one of them making an imaginary triangle with N atoms at the apex in the middle of the channel, see the black and red triangles. These two triangles are located in planes parallel to the page, but not in the same plane. There are 6 adsorption sites for water near the linkers (1 to 6), and 2 in the middle of the channel (7 and 8). It was observed in panels iii and iv of FIG. 15C that the addition of $H_2O$ molecules clearly enlarges the triangles. For instance, two water molecules placed at sites 1 and 7 increase the area of the triangle by tilting the —C—C— and —C—N— bond angles of several EDA molecules away from the center of the channel (FIG. 15Civ) and FIG. 17). These water adsorption states are energetically favorable (FIG. 18) since water molecules establish the hydrogen bonding with $-NH_2$ group, evidenced by the short H ... N or H ... O distance (FIG. 15Ciii). By continually adding water molecules up to 4 and 6, the area of these triangles in most cases becomes significantly larger (FIGS. 17 & 19), enabling water molecules more easily to enter through the channel. This "gate opening mechanism" also works for other MOF structures, leading for instance to the removal of NO molecules from within HKUST-1 by water exposure. (FIG. 20).

Example 3—Additional Examples of Capping Molecules ($CO_2$, NO) within Different MOFs

A. HKUST-1

Figures 21A, 21B, 21C:
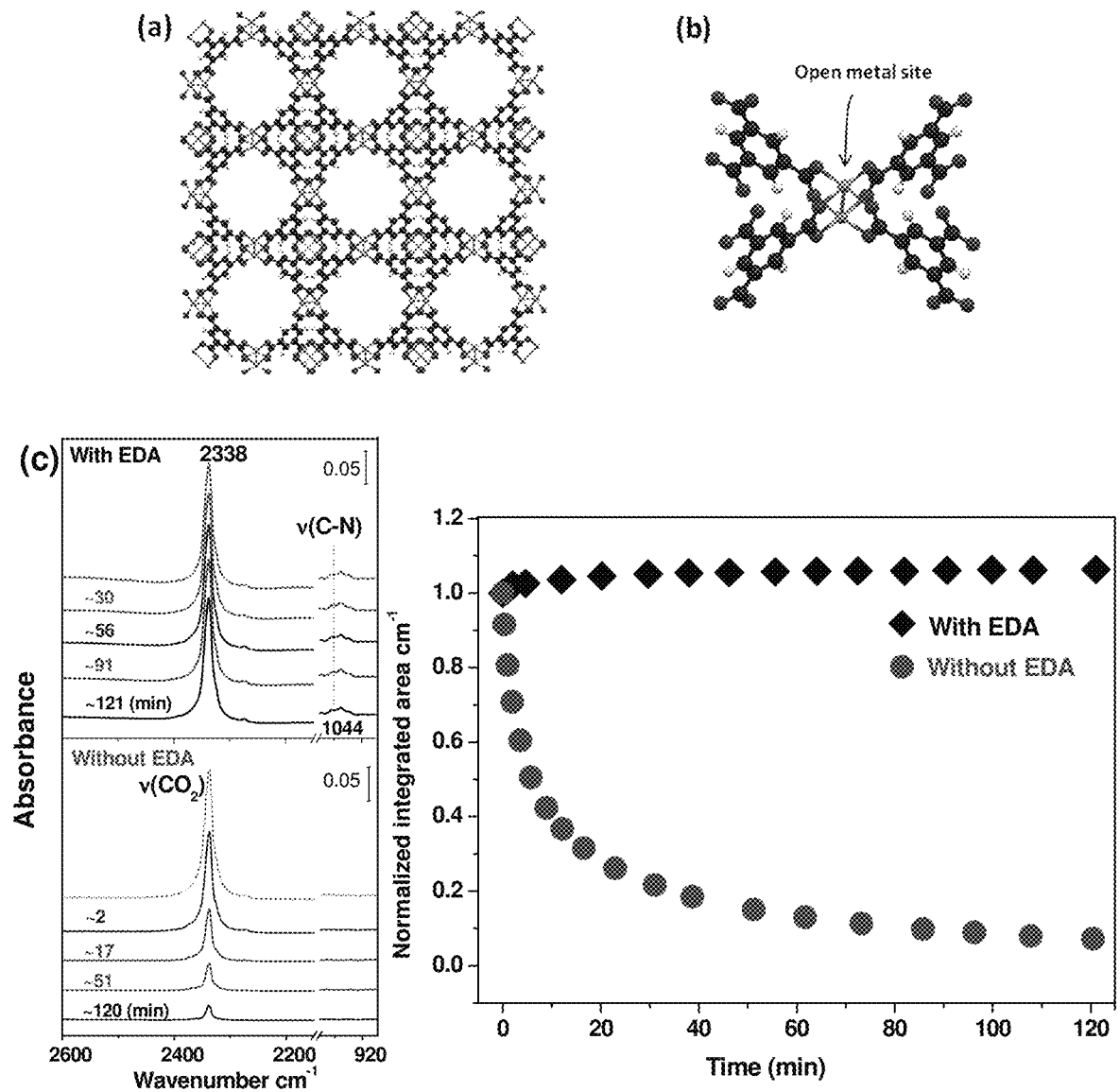
FIGS. 21A-21C show (FIG. 21A) Top view along the [100] direction of the cubic cell of MOF HKUST-1 and (FIG. 21B) the dicopper(II) tetracarboxylate building block. Color scheme: light blue, grey, red, and white spheres represent Cu, C, O, and H atoms respectively.
Figures 22, 23A, 23B:
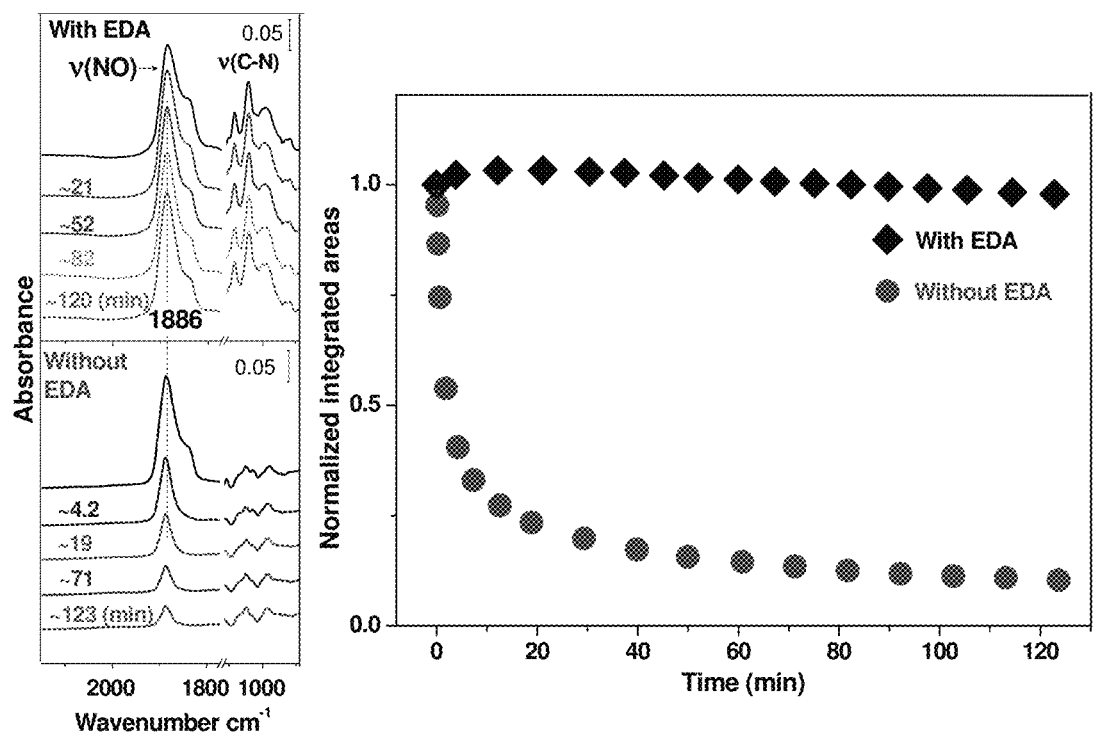
FIG. 22 shows the NO band (stretching ν) evolution upon evacuation in vacuum (<20 mTorr) for HKUST-1 with (black diamonds) and without (red circles) post-loaded EDA. All the spectra were collected at 24° C. and referenced to the activated MOF in vacuum. The desorption rate was monitored by recording the spectra and the intensity of the ν(NO) band during desorption. The error bars of normalized integrated areas for ν(NO) do not exceed 0.02. The loading sequence of NO+EDA (~1000 Torr+~4 Torr) in HKUST-1 sample is the same as for other molecules in MOF-74 samples. The adsorption uptake of NO in HKUST-1 is over 3 mmol/g at 298 K, determined by isotherm measurements in (Xiao et al., 2007) and by the observed frequency of ν(NO), based on the literature (Xiao et al., 2007).
FIGS. 23A & 23B show the structure of trinuclear {$Cr_3O$} building units and bridging benzene-1,4-dicarboxylate ligands form pentagonal and hexagonal rings (FIG. 23A) which are assembled into mesoporous cages (FIG. 23B). The yellow spheres in the mesoporous cages with diameters of 29 or 34 Å, respectively. (water-guest molecules are not shown) (Jeazet et al., 2013).

HKUST-1, also called Cu(BTC) (BTC=benzenetricarboxylic acid), has face a centered-cubic crystalline structure and contains an intersecting three-dimensional (3D) system of large square-shaped pores (9 Å×9 Å). The solvent free structure is composed of paddlewheel dimeric cupric tetracarboxylate units (panel b), in which each copper atom is coordinated by four oxygen atoms, coming from the benzene tricarboxylic acid linkers (Chui et al., 1999). The terminal water molecules in the apical sites of the Cu—Cu dimer can be removed by thermal activation, offering coordinative binding vacancies (open metal sites) to the guest molecules such as EDA, $CO_2$ and NO. The heat of adsorption $CO_2$ in HKUST-1, derived from temperature dependent isotherms, is 35 kj/mol (Min Wang et al., 2002). FIGS. 21 & 22 shows that weakly adsorbed $CO_2$, NO molecules can be successfully capped insides HKUST-1. This finding accelerates the development of using solid porous materials as delivery agent for carrying therapeutic molecules (e.g. CO, NO) and releasing them in humid biomedical context (Horcajada et al., 2011).

B. MIL_101_Cr

Figure 24:
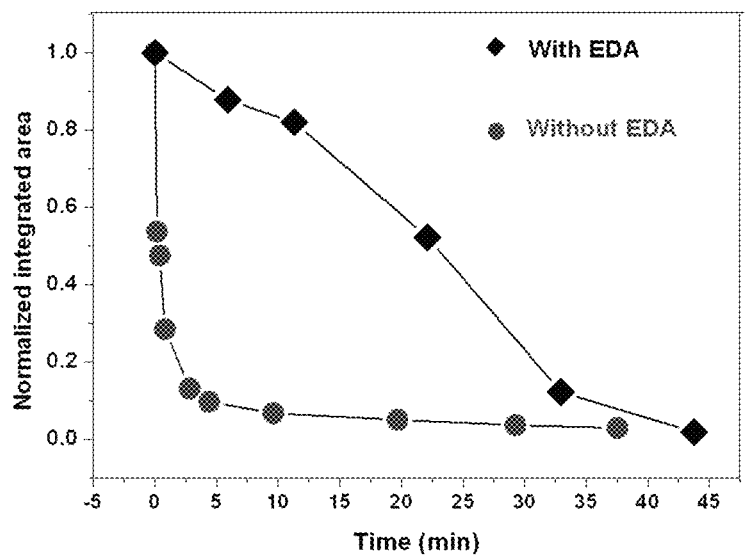
FIG. 24 shows the ν($CO_2$) band evolution upon evacuation in vacuum (<20 mTorr) for MIL_101_Cr with (black diamonds) and without (red circles) post-loaded EDA.

MIL-101(Cr) is built up from a hybrid supertetrahedral building unit, which is formed by terephthalate ligands and trimeric chromium octahedral clusters, possessing high surface area, large windows (12 Å and 16 Å×14.7 Å), mesoporous pores (29 and 34 Å), open metal sites after evacuation (see FIG. 23) (Jeazet et al., 2013 and Férey et al., 2005). The similar loading experiment with $CO_2$+EDA was performed in MIL_101_(Cr). FIG. 24 shows that the $CO_2$ band (at 2337 cm$^{-1}$) intensity in the sample with post-loaded EDA decreases completely within ~45 min, although it is slower than the decrease rate of the pristine sample.

By testing different MOFs structures containing open metal sites including MOF-74, HUKST-1, MIL_101_Cr, it was found that MOF-74 and HKUST-1 can trap $CO_2$ molecules effectively by depositing a surface EDA capping layer. However, MIL_101_Cr could not retain it even after being grafted with EDA molecules. One possible reason could be due to the large open aperture (16 Å) of the free cages in MIL_101_Cr that EDA molecules cannot completely seal the surface.

Example 4—Capping Molecules within MOFs with Open Metal Sites by $NH_3$

Figure 25:
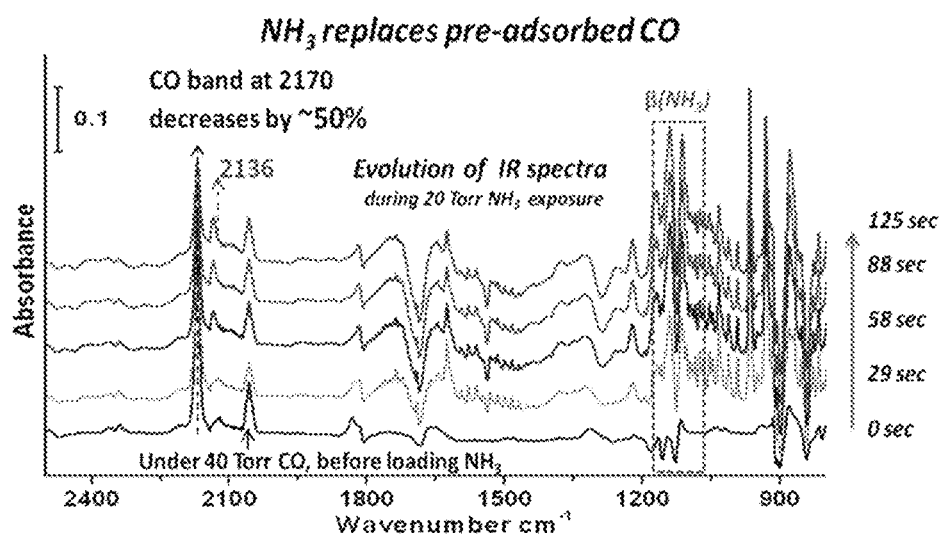
FIG. 25 shows the evolution of infrared spectra of pre-loaded CO molecules in Ni-MOF-74 after introducing mixture gas of CO and $NH_3$ (~40 Torr CO: ~4 Torr $NH_3$). The bottom black spectrum shows the pure CO adsorption after an equilibrium of ~30 min. The middle four spectra show the time dependence features after introducing mixture of CO+$NH_3$ for ~2.5 min and subsequent evacuation within ~10 sec (orange). All the spectra are referenced to the activated MOFs in vacuum.

Upon $NH_3$ loading a previously CO-loaded MOF-74 sample, the intensity of the CO band at 2170 cm$^{-1}$ decreases by ~50% within ~2.5 min and a new band appears at 2136 cm$^{-1}$, shifted from the adsorbed-phase value 2170 cm$^{-1}$ (FIG. 25). This new band is associated with CO molecules displaced by $NH_3$ from primary adsorption sites on the $Ni^{2+}$ to the secondary sites in the middle of the channel or close to the linker (Tan et al., 2015).

Figure 26:
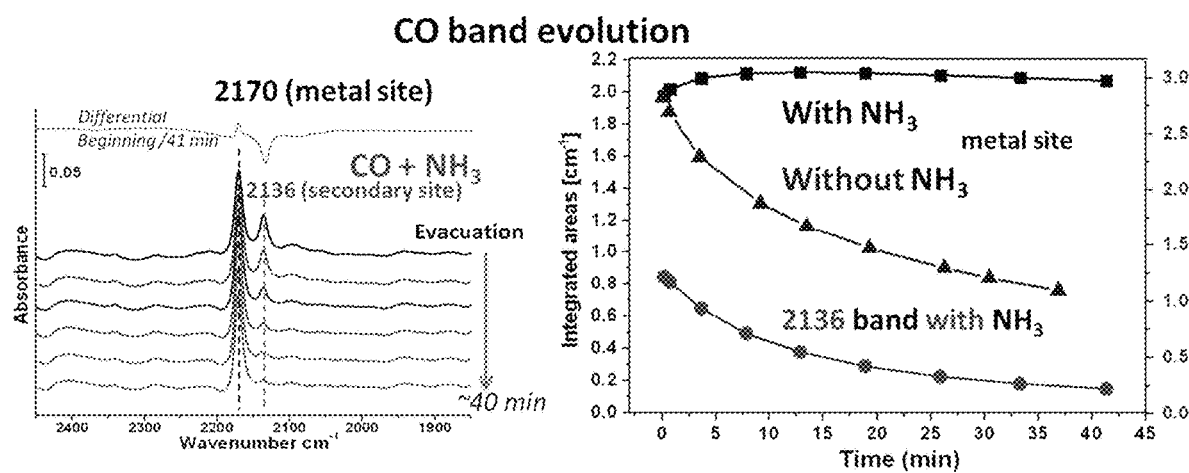
FIG. 26 shows the evolution of CO band in Ni-MOF-74 after exposure to $NH_3$ (~10 Torr) for 2.5 min and subsequent evacuation (<20 mTorr) for 40 min.
Figure 27:
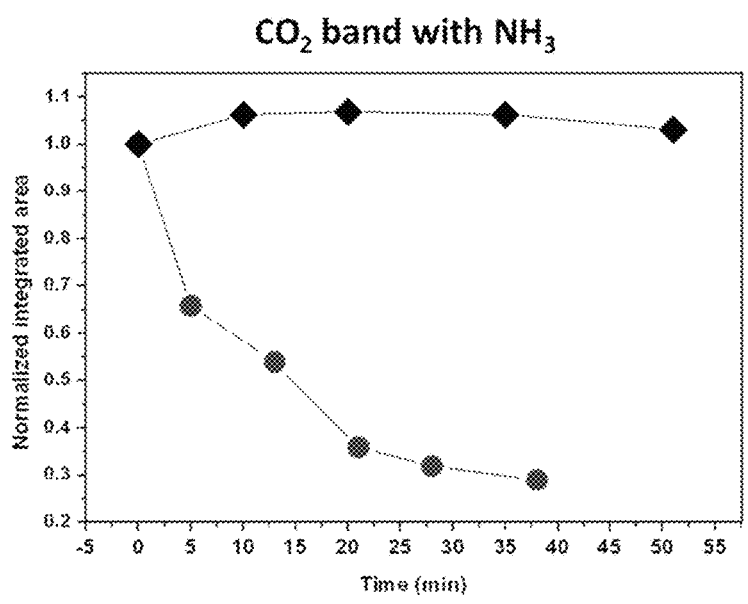
FIG. 27 shows the evolution of $CO_2$ band in Co-MOF-74 after exposure to 10 Torr $NH_3$ for 10 min and subsequent evacuation (<20 mTorr) for 40 min.

After exposing pre-adsorbed CO (gas phase 40 Torr is kept inside the cell) to 10 Torr $NH_3$ for 125 sec, cell was evacuated and the ν(CO) bands at 2170, 2136 cm$^{-1}$ and P($NH_3$) band was monitored (see FIG. 26). 2136 peak gradually diminishes and 2170 band surprisingly remains stable in Ni-MOF-74. The little gain in the differential spectra at 2370 cm-1 can be due to the refilling of CO from secondary site during the evacuation process. This is totally different from CO band decrease from MOFs without $NH_3$ exposure. $NH_3$ also remains stable inside the MOFs. The same observation was also found by $NH_3$+$CO_2$ co-adsorption in Co-MOF-74. FIG. 27 shows the band $CO_2$ evolution upon evacuation with and without $NH_3$ post-exposure.

Figure 28:
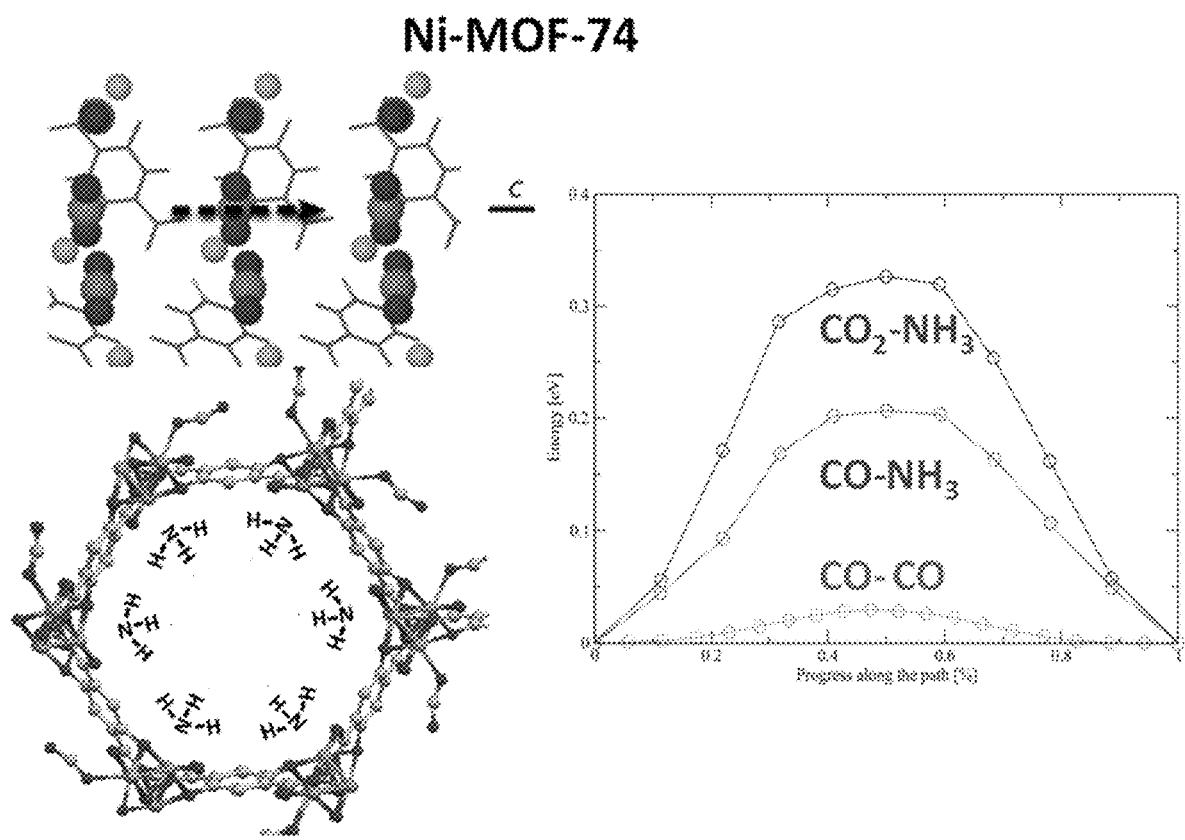
FIG. 28 shows the diffusion progress coordinates of CO, $CO_2$ molecules through $NH_3$.

Although post-exposure of MOF with pre-loaded CO and $CO_2$ to $NH_3$ leads to a decrease of molecules' uptake, the remaining molecules can be well stabilized by additional adsorbed $NH_3$ molecules. This can be explained by increment of diffusing barrier based on DFT calculation. FIG. 28 shows that CO penetrates trough the one-dimensional channel of the MOF fully loaded with the same type of molecule CO by overcoming a diffusion barrier of 0.028 eV, similarly to energy barriers encountered by other small molecules such as $CO_2$ (Canepa et al., 2013). On the other hand, if the metal centers are now saturated with $NH_3$ molecules (scenario depicted in the right panel of FIG. 24), CO encounters an energy barrier of 0.21 eV (red line of FIG. 28), i.e. ~8 times larger. $CO_2$ even encounters a higher energy barrier of 0.32 eV (black line of FIG. 28), i.e. ~10 times larger.

Example 5—Capping Molecules within MOF-74 by Other Alkyl Ammine Molecules

Figures 29A, 29B:
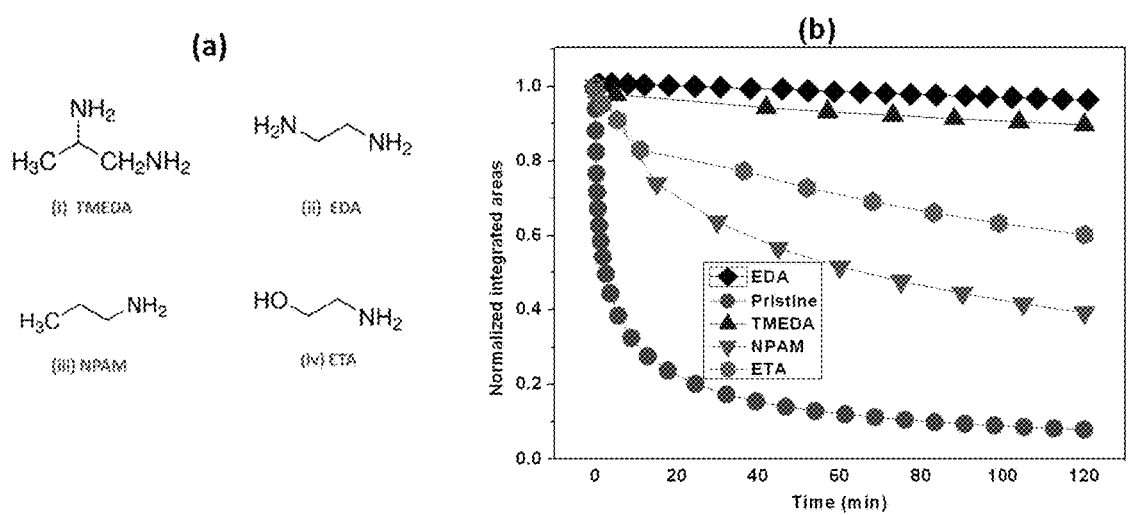
FIGS. 29A & 29B show (FIG. 29A) chemical structure of different alkyl amine molecules: i, trimethylenediamine (TMEDA); ii, ethylenediamine (EDA); iii, n-propylamine (NPAM); iv, ethanolamine (ETA).

Besides ethylenediamine, different alkyl amine molecules including trimethylenediamine, n-propylamine, ethanolamine, have been tried to test the ability of capping small molecules specifically CO within MOF-74. All these alkyl amine molecules can hinder the desorption of CO from MOF-74 to some extent, however, it was found that EDA is the most effective in retaining CO (see FIG. 29). This could be due to their propensity to agglomerate as the capping layer arising from H-bonding of the head amine groups.

Example 6—Selectivity of EDA Monolayer in MOF-74 Toward $C_2H_2$ Over $C_2H_4$ Acetylene ($C_2H_2$) capture and separation from ethylene ($C_2H_4$) is an important industrial process for producing polymer grade $C_2H_4$. Current commercial approaches include partial hydrogenation of acetylene into ethylene over a noble metal catalyst such as a supported Pd catalyst and solvent extraction of cracked olefins using an organic solvent such as DMF and acetone. These technologies have the drawbacks for instance the need of noble metal catalyst and the loss of olefins due to the over hydrogenation to paraffins, the waste of a significant amount of solvents. The search for alternative approach is imperative to save the cost and energy, and further to reduce the waste emission (Hu et al., 2015 and Cui et al., 2016).

Figure 30:
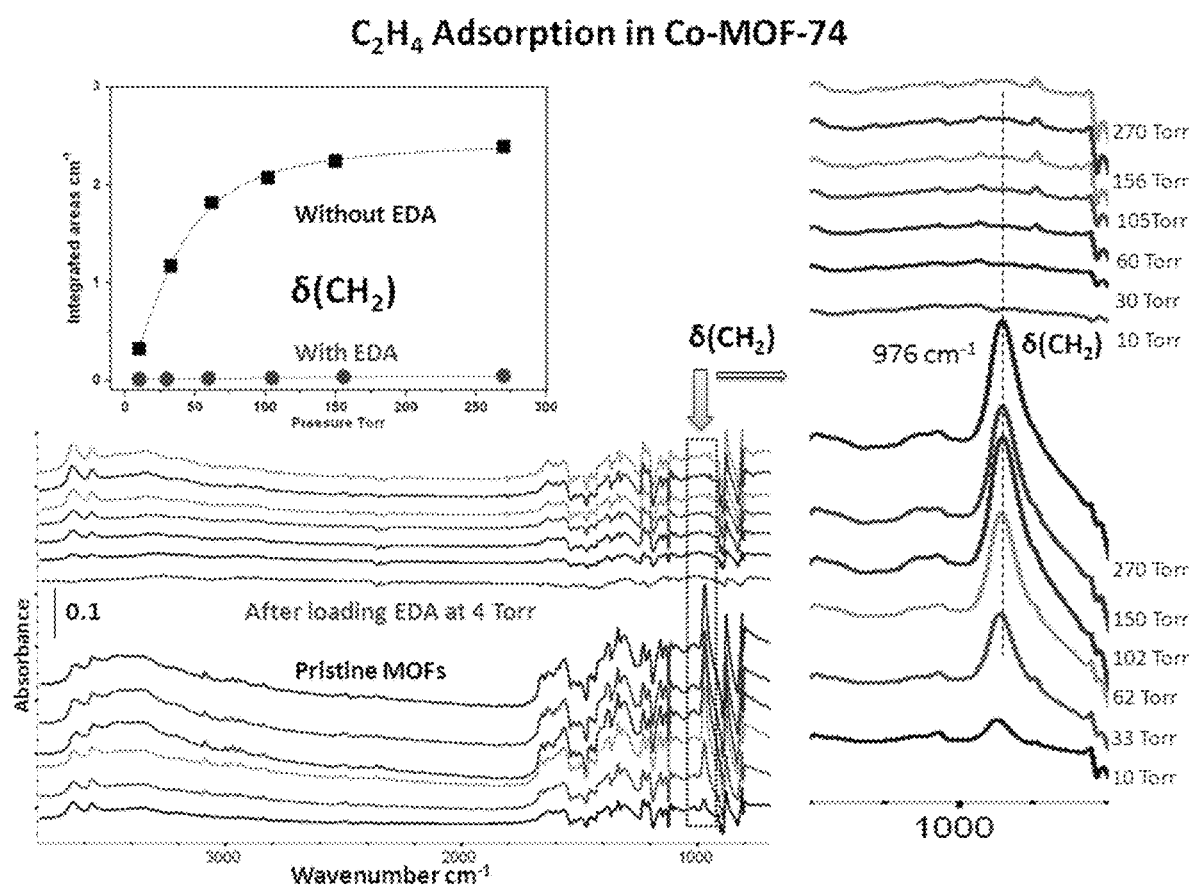
FIG. 30 shows the IR spectra of $C_2H_4$ adsorption into pristine Co-MOF-74 and EDA exposed sample and the evolution of σ($CH_2$) band as a function of pressure.
Figure 31:
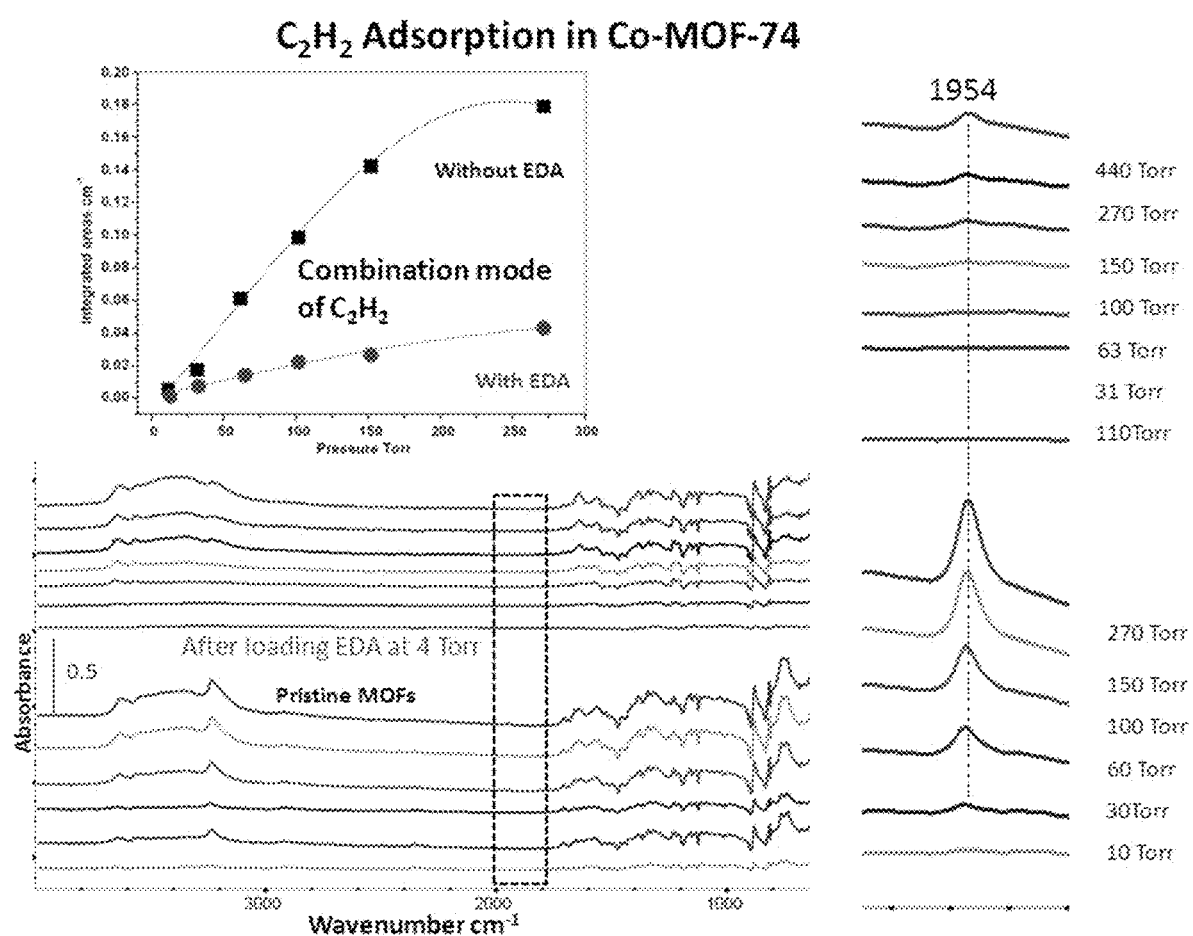
FIG. 31 shows the IR spectra of $C_2H_2$ adsorption into pristine Co-MOF-74 and EDA exposed sample and the evolution of the combination mode at 1954 $cm^{-1}$ as a function of pressure.

The following results show that EDA monolayer could be selective toward $C_2H_2$ over $C_2H_4$, which might offer a new strategy for $C_2H_2$ capture. FIG. 30 shows the comparison between the $C_2H_4$ loading by monitoring the deformation σ($CH_2$) band at 976 cm$^{-1}$ in the pristine and EDA exposed sample. The uptake of $C_2H_4$ is nearly reduced to zero after the MOFs surface is capped by EDA. In contrary, FIG. 31 shows the same EDA capped sample still shows some adsorption for $C_2H_2$ by monitoring its combination mode at 1954 cm$^{-1}$.

Example 7—Additional Studies

A. Post-Loading EDA to Ni-MOF-74 with Pre-Adsorbed CO

After post-loading EDA into Ni-MOF-74 by introducing CO/EDA gas mixture (~40 Torr/~4 Torr) to the cell over ~10 min, the sample is evacuated by pumping the cell under vacuum (<20 mTorr). The signal of gas-phase CO in the cell disappears quickly (<~3 second). The remaining peak at 2170 cm$^{-1}$ is due to the adsorbed CO molecules within the MOFs sample (see purple spectrum in FIG. 2). EDA bands [ν(—NH$_2$), ν(—CH$_2$), β(—NH$_2$)] are difficult to distinguish because they are in frequency ranges associated with MOF phonon modes (from 1700 to 1000 cm$^{-1}$) and adsorbed H$_2$O (>3000 cm$^{-1}$) and may also overlap with the gas-phase EDA spectrum, so only the 1020 cm$^{-1}$ peak is shown in FIG. 3 and used for quantitative analyses. The differential spectrum (top), obtained by subtracting the two spectra after evacuating EDA (the top pink spectrum) and before introducing EDA (black), highlights the characteristic bands due to adsorbed EDA molecules within Ni-MOF-74. These involve ν(—NH$_2$) at 3300 and 3166 cm$^{-1}$, ν(—CH$_2$) at 2938 and 2880 cm$^{-1}$, β(—NH$_2$) at 1644, ν(C—N) at 1020 cm$^{-1}$ (21) (FIG. 2).

B. Post-Loading NH$_3$ to Ni-MOF-74 with Pre-Adsorbed CO

Figure 4:
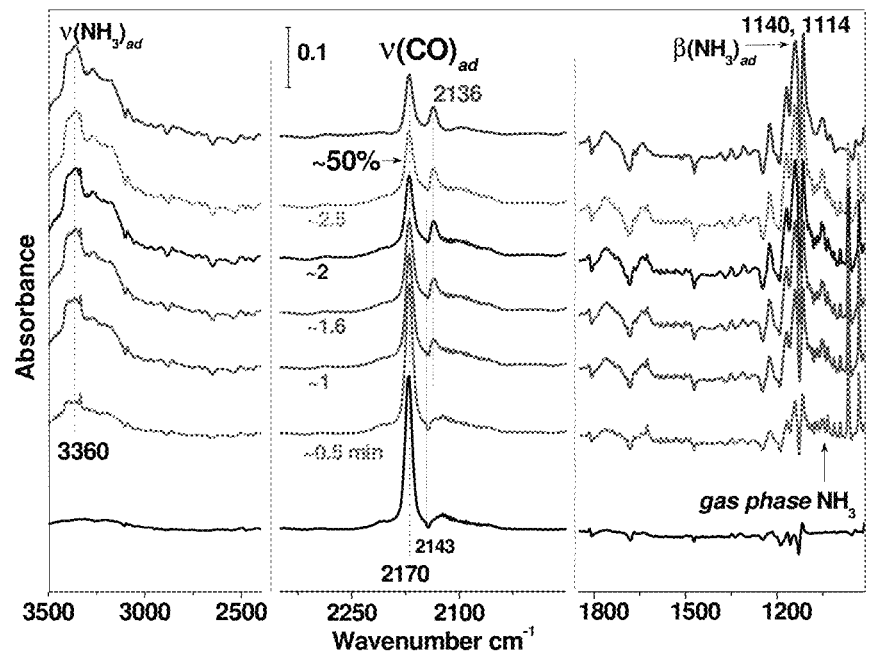
FIG. 4 shows the evolution of infrared spectra of preloaded CO molecules in Ni-MOF-74 after introducing mixture gas of CO and $NH_3$ (~40 Torr CO: ~4 Torr $NH_3$). The bottom black spectrum shows the pure CO adsorption after an equilibrium of ~30 min. The middle six spectra show the time dependence features after introducing mixture of CO+$NH_3$ for ~2.5 min and subsequent evacuation within ~10 sec (orange). The adsorbed $NH_3$ molecules are characterized by the broad ν($NH_3$) band around ~3360 $cm^{-1}$ and β($NH_3$) around ~1114 to ~1140 $cm^{-1}$. All the spectra are referenced to the activated MOFs in vacuum.

Upon NH$_3$ loading a previously CO-loaded sample, the intensity of the CO band at 2170 cm$^{-1}$ decreases by ~50% within ~2.5 min and a new band appears at 2136 cm$^{-1}$, shifted from the adsorbed-phase value 2170 cm$^{-1}$ (FIG. 4). This new band is associated with CO molecules displaced by NH$_3$ from primary adsorption sites on the Ni$^{2+}$ to the secondary sites in the middle of the channel or close to the linker (Tan et al., 2015). This is an example of co-adsorption, in which case the molecular frequency of the first species is shifted due to relocation in the unit cell. Clearly, this does not occur for EDA co-adsorption.

C. Diffusion of CO Along the One-Dimensional Channel of Ni-MOF-74

Figure 9:
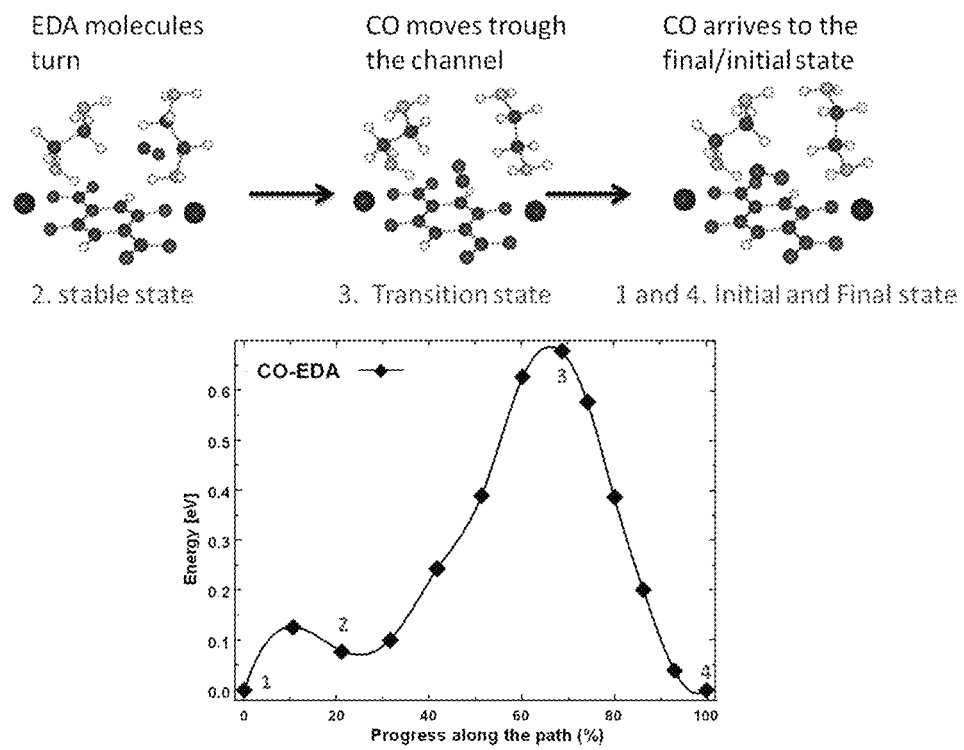
FIG. 9 shows the diffusion progress coordinates of CO molecule through EDA layer. Three figures show the initial state, middle stable state, transition state, and final state.

As demonstrated above, the EDA molecules cluster at the periphery of the MOF (the outmost unit cells) in a structure shown in FIG. 8(a). Therefore, the diffusion of the CO molecules was modeled using two different scenarios: a) all the metal centers saturated with CO molecules (in the absence of EDA cap), and b) all the metal centers saturated with EDA molecules (i.e. through the EDA cap). In both cases, the unit cell contains 6 metal centers, which is a bulk-like environment of the outmost unit cells (i.e. surface effects are neglected). Therefore, without wishing to be bound by any theory, it is believed that this model captures the key elements of the diffusion. To find the lowest energy path, a standard transition-state search algorithm was used, i.e. the nudge elastic band method (NEB), as described in the computational details. In both cases, a CO molecule is placed in the middle of the channel (FIG. 6C and FIG. 8(b)). FIG. 8(b) shows that CO penetrates trough the one-dimensional channel of the MOF fully loaded with the same type of molecules by overcoming a diffusion barrier of 0.028 eV, similarly to energy barriers encountered by other small molecules such as CO$_2$ (Canepa et al., 2013). On the other hand, if the metal centers are now saturated with EDA molecules (scenario depicted in the right panel of FIG. 6C), CO encounters an energy barrier of 0.68 eV (black line of FIG. 6C), i.e. ~24 times larger, due to the larger size of EDA compared to CO. When a CO molecule diffuses through zones where the metal centers are saturated with other CO molecules, they can easily slide though the middle of the one-dimensional channel, barely interacting with the adsorbed CO molecules. In contrast, when a CO molecule diffuses across the channel of the outer pore where EDA molecules are adsorbed on the metal centers, the path is more jagged as CO has to navigate in-between the EDA molecules that are blocking the one-dimensional channel (FIG. 9). Moreover, when CO is in close proximity to EDA hydrogen bonding causes the EDA molecules to move and rotate, which greatly increases the energy barrier. This rotation also explains why the red curve in FIG. 6C is not symmetric.

In summary, CO molecule is able to diffuse freely through the one-dimensional channels on a linear trajectory. The situation is very different in the case where the CO molecule tries to diffuse trough the one-dimensional channel of the MOF fully loaded with EDA molecules: the CO molecule has to navigate across the EDA molecule, as illustrated in FIG. 9. The interaction between the CO molecule and the EDA molecules causes the large energy barrier. Physically, most CO molecules are reflected back into the MOF.

CO is clearly trapped at room temperature, but can be removed by mild annealing under vacuum (pressure <20 mTorr). This is shown in the bottom two spectra in FIG. 3. After annealing to 80° C. (~2 h), only ~23% CO remains and the ν(CO) frequency shifts back to 2174 cm$^{-1}$ (no CO—CO interactions); after 100° C. anneal (~2 h), the trapped CO is almost completely removed (~3% remaining; FIG. 3). Importantly after these annealing steps, the spectroscopic signature of EDA molecules, ν(C—N) band at 1020 cm$^{-1}$ remain (with only less than ~30%, intensity decrease), in accordance with the fact that EDA is more strongly bonded to the framework than CO (FIG. 3), as previously observed in MOFs with unsaturated metal centers (Hwang et al., 2008 and Choi et al., 2012) The system after annealing is now in a state in which CO has been completely removed yet EDA essentially unperturbed. Therefore, the effect of EDA on CO re-adsorption can now be examined, using the same loading conditions (~40 Torr). FIG. 10 shows that the CO uptake is dramatically reduced compared to the pristine activated MOF-74 (EDA-free), taking over 45 min to reach only ~25% of the CO loading obtained in pristine MOF-74 loaded in ~30 min. Note that reloading is intrinsically faster than release because trapped molecules are weakly bound to the MOF in contrast to gas-phase molecules.

D. Post-Loading EDA to Ni-MOF-74 with Pre-Adsorbed CO$_2$, SO$_2$, C$_2$H$_4$

The binding energies of CO$_2$, SO$_2$, and C$_2$H$_4$ in Ni-MOF-74, derived by either isotherm or ab initio calculation, are ~38 kJ/mol, (1) ~50-53.5 kJ/mol, (26, 27) and ~42 kJ/mol, (26) respectively, arising mostly from van der Waals and electrostatic interactions. The loading of CO$_2$, SO$_2$, and C$_2$H$_4$ molecules is performed slightly differently than for CO because the IR absorption of the gas phase of these molecules is too strong at ~40 Torr, making IR absorption experiments of adsorbed gas impossible (FIGS. 34-36). In order to detect the adsorbed guest molecules during EDA post-loading, the following sequence was followed: preloading Ni-MOF-74 with these molecules (>~80 Torr), briefly evacuating (~10 sec), then post-loading EDA molecules with ~4 Torr EDA vapor and immediately monitoring the IR absorption (i.e. desorption rates).

Figures 11A, 11B, 11C:
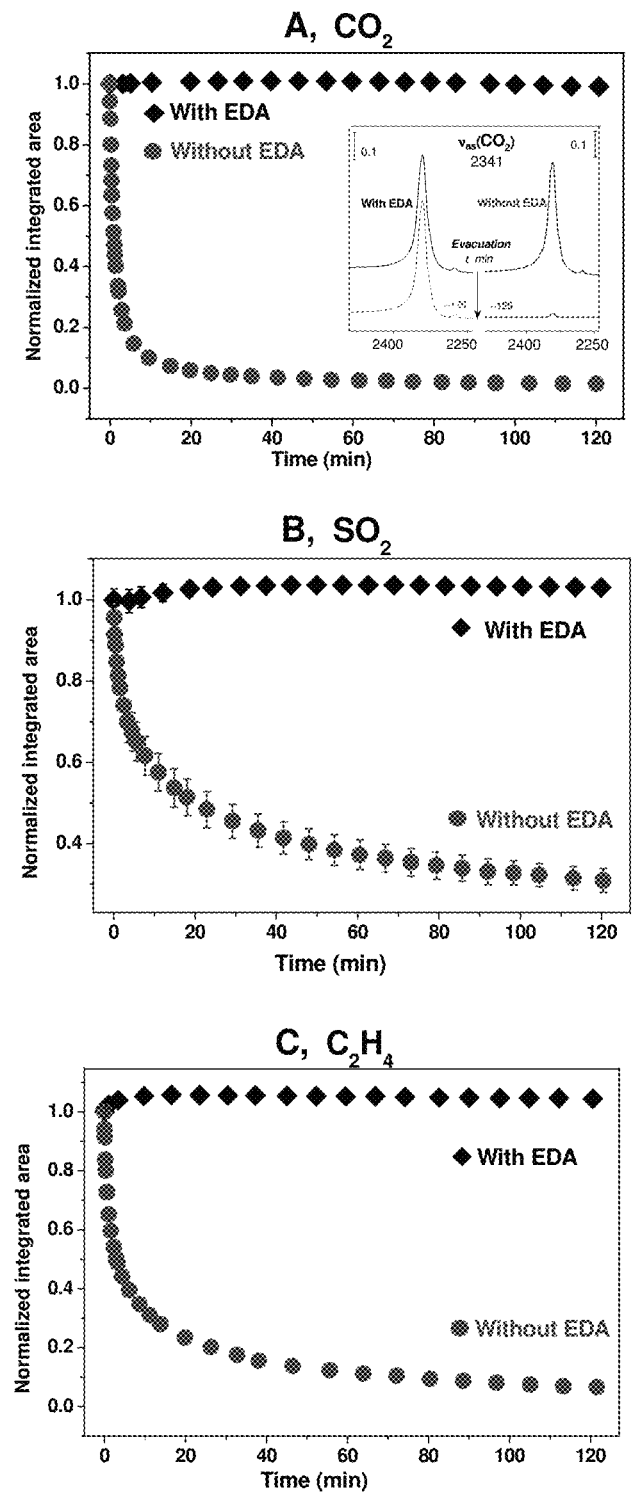
FIGS. 11A-11C show time evolution of the main vibrational bands (a) $\nu_{as}(CO_2)$, (b) $\nu_{as}(SO_2)$ and (c) $\delta(CH_2)$ for (FIG. 11A) $CO_2$, (FIG. 11B) $SO_2$, and (FIG. 11C) $C_2H_4$, respectively, upon evacuation (<20 mTorr) in pristine (red circles) and EDA post-loaded (black diamonds) samples (spectra shown in FIGS. 34-36). For the pristine sample, the initial point (i.e. t=0) is chosen as the peak intensity after evacuation of gas phase for ~10 sec; for MOFs post-loaded with EDA, the starting point is still after gas removal at the end of EDA exposure (i.e. t=0); the integrated areas are normalized to the maximum value obtained at t=0. The inset of FIG. 11A shows the spectra of $\nu_{as}(CO_2)$ band at t=0 and ~120 min. The spectral evolution of the $\nu_{as}(SO_2)$ and $\delta(CH_2)$ bands are shown in FIGS. 35-36. The error bars of normalized integrated area did not exceed ~0.025 for the intensity determination of the $\nu_{as}(CO_2)$ and $\delta(CH_2)$ bands. The larger error bar in panel B for the $\nu_{as}(SO_2)$ band was due to interferences of the MOF phonon bands, leading to uncertainties in determining the baseline in the difference spectra (FIG. 35C).
Figures 34A, 34B, 34C, 34D:
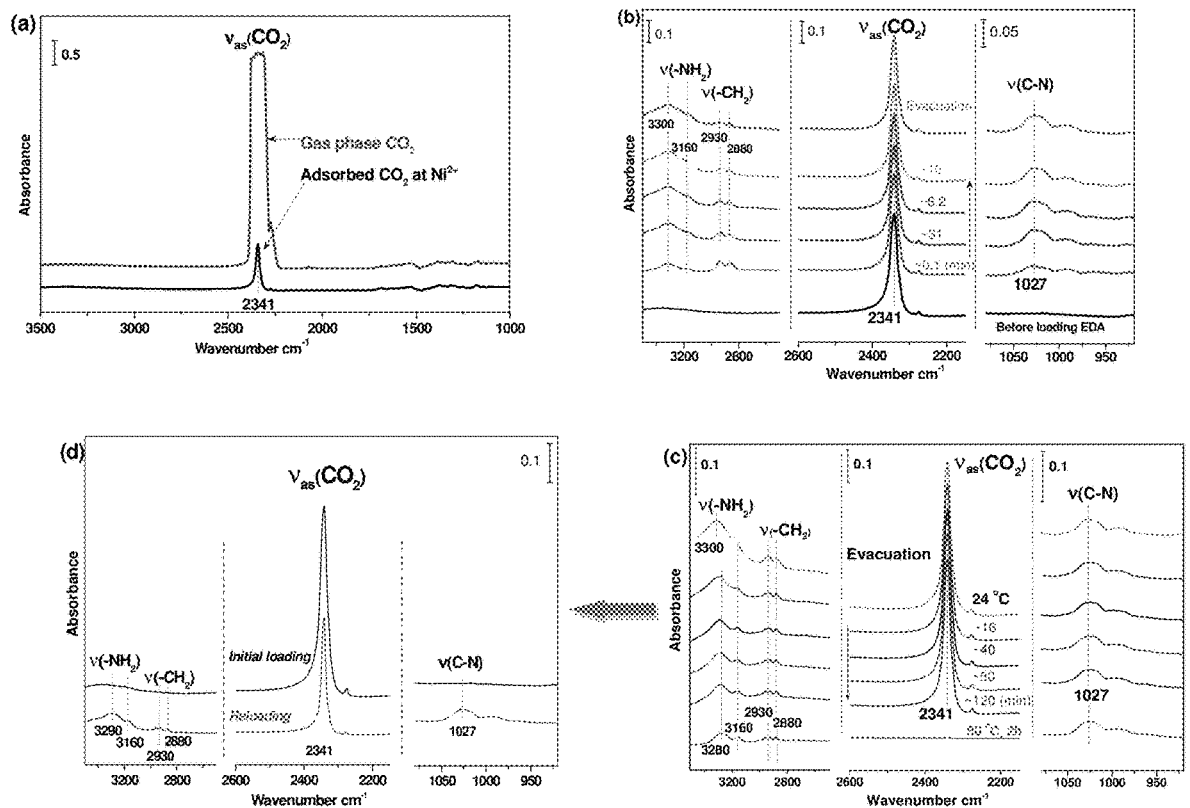
FIGS. 34A-34D show (FIG. 34A) IR spectra of $CO_2$ adsorption in Ni-MOF-74 at a pressure of ~80 Torr (red) and subsequent evacuation within ~10 sec (black). The broad strong peak is due to the gas-phase $CO_2$ signal, while the sharp peak at 2341 $cm^{-1}$ is due to the adsorbed $CO_2$ at open metal site $Ni^{2+}$.

For instance, after loading CO$_2$ into Ni-MOF-74 at ~80 Torr and subsequent evacuation, the CO$_2$ concentration is estimated at 0.64 CO$_2$ molecules per metal site (Yazaydin et al., 2009) Within ~10 seconds evacuation, the pressure of gas-phase CO$_2$ drops below ~500 mTorr (negligible gas-phase IR absorption). The adsorbed CO$_2$ within Ni-MOF-74 is initially detected at 2341 cm$^{-1}$ since its desorption rate is slow (FIG. 34). After introducing ~4 Torr EDA vapor, the IR absorption is recorded for ~10 min during which EDA is kept in the cell. The presence of EDA is confirmed by its ν(NH$_2$), ν(CH$_2$), and ν(C—N) bands (FIG. 34B), and adsorbed CO$_2$ by its ν$_{as}$(CO$_2$) band at 2341 cm$^{-1}$. FIG. 34B shows that, once EDA is adsorbed, the intensity of the CO$_2$ band at 2341 cm$^{-1}$ stops decreasing. The CO$_2$ peak center position also does not shift upon loading EDA. Finally, the system is evacuated and the IR absorption spectrum recorded. Monitoring the $\nu_{as}(CO_2,$ asymmetric stretch) band of $CO_2$ molecules adsorbed at the $Ni^{2+}$ site at 2341 $cm^{-1}$, (Dietzel et al., 2008) the IR spectrum in FIG. 11A shows that the $\nu_{as}(CO_2)$ band remains constant (within error bars) in Ni-MOF-74 after 2 h of evacuation. In contrast, the intensity of this band decreases by >~90% within 20 min in pristine Ni-MOF-74 (FIG. 11A & FIG. 37) because $CO_2$ is weakly bonded to the $Ni^{2+}$ site ($E_{binding}$=38 kJ/mol). The stability of $CO_2$ upon evacuation after post-loading EDA was also measured in Co-MOF-74 and Zn-MOF-74 (FIG. 12), suggesting that EDA capping is effective for all metal centers.

Figures 35A, 35B, 35C, 35D:
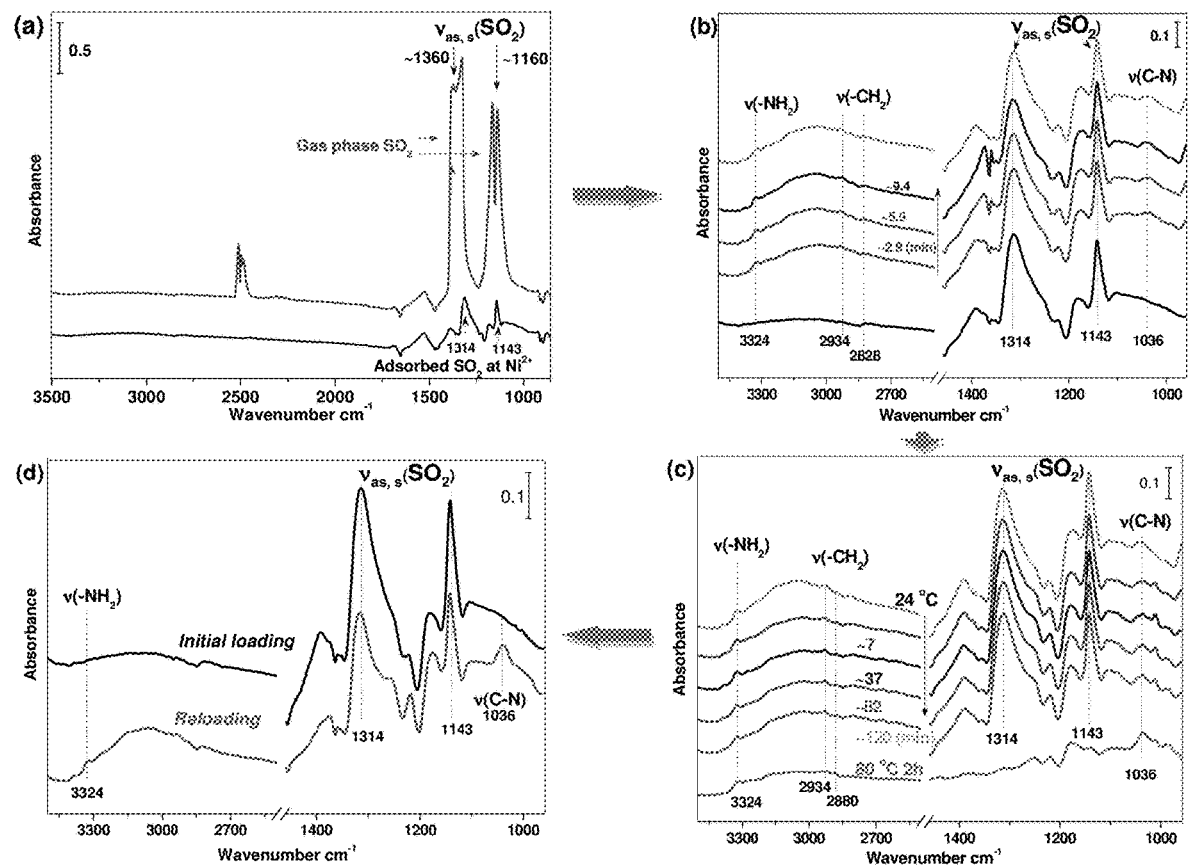
FIGS. 35A-35D show (FIG. 35A) IR spectra of $SO_2$ adsorption in Ni-MOF-74 at a pressure of ~250 Torr (red) and subsequent evacuation within 10 sec (black). The high intensity bands around ~1360 and ~1150 cm$^{-1}$ are due to the gas phase $v_{as}(SO_2)$ and $v_s(SO_2)$ spectra. The sharp peaks at 1314 cm$^{-1}$ and 1143 cm$^{-1}$ are due to the asymmetric band ($v_{as}$) and symmetric band $v_s(SO_2)$ of adsorbed $SO_2$ at the open metal site Ni$^{2+}$.
Figures 37A, 37B, 37C:
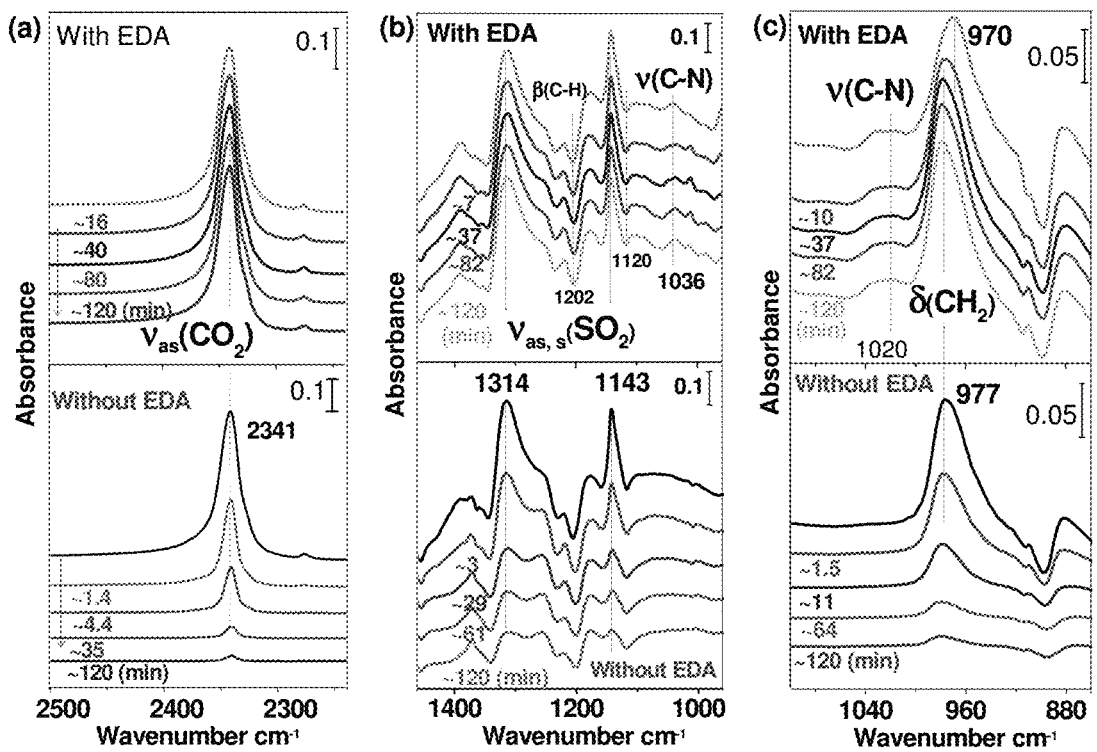
FIGS. 37A-37C show the time dependence spectra of $CO_2$ (FIG. 37A), $SO_2$ (FIG. 37B), $C_2H_4$ (FIG. 37C) desorption under vacuum. The data were collected in Ni-MOF-74 with post-loaded EDA (top panels) and pristine sample without EDA (bottom panels).

After loading $SO_2$ molecules into Ni-MOF-74 at ~250 Torr for 30 min and subsequent evacuation, two major peaks appear at 1314 $cm^{-1}$ and 1143 $cm^{-1}$. These are due to antisymmetric $\nu_{as}$ and symmetric $\nu_s$ bands of physically adsorbed $SO_2$ molecules (FIG. 35A)(Tan et al., 2013) These two bands fall into the phonon mode ($\nu_s(COO)$, $\nu(CO)$, $\beta(CH)$, etc) region of MOF's skeleton, (Tan et al., 2014) which are perturbed due to $SO_2$ inclusion into MOFs structure and produce derivative spectroscopic features around ~1200 to ~1100 $cm^{-1}$ (FIG. 35B & FIG. 37). (Tan et al., 2014 and Tan et al., 2013) After loading EDA into the Ni-MOF-74 at ~4 Torr, the $\nu_{as}(SO_2)$ and $\nu_s(SO_2)$ peaks do not shift or decrease as shown in FIG. 35B. During pumping (FIG. 11B), the concentration of adsorbed $SO_2$ also remains constant in the spectra. This is in stark contrast to the fast decay of these bands in pristine sample (FIGS. 11B & 37). The $SO_2$ concentration within MOFs is recorded by measuring integrated areas of the $\nu_{as}(SO_2)$ peak instead of $\nu_s(SO_2)$ since the asymmetric band $\nu_{as}(SO_2)$ is less affected by $\beta(CH)$ mode perturbation. There is no literature report for the isotherm data of $SO_2$ adsorption in Ni-MOF-74. According to previous measurement of $SO_2$ in Mg-MOF-74, (Tan et al., 2013) the occupation at ~250 Torr is slightly above ~0.9 molecules per $Mg^{2+}$ site at 297 K.

Figures 36A, 36B, 36C, 36D:
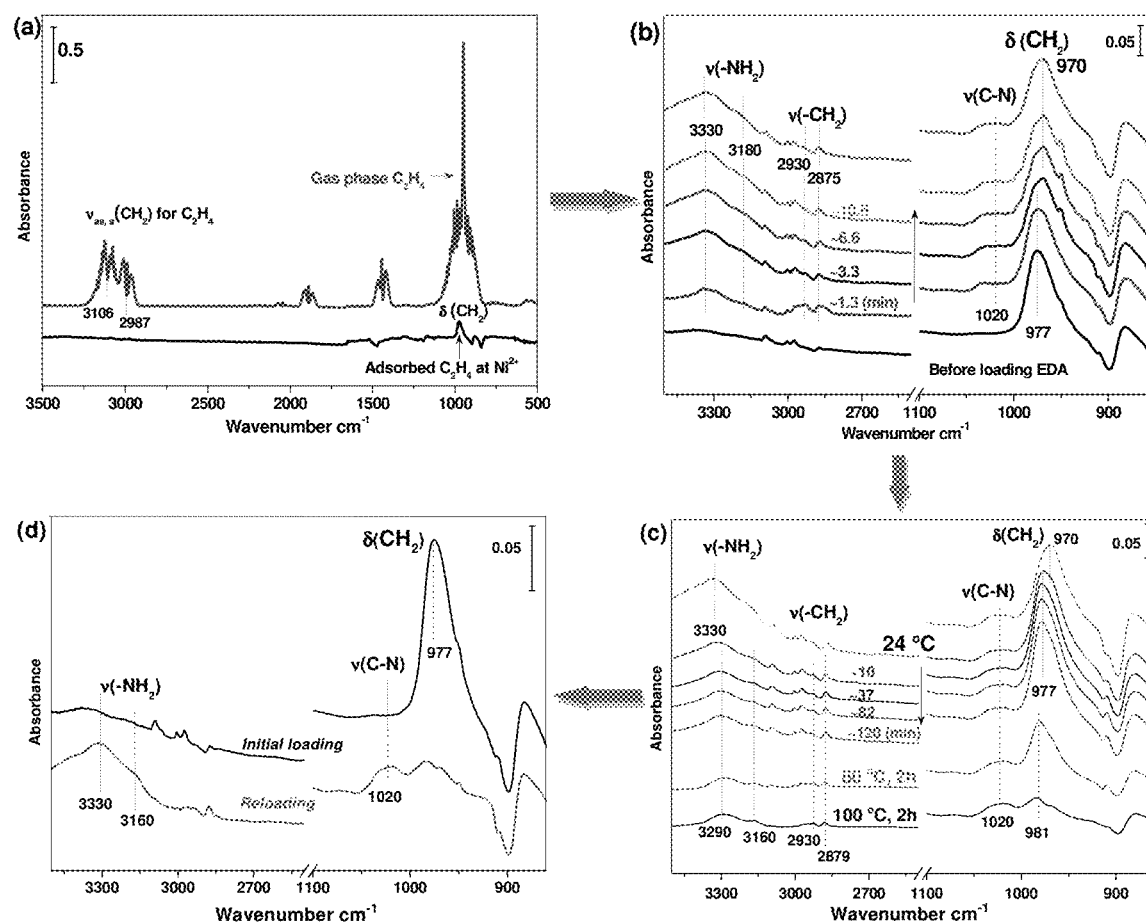
FIGS. 36A-36D show (FIG. 36A) IR spectra of $C_2H_4$ adsorption in Ni-MOF-74 at a pressure of ~200 Torr (red) and subsequent evacuation within ~10 sec (black). The broad doublet peaks centered at 3106 cm$^{-1}$ and 2987 cm$^{-1}$ in the red spectra are due to the gas phase mode of asymmetric $v_{as}(CH_2)$ and symmetric $v_s(CH_2)$. The broad peak centered at 949 cm$^{-1}$ is due to the wagging vibration $\delta(CH_2)$ of adsorbed $C_2H_4$ molecules at open metal site Ni$^{2+}$. After evacuation of gas phase, the $v_{as}(CH_2)$ mode of adsorbed $C_2H_4$ is weak and overlaps with the derivative feature of $v(-CH)$ mode of benzene ring of MOF linker. The strong $\sigma(CH_2)$ band falls into the MOF-74's phonon gap (Tan, et al., 2014) and is observable in the black spectrum.

$C_2H_4$ adsorption in Ni-MOF-74 is also reversible at room temperature. (Chavan et al., 2009) The most-distinct band was observed at 977 $cm^{-1}$ after loading $C_2H_4$ at ~200 Torr (FIG. 36A) and evacuating gas phase, which was attributed to the $\delta(CH_2,$ wagering) mode. (Chavan et al., 2009) There is no literature report for the isotherm data of $C_2H_4$ adsorption in Ni-MOF-74. According to Bohme's measurement, the occupation of $C_2H_4$ in both Mg, Co-MOF-74 reaches ~0.6 molecules per metal site at 295 K. (Bohme et al., 2013) Upon evacuation under vacuum, the absorption bands gradually drops, by over 90% within 2 h. (see red curve of FIG. 11C and spectra of FIG. 37). After post-loading EDA at ~4 Torr, the mode $\nu(C-N)$ for EDA appears at ~1020 $cm^{-1}$, close to $\delta(CH_2)$ wagging mode at 977 $cm^{-1}$ (FIG. 36B). However, this $\delta(CH_2)$ mode itself is not affected significantly after EDA exposure except for a shift to 970 $cm^{-1}$. This shift of ~7 $cm^{-1}$ could be due to the interaction of $C_2H_4$ molecules with trace amount of $H_2O$ impurities adsorbed into MOFs during loading EDA. After pumping for >10 min, it shifts back to the original position at 977 $cm^{-1}$ due to the removal of these water species (FIG. 36C). The intensity of $\delta(CH_2)$ mode remains exceptionally stable during subsequent evacuation, which is in stark contrast to the fast decay of these bands in pristine sample (FIGS. 11C & 37)

All the trapped $CO_2$, $SO_2$, $C_2H_4$ molecules can be removed by mild annealing (>80° C.) as shown in FIGS. 34C, 35C, & 36C, so that reloading experiments can be performed. The results are all similar to those for CO: the uptake is lower after EDA exposure and mild annealing (FIGS. 34D, 35D, & 36D). These findings suggest that in all cases EDA molecules act as a cap that prevents molecule release from and re-adsorption into MOF-74.

E. Interaction Between Water and EDA Molecules within MOFs

Figure 17:
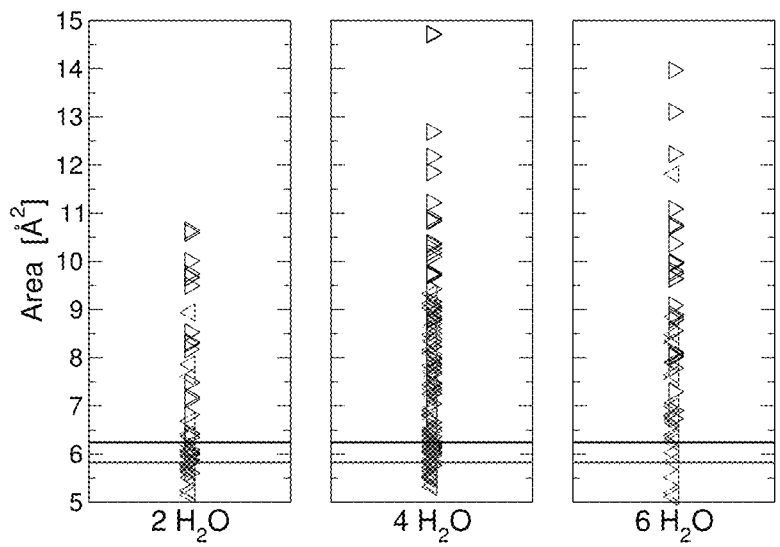
FIG. 17 shows the areas of the black and red triangles depicted in FIG. 15Cii and FIG. 15Civ upon adding 2, 4, and 6 $H_2O$ molecules. As indicated in FIG. 15Cii, there are 8 adsorption sites for a water molecule. Thus, there are 28 ways to add 2 $H_2O$ molecules, 70 ways to add 4 $H_2O$ molecules, and 28 ways to add 6 $H_2O$ molecules; results for all those possibilities are given in the three plots. The solid lines represent the areas of the triangles without any water molecules. In the majority of cases a significant increase of the triangular area is observable upon adding water, constituting a gate-opening mechanism that greatly enhances diffusion.

As indicated in FIG. 15c, there are 8 adsorption sites for a water molecule in the vicinity of the EDA layer. There are therefore 28 ways to add 2 $H_2O$ molecules, 70 ways to add 4 $H_2O$ molecules, and 28 ways to add 6 $H_2O$ molecules. Given all these possible configurations, the resulting areas of the black and red triangles for all those configurations are shown in FIG. 17. It is clear that, while some configurations do not increase the triangle areas, most configurations do increase them to a large extend (more than twice in some cases). Similarly for the binding energies given in FIG. 18: calculations are performed for each possible configuration, clearly showing that the presence of water decreases the binding energy substantially.

F. Raman Spectra for as-Synthesized and EDA Post-Loaded Ni-MOF-74 Samples

Figure 38:
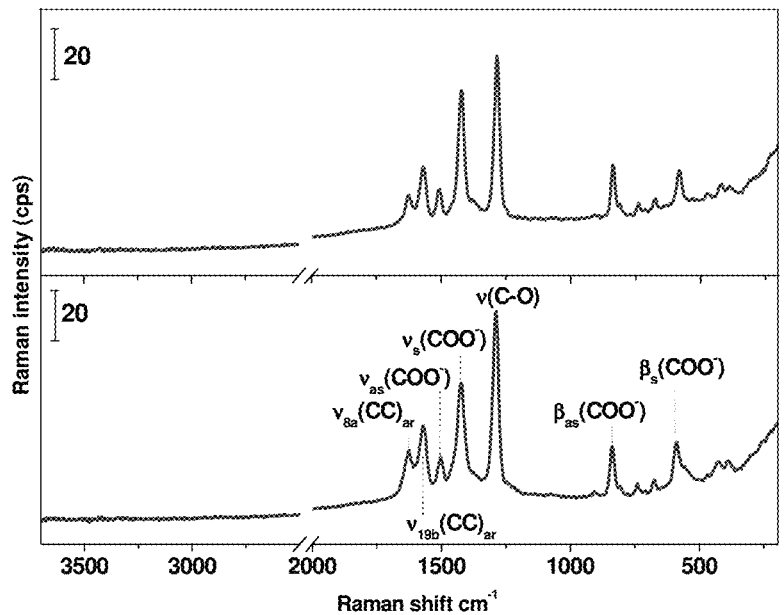
FIG. 38 shows the raman spectra for as-synthesized (bottom panel, black) and post-loaded EDA (top panel, purple) Ni-MOF-74.

Raman spectra of both as-synthesized sample after solvent exchange and sample with post-loaded EDA were collected by using a Nicolet Almega XR Dispersive Raman spectrometer from Thermo Fisher Scientific, Inc. A 780 nm laser was used for excitation, the output power was reduced to 10% (0.41 mW) to avoid sample decomposition induced by laser heating. As shown in FIG. 38, The spectra are dominated by the bulk MOF phonon modes of the carboxylate, phenolate, and aromatic rings, such as $\nu_{as,s}(COO)$, $\beta_{as,s}(COO-)$ $\nu(C-O)$, and $\nu(C=C)_{aromatic\ ring}$, as we have assigned before (Tan et al., 2014). The spectroscopic features for EDA modes such as $\nu(NH_2)$ above ~3000 $cm^{-1}$, $\nu(CH_2)$ between ~3000 and ~2800 $cm^{-1}$, $\nu(C-N)$ between ~1100 and ~900 $cm^{-1}$, (Krishnan et al., 1966) $\nu(Ni-N)$ in the between ~400 and ~230 $cm^{-1}$ region, (Nakamoto, 2009) cannot clearly be detected in Raman spectrum. This suggests that the amount of EDA adsorption is minimal, only located at the periphery (surface region) of the MOF microcrystals. Furthermore, no notable changes in the spectrum upon post-loading EDA, confirm that the MOF crystalline structure is maintained.

Example 8—Fundamental Model

Figure 39:
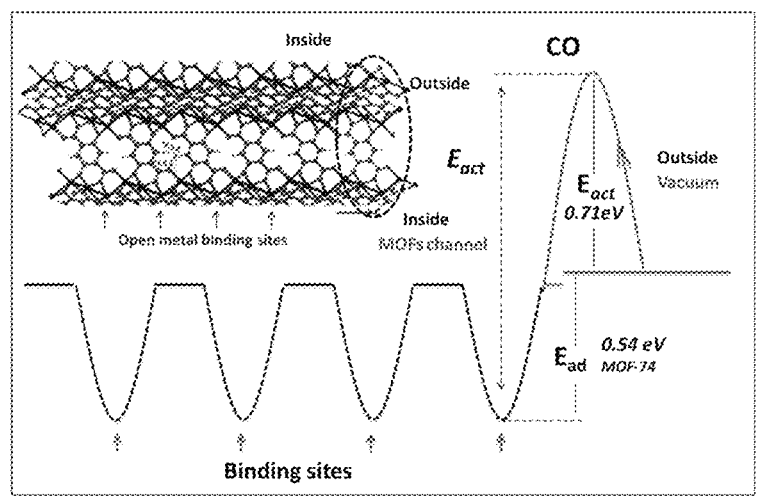
FIG. 39 shows a hypothetical schematic potential energy curve on an optimal path from the gas phase (right) to the channel with effective binding sites (left).
Figure 40:
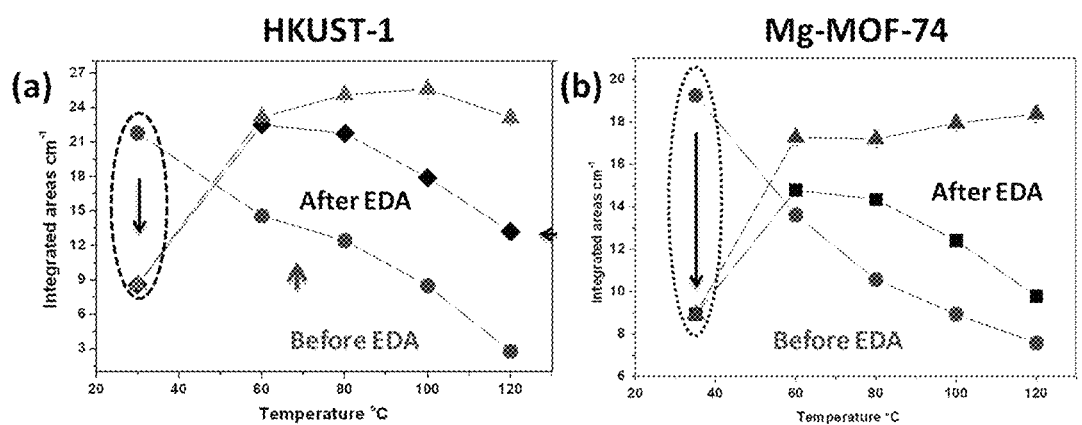
FIGS. 40A & 40B shows integrated areas of $v_{as}$ ($CO_2$) band in EDA capped MOFs (red circle) and uncapped MOFs (black diamond in HKUST-1 or square in Mg-MOF-74) as a function of temperature at constant pressure of ~80 Torr $CO_2$ in (FIG. 40A) HKUST-1 sample.

Without wishing to be bound by any theory, it is believed that the simplistic, quantitative model based on CO molecule is shown in FIG. 39 may explain the following observation of enhanced adsorption ($CO_2$, $C_2H_4$, $C_2H_4$) by thermal activation. The presence of EDA layer on the external surface constitutes a barrier for CO molecules to enter inside the MOFs channel. The barrier was calculated to be 68 kJ/mol (0.71 eV) by vdW-DF modeling (Tan et al., 2016) Once the molecules overcome the barrier by increasing the temperature to enter into the bulk of materials, the CO molecules can be regarded to be delocalized and move freely through the channel with a small diffusion barrier of 0.03 eV. The CO molecules are then bound to the preferential sorption sites (i.e. exposed metal ions) with a binding energy of ~52.3 kJ/mol (0.54 eV) derived by isotherm measurement. During the desorption process, the molecules need to overcome a much higher energy barrier (~52.3 kJ/mol+~68 kJ/mol) to go through the channel, and are thus trapped inside MOFs Example 9—$CO_2$ Capture at High Temperature The pristine metal organic frameworks HKUST-1 and MOF-74 were coated with EDA by vapor phase deposition and then gas molecules were loaded into these EDA capped MOFs. In $CO_2$ measurement, ~80 Torr was selected as a constant pressure to examine the temperature dependent adsorption since the partial pressure of $CO_2$ at flue gas is ~80 Torr (Yazaydin et al., 2009). The same loading procedure was performed on $CO_2$. The $CO_2$ adsorption at ~80 Torr was first measured at 30° C. Since the IR absorption of the gas phase of $CO_2$ is too strong at ~80 Torr, making IR absorption experiments of adsorbed gas impossible. In order to detect the adsorbed guest $CO_2$, the following sequence was followed: preloading MOFs at ~80 Torr $CO_2$ for 30 min, briefly evacuating (~5 sec), the pressure of $CO_2$ gas phase then dropped below ~500 mTorr (negligible gas phase IR absorption) and the adsorbed $CO_2$ peak vas was clearly distinguished in the spectra. $CO_2$ adsorption was measured at different temperatures and the results are shown in FIG. 40A-B. After fully evacuating $CO_2$ from the MOFs, the sample was exposed to EDA vapor again at ~4 Torr for 10 min and the external surface was terminated with EDA vapor. $CO_2$ at ~80 Torr was loaded into MOFs at different temperatures and adsorption uptake was recorded by measuring the integrated areas of $v_{as}$ band at the certain temperature. $CO_2$ adsorption in EDA capped MOFs reaches maximum at 60° C. in both Co-MOF-74 and HKUST-1, suggesting EDA layers plays the major role in controlling the $CO_2$ adsorption. Most significantly, above 60° C., $CO_2$ uptake in EDA capped even exceed that in uncapped MOFs materials at the same condition, and provides a strategy to trap $CO_2$ at elevated temperature. If the loading procedure is modified such that $CO_2$ is introduced at high temperature, kept at high temperature for 30 min, and then the sample cooled back to room temperature to measure absorption, $CO_2$ uptakes were found to be increased.

Example 10—Selectivity Using Temperature ($C_2H_2$ and $C_2H_4$)

The binding energies of $C_2H_2$ and $C_2H_4$ in MOF-74 are quite similar (Lee et al., 2015), which makes MOF-74 materials difficult for separation application. The temperature dependent measurements (FIG. 40 and FIG. 41) show that, under equal pressure, $CO_2$ and $C_2H_2$ uptake reach the maximum value at 60° C. and 80° C. respectively in EDA capped MOFs. However, $C_2H_4$ requires at least 100 OC to reaches saturation, which indicates that the diffusion barriers of $C_2H_2$ and $C_2H_4$ are different. Difference in the diffusion barrier provides a possible opportunity for selective adsorption.

Figure 41:
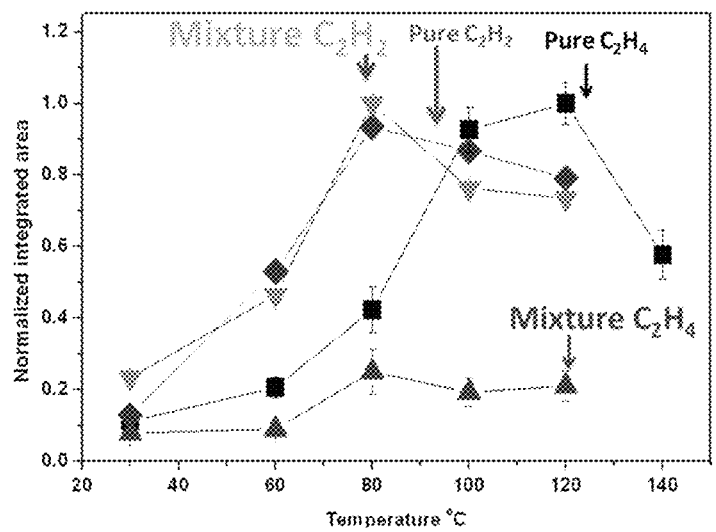
FIG. 41 shows integrated areas of $\beta(CH)$ for $C_2H_2$ (blue diamond and orange triangle) and $C_2H_4$ (black square and red triangle) adsorbed within EDA capped Co-MOF-74 in both pure phase and mixture gas phase as function of temperature.

In the first tests, the mixture phase was examined under equivalent partial pressure. ~300 Torr/~300 Torr of $C_2H_2$/$C_2H_4$ mixture was introduced into the cell and subsequently evacuated for being kept for ~30 min. At different temperatures, it is found that $C_2H_2$ adsorption, obtained by measuring the intensity of $\beta(CH_2)$ mode, is slightly affected compared to pure phase ~300 Torr $C_2H_2$ (FIG. 41). However, $C_2H_4$ adsorption was greatly reduced compared to pure phase ~300 Torr $C_2H_4$. Without wishing to be bound by any theory, it is believed that this observation may be explained by the diffusion barrier difference that $C_2H_2$ diffuses more easily through EDA cap into the MOFs channel. Once the effective adsorption site is occupied by $C_2H_2$, $C_2H_4$ adsorption are prevented by the preoccupied $C_2H_2$.

All of the compositions and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compositions and methods without departing from the spirit, scope, and concept of the disclosure. All variations and modifications apparent to those skilled in the art are deemed to be within the spirit, scope, and concept of the disclosure as defined by the appended claims.

REFERENCES

The following references, to the extent that they provide exemplary procedural or other details supplementary to those set forth herein, are specifically incorporated herein by reference.

Andirova et al., ChemSusChem, n/a, 2015.
Berland et al., Rep. Prog. Phys. 78:066501, 2015.
Bloch et al., J. Am. Chem. Soc. 136, 10752, 2014.
Bohme et al., Langmuir 29:8592, 2013.
Bonino et al., Chem. Mater. 20:4957, 2008.
Canepa et al, Phys. Rev. Lett. 110:026102, 2013.
Caskey et al., J. Am. Chem. Soc. 130, 10870, 2008.
Chavan et al., Response of CPO-27-Ni towards CO, N2 and C2H4. PCCP 11:9811, 2009.
Chernysh et al., Appl. Surf. Sci. 326:285, 2015.
Choi et al., J. Phys. Chem. Lett 3:1136, 2012.
Chopra et al., Chem. Mater., 2015.
Chui et al., Science 283:1148, 1999.
Cohen, Chem. Rev. 112:970, 2012.
Cristaudo et al., Surf. Interface Anal. 46:79, 2014.
Cui et al., B. Chen, Science, 2016.
Dietzel et al., Chem. Commun., 5125, 2008.
Ding et al., J. Phys. Chem. C 116, 22987, 2012.
Férey et al., Science, 309:2040-2042, 2005.
Ferey, Chem. Soc. Rev., 37:191-214, 2008.
Furukawa, et al., Science, 341, 2013.
Garrone et al., Chem. Soc. Rev. 34:846, 2005.
Hadjiivanov and Vayssilov, in Advances in Catalysis. Volume 47:307-511, 2002.
Henkelman and Jónsson, J. Chem. Phys 113:9978, 2000.
Henkelman et al., J. Chem. Phys. 113:9901, 2000.
Hibbe et al., J. Am. Chem. Soc. 133:2804-2807, 2011.
Horcajada et al., Chem. Rev., 112:1232-1268, 2011.
Hu et al., Nat Commun, 6, 2015.
Hwang et al., Angew. Chem. Int. Ed. 47:4144, 2008.
Hwang et al., Angew. Chem. Int. Ed. 47:4144, 2008.
Jeazet et al., Membranes, 3:331, 2013.
Kitagawa, et al., Angew. Chem. Int. Ed., 43:2334-2375, 2004.
Krishnan et al., Inorg. Chem. 5:852, 1966.
Kuppler et al., Coord. Chem. Rev. 253:3042, 2009.
Langreth et al., J. Phys.: Condens. Matter. 21:084203, 2009.
Lee et al., Chem. Mater. 27:668, 2015.
Lee et al., Energy Environ. Sci 7:744, 2014.
Li et al., Chem. Rev. 112:869, 2011.
Liu et al., Chemistry—An Asian Journal 8:778, 2013.
Liu et al., Langmuir 24:4772, 2008.
McDonald et al., J. Am. Chem. Soc. 134:7056, 2012.
Mulfort et al., Chem. 47:7936, 2008.
Nakamoto, Infrared and Raman Spectra of Inorganic and Coordination Compounds, 6th ed. Wiley & Sons, Inc., Hoboken, N.J., United States., 2009.
Nijem et al., J. Am. Chem. Soc. 132:14834, 2010.
Nijem et al., J. Am. Chem. Soc. 134:15201-15204, 2012.
Nour et al., J. Phys.: Condens. Matter. 24:424203, 2012.
Paolo et al., J. Phys.: Condens. Matter 21:395502, 2009.
Seah et al., J. Phys. Chem. B. 119:13433, 2015.
Seah et al., J. Phys. Chem. B., 119:3297, 2015.

Seah et al., The Journal of Physical Chemistry B 119:13433, 2015.
Songolzadeh et al., Sci. World J., 34, 2014.
Suh et al., Chem. Rev. 112:782, 2011.
Sumida et al., Chem. Rev. 112:724, 2011.
Tan et al., Chem. Mater. 25:4653, 2013.
Tan et al., Chem. Mater. 26:6886, 2014.
Tan et al., Chem. Mater., 27:2203-2217, 2015.
Tan et al., Nat. Comm., 7:13871, 2016.
Thonhauser et al., Phys. Rev. B 76:125112, 2007.
Thonhauser et al., Phys. Rev. Lett. 115:136402, 2015.
Yazaydin et al. J. Am. Chem. Soc. 131:18198-18199, 2009.
Vimont et al., J. Am. Chem. Soc. 128:3218, 2006.
Wang et al., Microporous Mesoporous Mater. 55:217, 2002.
Wang et al., Microporous Mesoporous Mater., 55:217-230, 2002.
Wu et al., J. Am. Chem. Soc. 131: 4995, 2009.
Xiang et al., J. Am. Chem. Soc. 131:12415, 2009.
Xiao et al., J. Am. Chem. Soc., 129, 1203-1209, 2007.
Yamada et al., Mater. Sci. Eng. R-Rep 34:231, 2001.
Yamada, Eur. Phys J. D 9:55, 1999.
Yazaydin et al., Chem. Soc., 131:18198-18199, 2009.
Yazaydin et al., J. Am. Chem. Soc. 131:18198, 2009.
Yun et al., J. Mater. Chem. C 3:276, 2015.
Zhou et al., J. Am. Chem. Soc. 130:15268, 2008.

What is claimed is:

1. A composition comprising:
   (A) nanoporous material;
   (B) ethylenediamine; and
   (C) a guest molecule;
   wherein the guest molecule is contained within the nanoporous material and the ethylenediamine penetrates not greater than 1 nm toward the interior of the nanoporous material.

2. The composition of claim 1, wherein the ethylenediamine is deposited such that the amine group of the ethylenediamine is bound to a metal atom of the nanoporous material.

3. The composition of claim 1, wherein the nanoporous material is a metal organic framework.

4. The composition of claim 3, wherein metal organic framework comprises a pore diameter of less than 25 Å.

5. The composition of claim 3, wherein the metal organic framework is further defined by the formula: ML, wherein:
   M is a metal ion; and
   L is a ligand;
the metal organic framework is further defined by the formula $M_2L$, wherein:
   M is a metal ion; and
   L is a ligand of the formula:

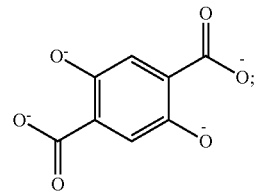

the metal organic framework is further defined by the formula: $M_2L_3$ wherein:
   M is a trivalent metal ion; and
   L is a divalent ligand; or
the metal organic framework is further defined by the formula: $M_3L_2$ wherein:
   M is a metal ion; and
   L is a trivalent ligand.

6. The composition of claim 1, wherein the guest molecule is CO, $CO_2$, $SO_2$, NO, $C_2H_2$ or $C_2H_4$.

7. A method of preparing a composition of claim 1 comprising reacting a nanoporous material with a gaseous mixture comprising ethylenediamine.

8. The method of claim 7, further comprising a guest molecule.

9. The method of claim 8, wherein the guest molecule is a gas.

10. The method of claim 9, wherein the guest molecule is CO, $CO_2$, $SO_2$, NO, $C_2H_2$ or $C_2H_4$.

11. The composition of claim 1, wherein the ethylenediamine is disposed as a monolayer on the exterior surface of the nanoporous material.

12. The composition of claim 1, wherein the ethylenediamine is not present within internal pores of the nanoporous material.

13. The composition of claim 1, wherein an amine of the ethylenediamine is deposited at a surface opening of the pores of the nanoporous material.

* * * * *

UNITED STATES PATENT AND TRADEMARK OFFICE
CERTIFICATE OF CORRECTION

PATENT NO. : 11,173,470 B2
APPLICATION NO. : 15/729350
DATED : November 16, 2021
INVENTOR(S) : Tan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 680 days.

Signed and Sealed this
Thirty-first Day of January, 2023

Katherine Kelly Vidal
*Director of the United States Patent and Trademark Office*